(12) United States Patent
Burroughs et al.

(10) Patent No.: US 8,057,434 B2
(45) Date of Patent: Nov. 15, 2011

(54) INJECTION APPARATUS HAVING A NEEDLE CASSETTE FOR DELIVERING A PHARMACEUTICAL LIQUID

(75) Inventors: Andrew Christopher Burroughs, Kenosha, WI (US); Anastasios G. Karahalios, Lincolnwood, IL (US); Kenneth Alan Ritsher, Chicago, IL (US); Anthony Lawrence Schaff, Sr., Carmel, IN (US)

(73) Assignee: Eli Lilly and Company, Indianapolis, IN (US)

( * ) Notice: Subject to any disclaimer, the term of this patent is extended or adjusted under 35 U.S.C. 154(b) by 1225 days.

(21) Appl. No.: 10/598,990

(22) PCT Filed: Mar. 30, 2005

(86) PCT No.: PCT/US2005/010580
§ 371 (c)(1), (2), (4) Date: May 8, 2007

(87) PCT Pub. No.: WO2005/097237
PCT Pub. Date: Oct. 20, 2005

(65) Prior Publication Data
US 2007/0233001 A1    Oct. 4, 2007

(51) Int. Cl.
*A61M 37/00* (2006.01)
(52) U.S. Cl. .................................................. 604/131
(58) Field of Classification Search ................ None
See application file for complete search history.

(56) References Cited

U.S. PATENT DOCUMENTS

| | | | |
|---|---|---|---|
| 2,605,765 A | 8/1952 | Kollsman | |
| 4,203,518 A | 5/1980 | Current | |
| 5,080,648 A | 1/1992 | D'Antonio | |
| 5,147,311 A | 9/1992 | Pickhard | |
| 5,224,596 A | 7/1993 | Kruger | |
| 5,285,896 A | 2/1994 | Salatka et al. | |
| 5,318,522 A | 6/1994 | D'Antonio | |
| 5,545,145 A | 8/1996 | Clinton et al. | |
| 5,569,190 A | 10/1996 | D'Antonio | |

(Continued)

FOREIGN PATENT DOCUMENTS

EP    0 709 104 B1    11/1998

(Continued)

*Primary Examiner* — Nicholas D Lucchesi
*Assistant Examiner* — Pritesh Patel
(74) *Attorney, Agent, or Firm* — Edwin J. Prein; Gregory A. Cox

(57) ABSTRACT

An apparatus for delivering a pharmaceutical liquid to a patient includes an outer casing; a needle cassette housed in the casing and containing a plurality of mutually parallel drug injection needles; a drug cartridge housed in the casing, containing a liquid and including a sealable aperture for accessing the liquid; a direct drive assembly housed in the casing and engageable with the drug cartridge to expel a measured dose of the liquid through the aperture; a lifter assembly housed in the casing and engageable with the needle cassette to drive one of the plurality of needles partially out of the casing and into a patient while also accessing the liquid in the drug cartridge through the scalable aperture, and thereafter to withdraw the needle from the patient while halting access of the liquid through the sealable aperture after the measured dose of the liquid has been administered through the needle; motor means in the casing for driving the direct drive assembly and the lifter assembly; computer means for activating the direct drive assembly and the lifter assembly; and a control panel for enabling a user to activate the apparatus.

15 Claims, 42 Drawing Sheets

U.S. PATENT DOCUMENTS

| | | |
|---|---|---|
| 5,616,132 A | 4/1997 | Newman |
| 5,775,498 A | 7/1998 | Kashanchi |
| 5,814,020 A | 9/1998 | Gross |
| 5,829,589 A | 11/1998 | Nguyen et al. |
| 5,858,001 A | 1/1999 | Tsals et al. |
| 5,873,462 A | 2/1999 | Nguyen et al. |
| 5,928,201 A | 7/1999 | Poulsen et al. |
| 5,957,895 A | 9/1999 | Sage et al. |
| 6,032,543 A | 3/2000 | Arthun et al. |
| 6,277,091 B1 | 8/2001 | Genet |
| 6,325,241 B1 | 12/2001 | Garde et al. |
| 6,346,094 B2 | 2/2002 | West et al. |
| 6,364,865 B1 | 4/2002 | Lavi et al. |
| 6,478,771 B1 | 11/2002 | Lavi et al. |
| 6,500,150 B1 | 12/2002 | Gross et al. |
| 6,540,675 B2 | 4/2003 | Aceti et al. |
| 6,616,616 B2 | 9/2003 | Fritz et al. |
| 6,723,068 B2 | 4/2004 | Lavi et al. |
| 6,824,529 B2 | 11/2004 | Gross et al. |
| 6,843,782 B2 | 1/2005 | Gross et al. |
| 6,939,324 B2 | 9/2005 | Gonnelli et al. |
| 7,004,928 B2 | 2/2006 | Aceti et al. |
| 7,025,774 B2 | 4/2006 | Freeman et al. |
| 7,338,472 B2 | 3/2008 | Shearn |
| 7,361,163 B2 | 4/2008 | Cohen |
| 2002/0169416 A1 | 11/2002 | Gonnelli et al. |
| 2003/0083686 A1 | 5/2003 | Freeman et al. |
| 2003/0153900 A1 | 8/2003 | Aceti et al. |
| 2004/0186432 A1 | 9/2004 | Barry et al. |
| 2005/0149090 A1 | 7/2005 | Morita et al. |
| 2005/0154410 A1 | 7/2005 | Conway et al. |
| 2005/0234494 A1 | 10/2005 | Conway et al. |
| 2006/0264996 A1 | 11/2006 | LeVaughn et al. |
| 2010/0152660 A1* | 6/2010 | Mack et al. .......... 604/136 |

FOREIGN PATENT DOCUMENTS

| | | |
|---|---|---|
| JP | 10043296 | 2/1998 |
| WO | 95/13838 | 5/1995 |
| WO | 01/87388 A1 | 11/2001 |
| WO | 01/89607 A2 | 11/2001 |
| WO | 01/93927 A1 | 12/2001 |
| WO | 02/00101 A2 | 1/2002 |
| WO | 02/11797 A1 | 2/2002 |
| WO | 02/11798 A1 | 2/2002 |
| WO | 02/28456 A1 | 4/2002 |
| WO | 02/100465 A1 | 12/2002 |
| WO | 03/030810 A1 | 4/2003 |
| WO | 03/066128 A2 | 8/2003 |
| WO | 2004/012796 A1 | 2/2004 |
| WO | 2004/030726 A1 | 4/2004 |
| WO | 2004/030728 A2 | 4/2004 |
| WO | 2004/098682 A2 | 11/2004 |
| WO | 2004/098683 A1 | 11/2004 |
| WO | 2004/098685 A1 | 11/2004 |
| WO | 2004/110299 A2 | 12/2004 |
| WO | 2005/002649 A1 | 1/2005 |
| WO | 2005/011779 A1 | 2/2005 |
| WO | 2005/018709 A2 | 3/2005 |
| WO | 2006/004859 A2 | 1/2006 |

* cited by examiner

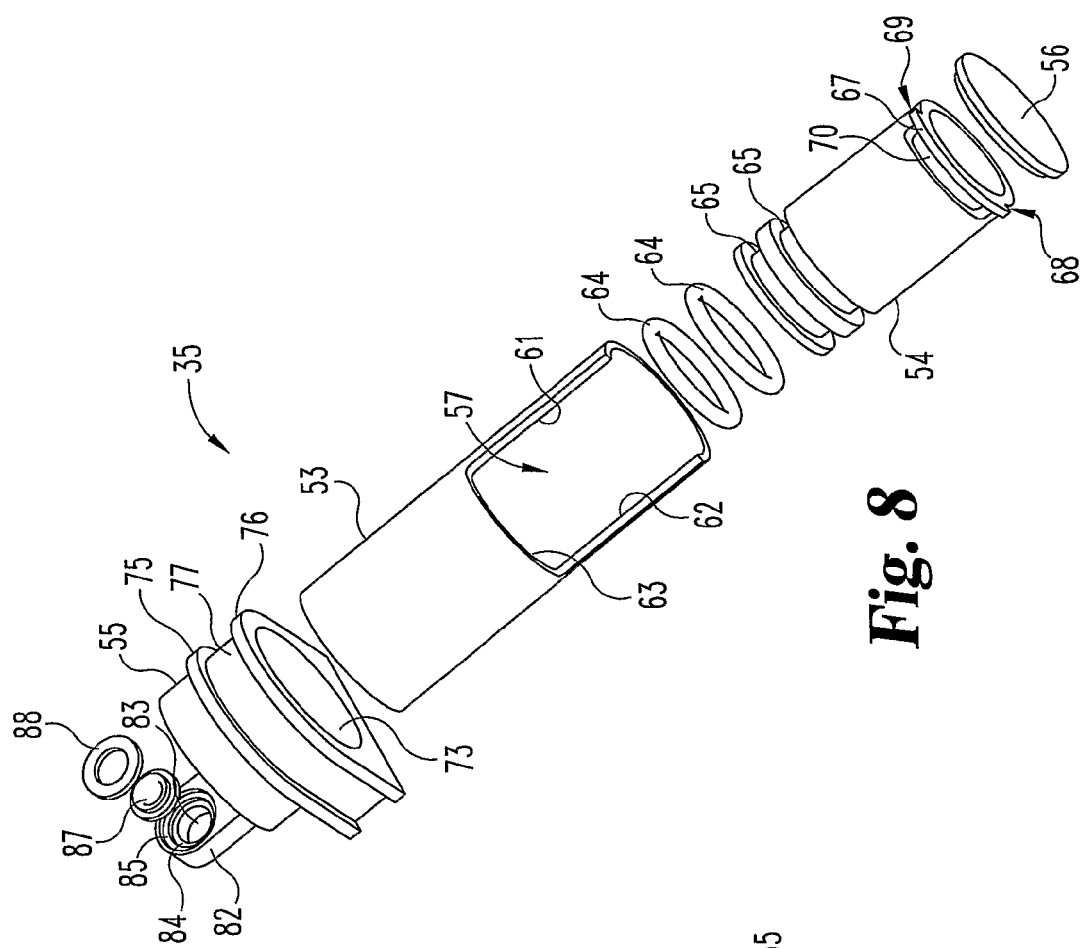
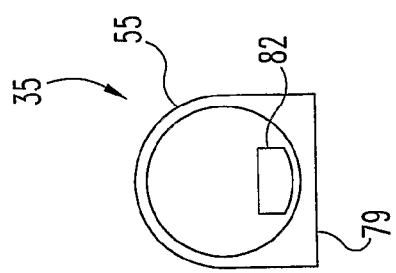
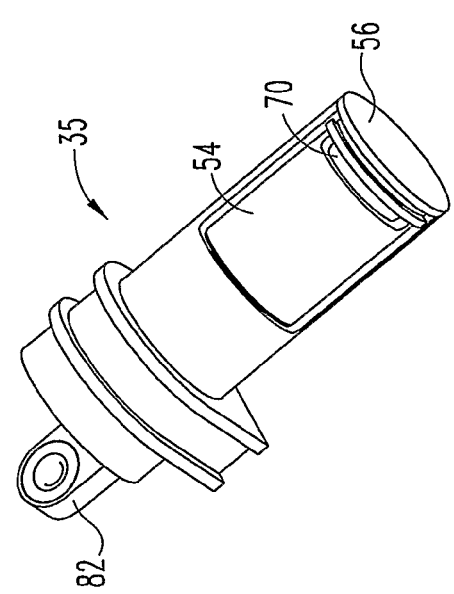
Fig. 7
Fig. 8
Fig. 9

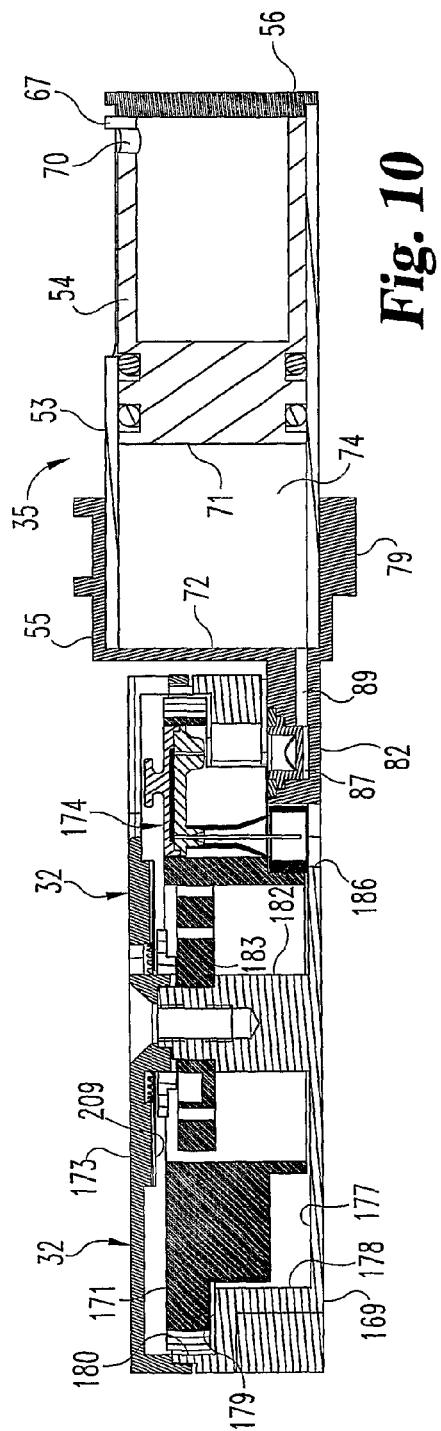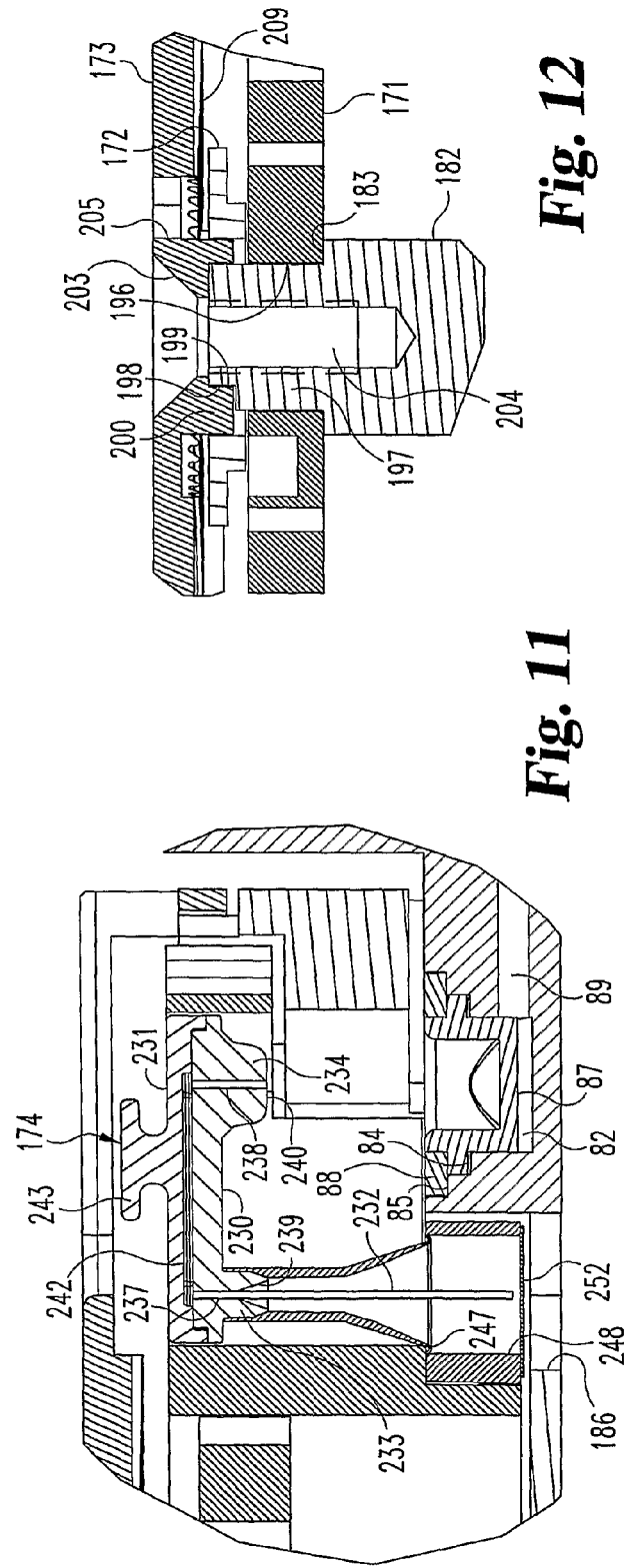

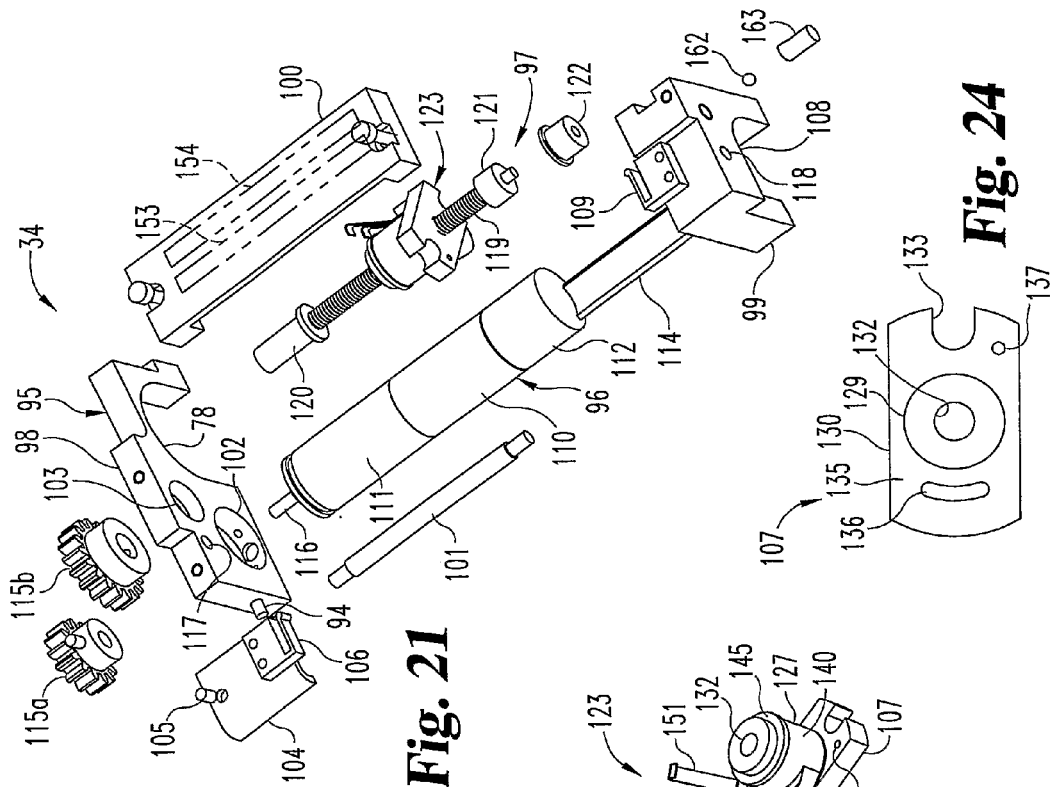
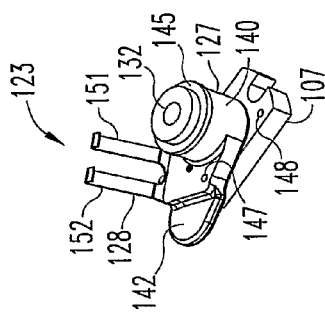
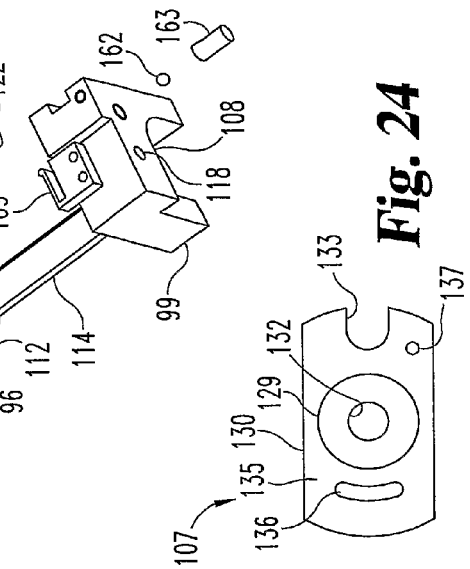
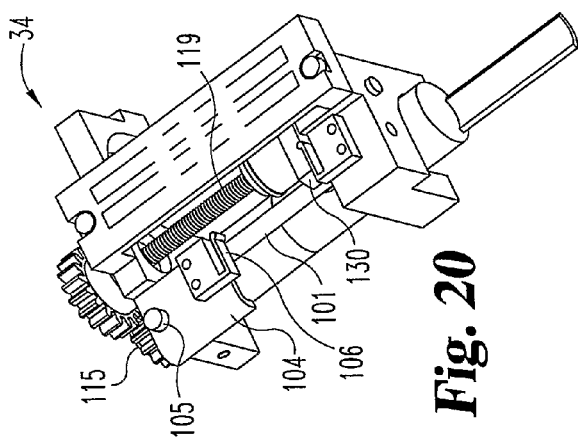
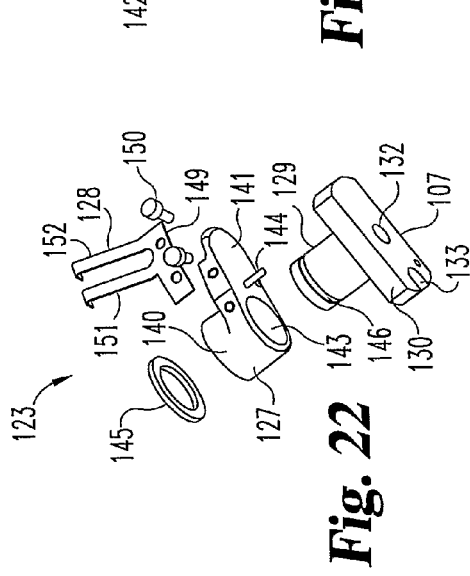

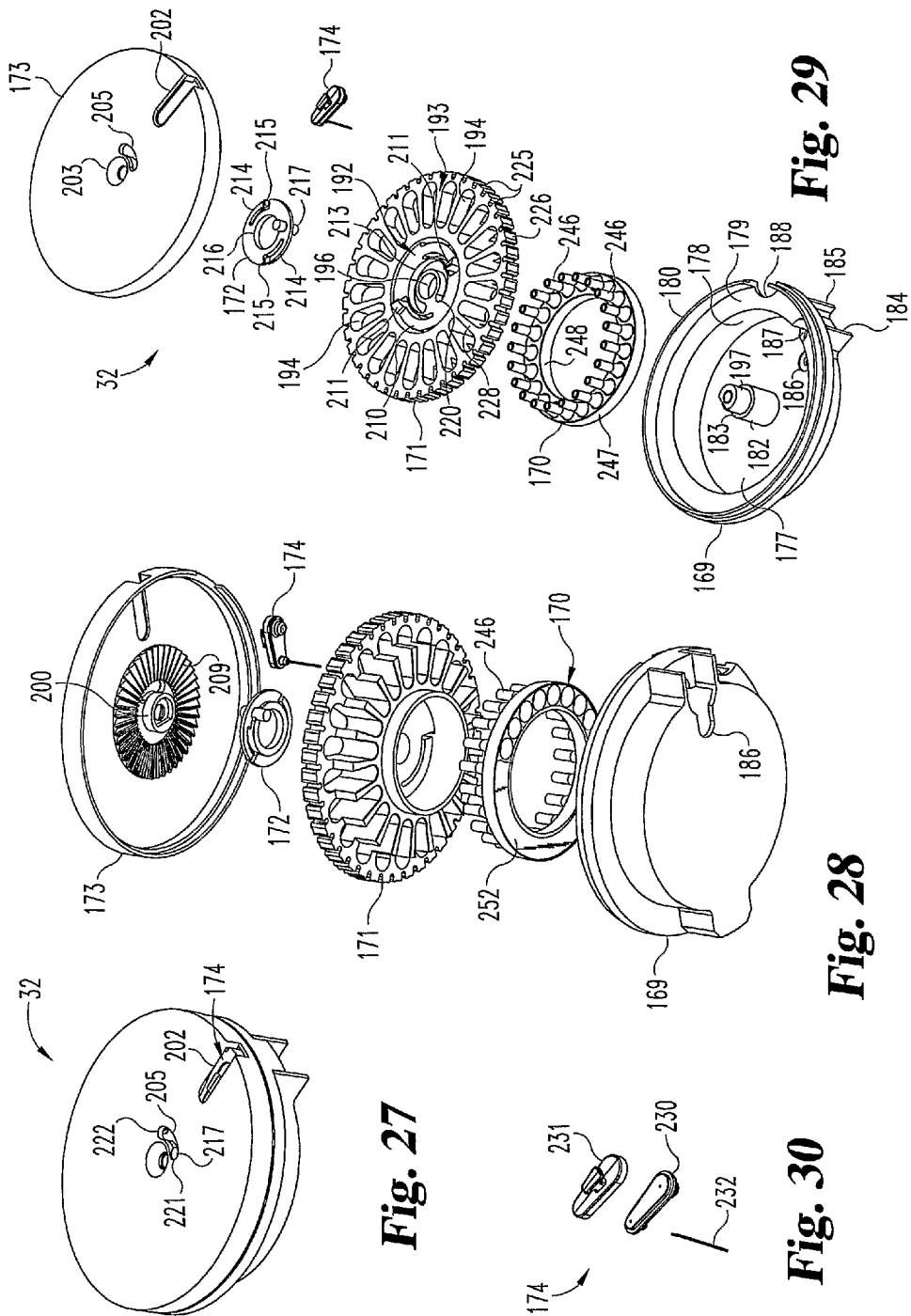

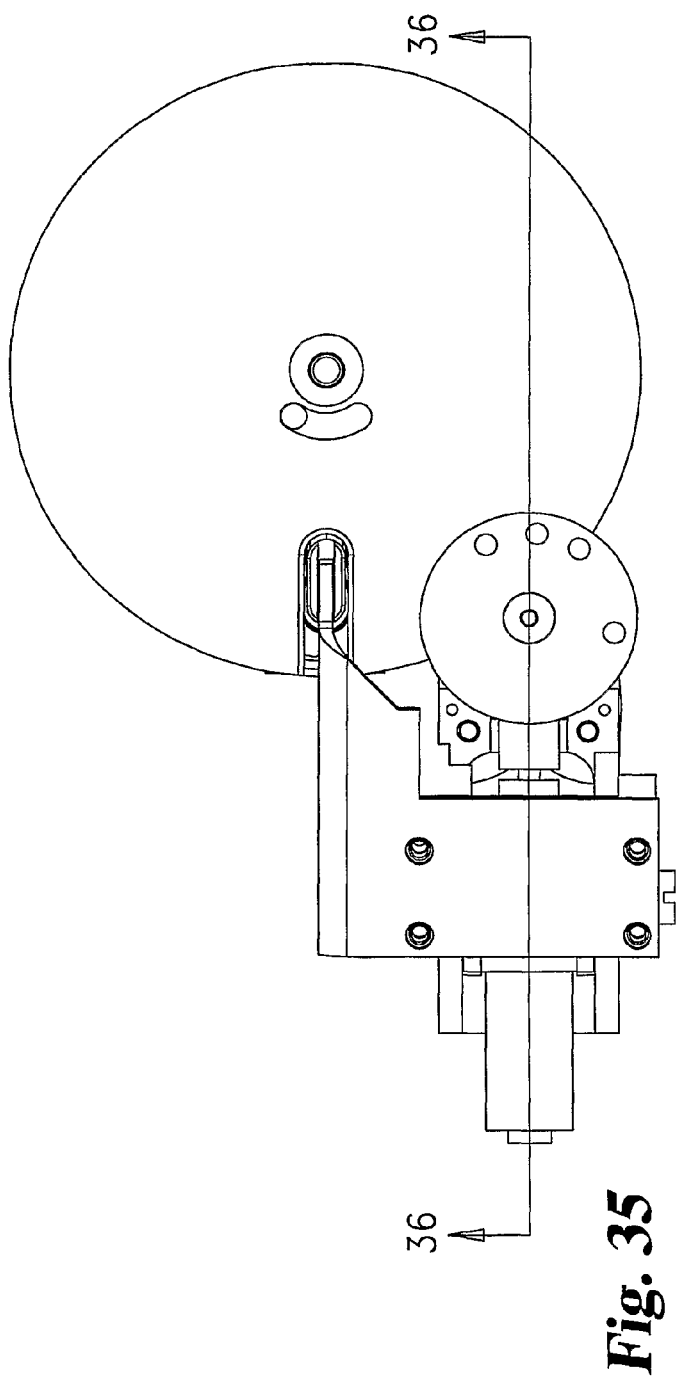
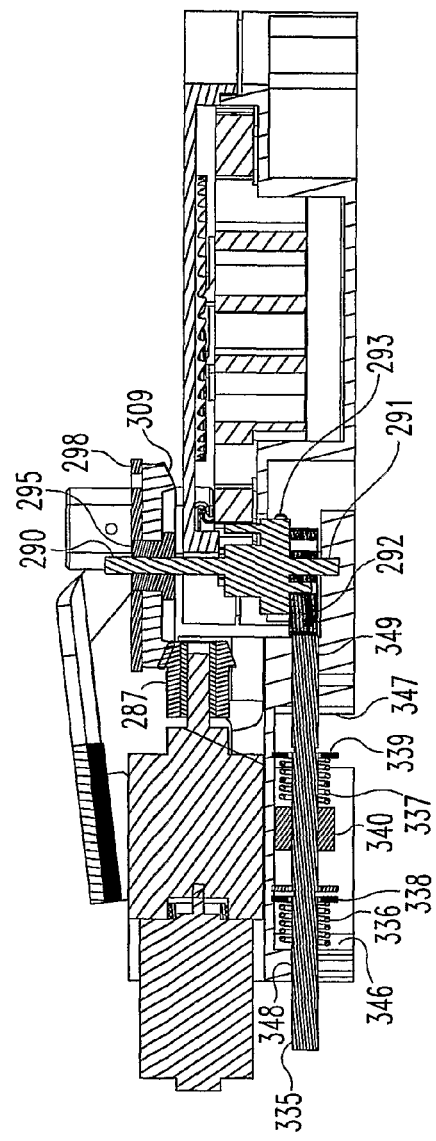
Fig. 35
Fig. 36

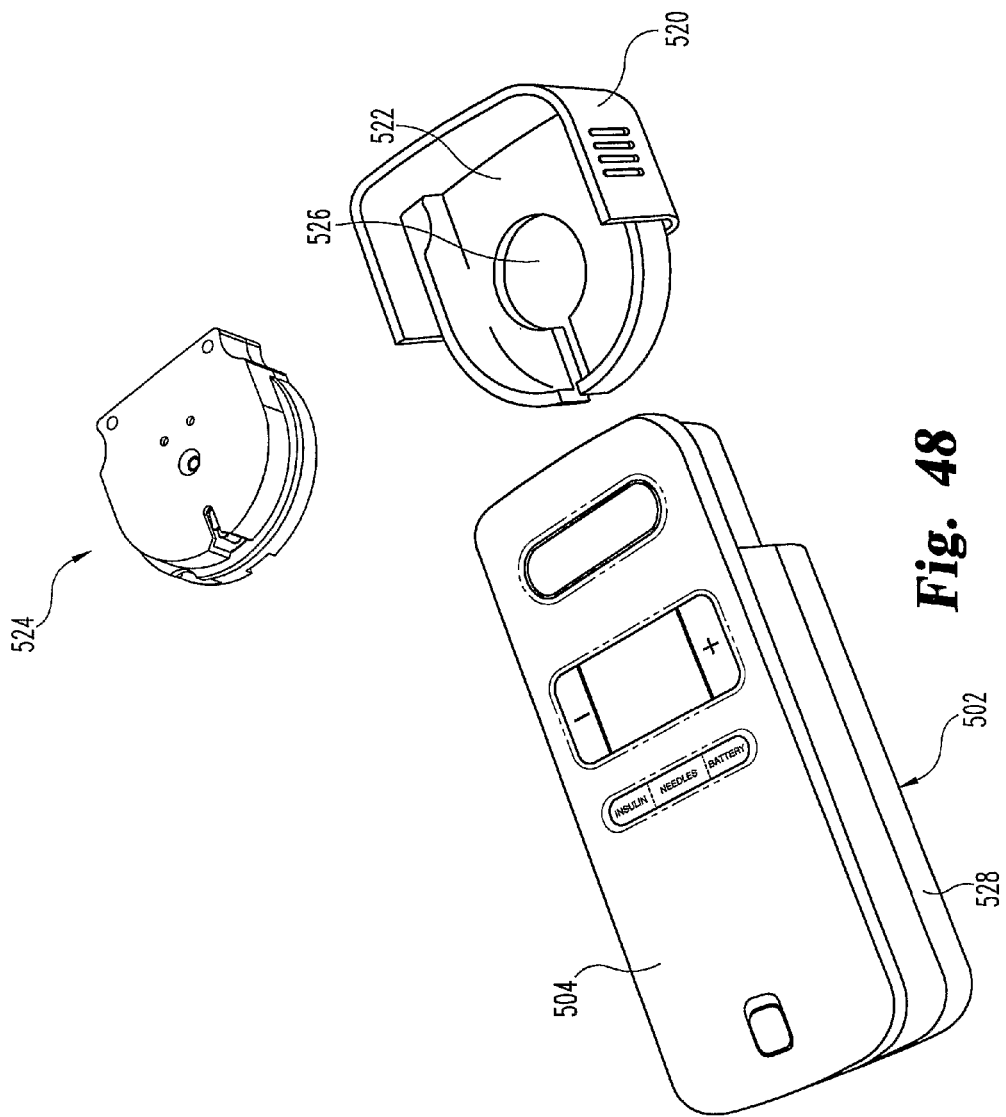

INJECTION APPARATUS HAVING A NEEDLE CASSETTE FOR DELIVERING A PHARMACEUTICAL LIQUID

FIELD OF THE INVENTION

The present invention relates to the field of medical devices, and more specifically, to an apparatus and method for delivering a pharmaceutical liquid to a patient.

BACKGROUND OF THE INVENTION

Delivering a pharmaceutical liquid to a patient by injection is customarily done by needle and syringe. For patients with diabetes, one form of treatment includes insulin shots administered three times each day, just before, at or after mealtime. The development of a wide variety of substantially self-contained pen-type pharmaceutical delivery devices have proven to be a great benefit to the insulin user in simplifying the injection procedure, improving the accuracy of the dosage, lessening the chance of accidental needle sticks, and facilitating proper disposal of used needles, to name a few. However, improvement is continually being sought.

BRIEF SUMMARY OF THE INVENTION

Generally speaking, an apparatus and method are provided for delivering medication to a patient.

An apparatus for delivering a pharmaceutical liquid to a patient includes an outer casing; a needle cassette housed in the casing and containing a plurality of mutually parallel drug injection needles; a drug cartridge housed in the casing, containing the liquid and including a sealable aperture for accessing the liquid; a direct drive assembly housed in the casing and engageable with the drug cartridge to expel a measured dose of the liquid through the aperture; a lifter assembly housed in the casing and engageable with the needle cassette to drive one of the plurality of needles partially out of the casing and into a patient while also accessing the liquid in the drug cartridge through the sealable aperture, and thereafter to withdraw the needle from the patient while halting accessing of the liquid through the sealable aperture after the measured dose of the liquid has been administered through the needle; motor means in the casing for driving the direct drive assembly and the lifter assembly; computer means for activating the direct drive assembly and the lifter assembly; and, a control panel for enabling a user to activate the apparatus.

It is an object of the present invention to provide an improved apparatus and method for delivering a pharmaceutical liquid such as insulin to a patient.

Other objects and advantages of the present invention will become apparent from the following description of the embodiments of the invention.

BRIEF DESCRIPTION OF THE DRAWINGS

FIG. 7 is a perspective view of the drug cartridge 35 of apparatus 10 of FIG. 4.

FIG. 8 is an exploded perspective view of the drug cartridge 35 of FIG. 7.

FIG. 9 is an end view of the drug cartridge 35 of FIG. 7.

FIG. 10 is a side, cross-sectional view of drug cartridge 35 and needle cassette 32 of FIG. 4 taken along the line 10-10, viewed in the direction of the arrows and showing needle assembly 174 in the up, ready position.

FIG. 11 is an enlarged portion of the drug cartridge 35 and needle cassette 32 of FIG. 10.

FIG. 12 is an enlarged portion of the needle cassette 32 of FIG. 10.

FIG. 20 is a perspective view of the direct drive assembly 34 of apparatus 10 of FIG. 4.

FIG. 21 is an exploded perspective view of the direct drive assembly 34 of FIG. 20.

FIG. 22 is an exploded perspective view of the drive nut assembly 123 of direct drive assembly 34 of FIG. 21.

FIG. 23 is a bottom perspective view of the drive nut assembly 123 of FIG. 21.

FIG. 24 is a front view of drive nut 107 of the drive nut assembly 123 of FIG. 21.

FIG. 27 is a perspective view of the needle cassette 32 of apparatus 10 of FIG. 4.

FIG. 28 is an exploded, bottom perspective view of the needle cassette 32 of FIG. 27, and shown with just one needle assembly 174.

FIG. 29 is an exploded, top perspective view of the needle cassette 32 of FIG. 27, and shown with just one needle assembly 174.

FIG. 30 is an exploded, perspective view of a needle assembly 174 of the needle cassette 32 of FIG. 29.

FIG. 35 is a plan view of the needle cassette and lifter assembly of FIG. 34.

FIG. 36 is a side, cross-sectional view of the needle cassette and lifter assembly of FIG. 35 taken along the lines 36-36 and viewed in the direction of the arrows.

FIG. 48 is a perspective view of the apparatus of FIG. 47 with the needle cassette drawer shown disconnected from the remainder of the apparatus, and with a needle cassette shown prior to its insertion into the drawer.

DETAILED DESCRIPTION OF THE INVENTION

Figure 1:
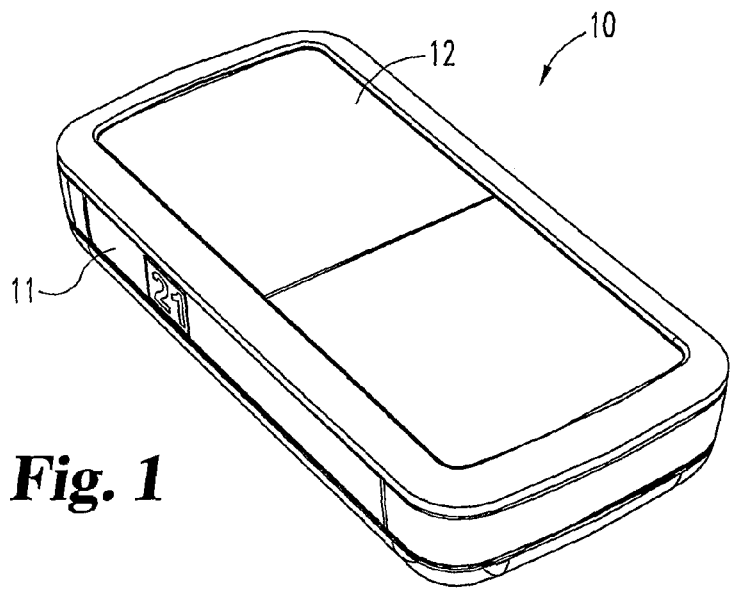
FIG. 1 is a perspective top view of an apparatus 10 for delivering a pharmaceutical liquid to a patient in accordance with one embodiment of the present invention, and with door 12 shown in the closed position.

For the purposes of promoting an understanding of the principles of the invention, reference will now be made to the embodiments illustrated in the drawings and specific language will be used to describe the same. It will nevertheless be understood that no limitation of the scope of the invention is thereby intended, and any alterations or modifications in the illustrated device, and any further applications of the principles of the invention as illustrated therein are contemplated as would normally occur to one skilled in the art to which the invention relates.

Figure 2:
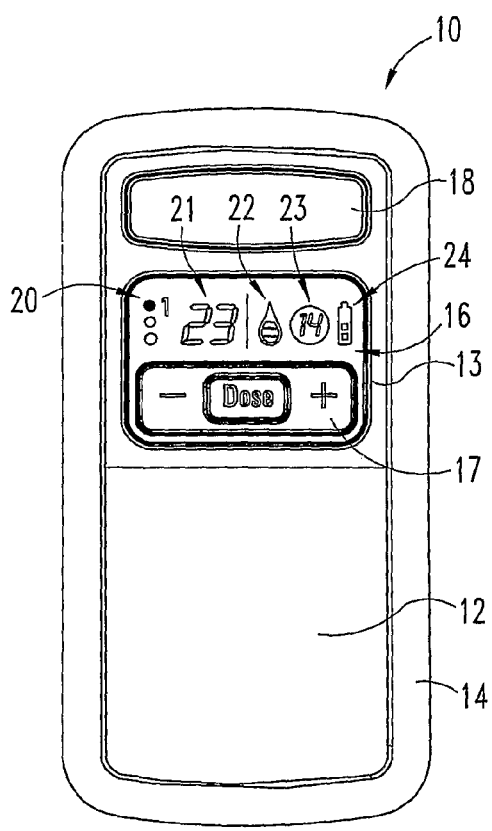
FIG. 2 is a plan view of the top side of the apparatus 10 of FIG. 1, and shown with door 12 in the open position
Figure 3:
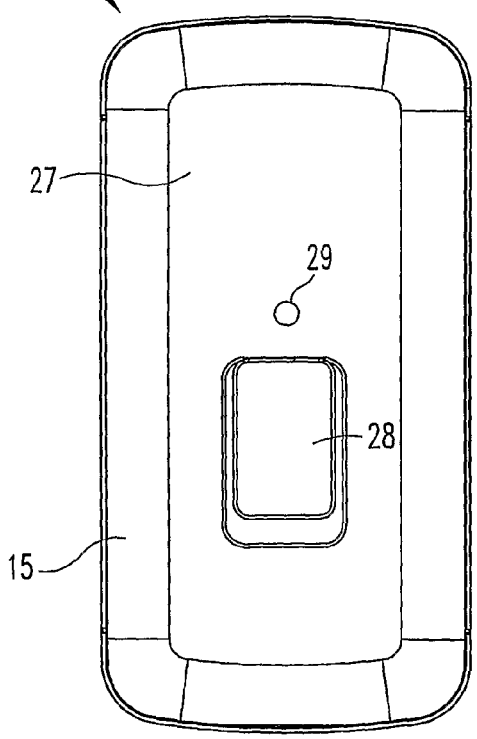
FIG. 3 is a plan view of the bottom side of the apparatus 10 of FIG. 1.

Referring now to FIGS. 1-3, there is shown an apparatus 10 for delivering a pharmaceutical liquid to a patient in accordance with one embodiment of the present invention. Apparatus 10 is designed principally for the delivery of insulin, and description of its various components and manner of operation is therefor made with reference to insulin. It is nevertheless understood that the present invention contemplates use with substantially any desired liquid pharmaceutical. Apparatus 10 includes an outer casing 11 with a door 12 on its top side that can be slid down to an open position (FIG. 2) to reveal a user control panel 13. Outer casing 11 includes top and bottom casing halves 14 and 15, which are hingedly connected to each other along one edge to enable casing 11 to be opened like a book. An appropriate detent or similar mechanism (not shown) holds the casing halves 14 and 15 together. Upon opening casing 11, the user can change batteries, needle cassette or drug cartridge, as described below. In the present embodiment, control panel 13 includes a display section 16, an input pad 17 and an activation button 18. Display section 16 includes a dosage phase indicator 20, dosage unit indicator 21, drug reservoir level 22, remaining needle indicator 23 and battery indicator 24. Display section 16 may comprise any appropriate display panel capable of displaying varying output information. Dosage phase indicator 20 is configured to illuminate one of three numbers: 1, 2 and 3 to signify which of three pre-programmed dosages is next to be administered. In FIG. 2, dosage number 1 is shown illuminated, which could correspond to a first dose of the day or a breakfast timeframe, while dose numbers 2 and 3 could correspond to the second and third dosages such as lunch and dinner timeframes. Alternative configurations are contemplated, such as and without limitation, more or fewer than three dose phases, or displaying one or more mealtime indications, a separate snack indication, a time indication, a date indication, and/or a variable icon indication. Further description of the elements and use of control panel 13 will be described hereinbelow. Alternative embodiments are contemplated wherein control panel 13 is configured in any of a wide variety of different ways to afford the user with operational information and control over the drug administration. For example and without limitation, apparatus 10 is contemplated to include programming and an appropriate connection portal to be connected to an external computer to enable the user to hot-sync with such computer to download the apparatus' operational data (use history, current drug level, battery level, etc.) and to upload new programming. Such new programming might include, for example, a change in dosage level that was received from the user's physician. Apparatus 10 is also contemplated to include wireless capability to enable direct wireless connection with the user's computer or that of the user's physician or pharmacy to download and upload such information.

The bottom side 27 of apparatus 10 includes a portal 28 and an injection opening 29. Portal 28 may be covered with a see-through material such as plastic or glass to enable the user to see the medication. In one embodiment, portal 28 is anticipated to be of a material that absorbs UV light to protect the drug against decomposition. In another embodiment, the portal 28 may comprise an opaque door that may be opened (as by sliding) to allow the non-opaque drug cartridge and its contents to be seen.

Figure 5:
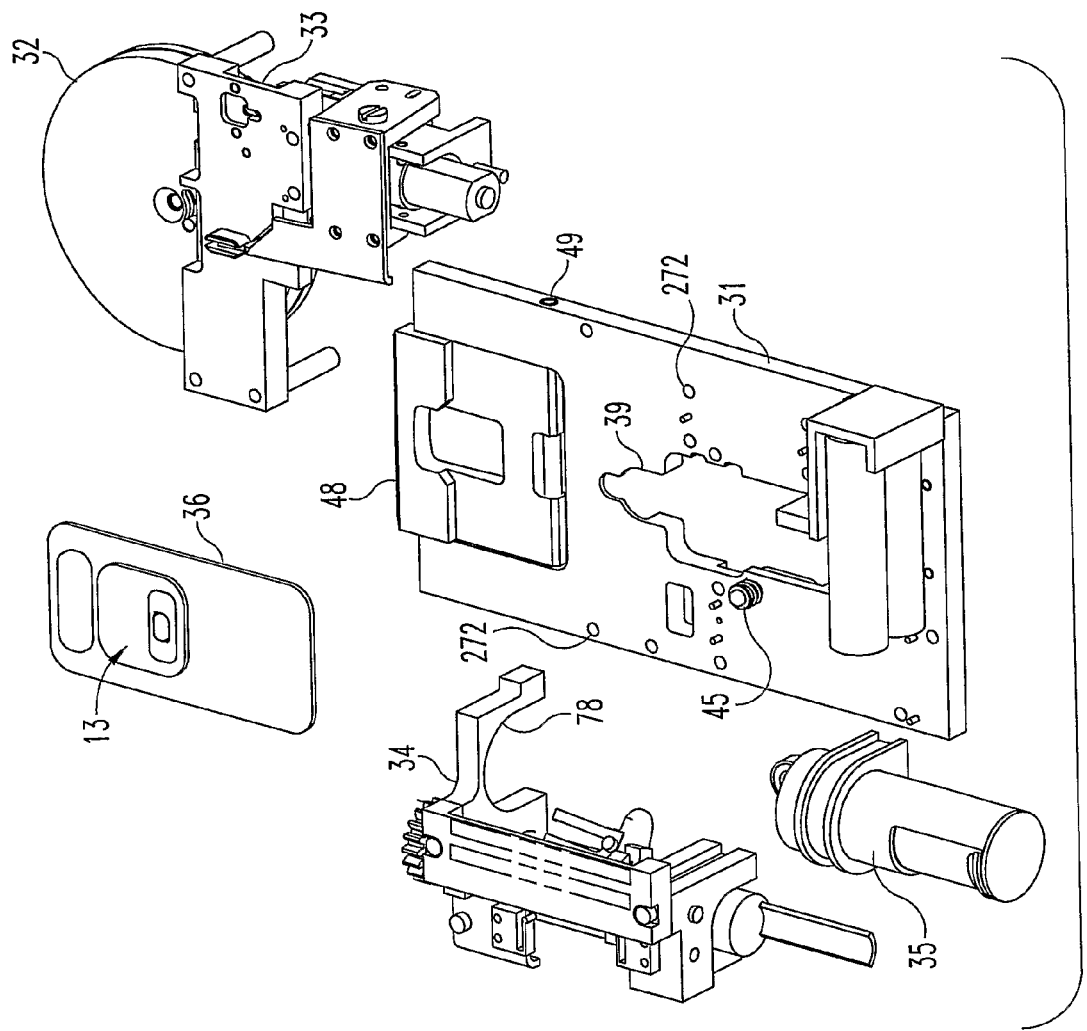
FIG. 5 is an exploded, perspective top view of the apparatus 10 of FIG. 1, and with casing 11 removed for clarity
Figure 4:
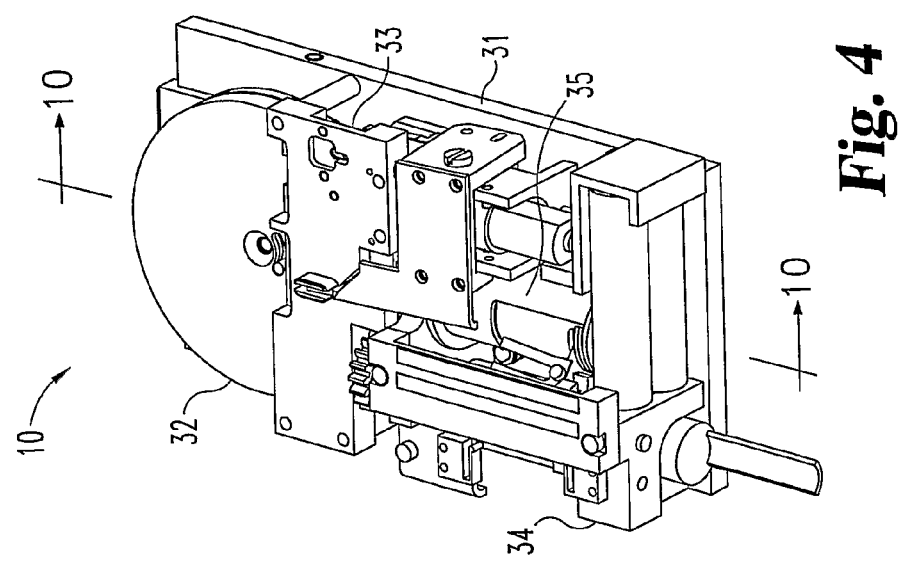
FIG. 4 is a perspective top view of the apparatus 10 of FIG. 1, and with casing 11 and circuit board 36 removed for clarity.
Figure 6:
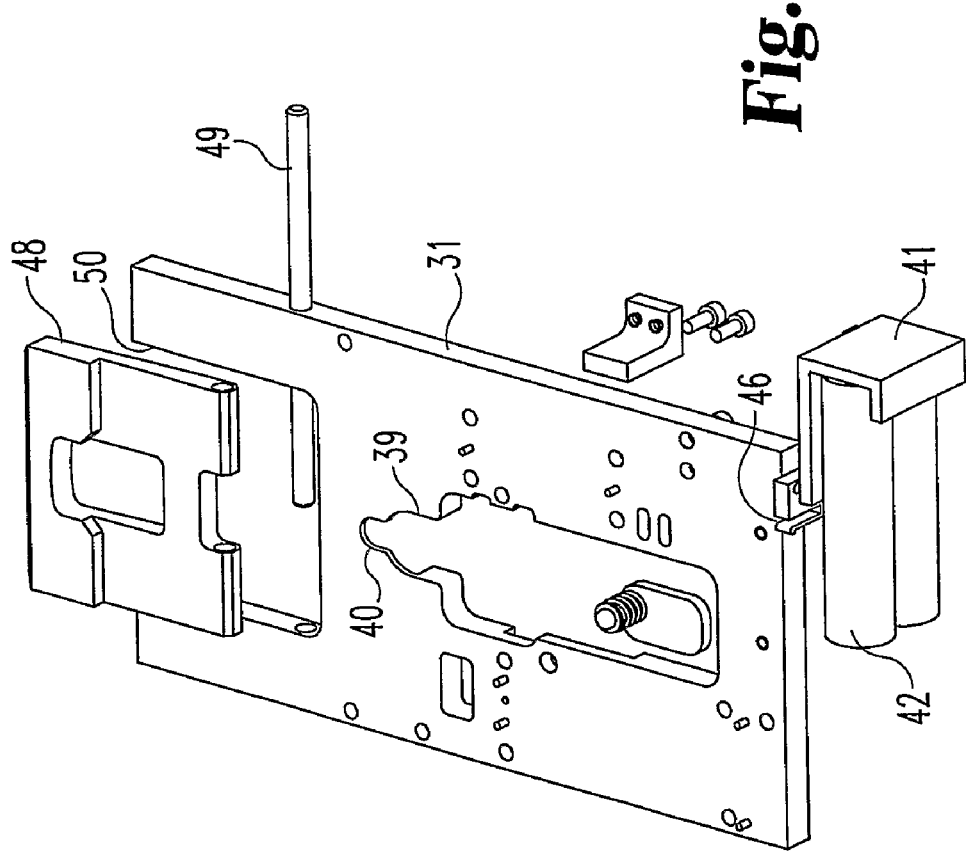
FIG. 6 is an exploded, perspective top view of the base plate 31 of apparatus 10 of FIG. 4.
Figure 13:
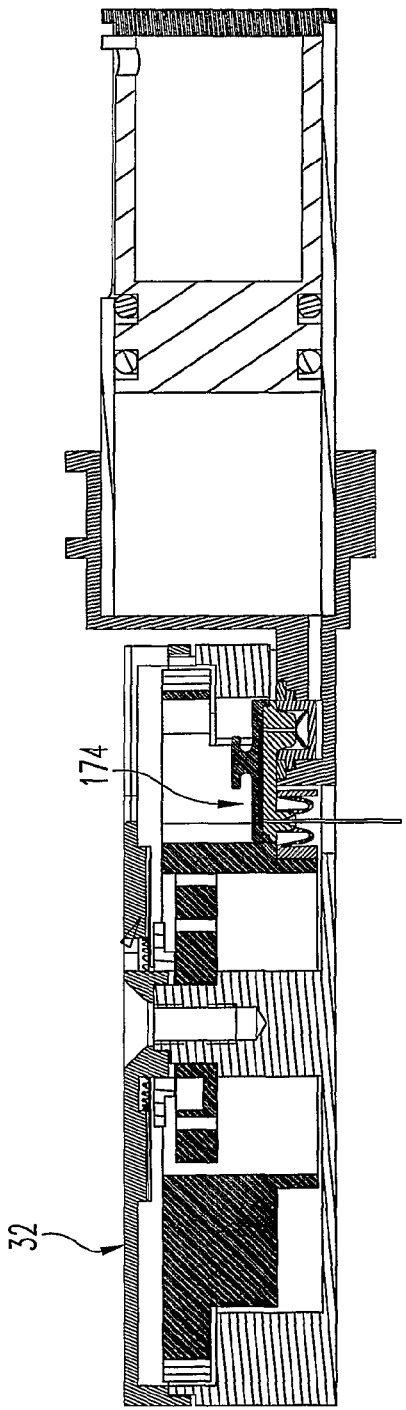
FIG. 13 is a side, cross-sectional view of drug cartridge 35 and needle cassette 32 of FIG. 10 and showing the ready needle assembly 174 in the down, seated position.
Figure 14:
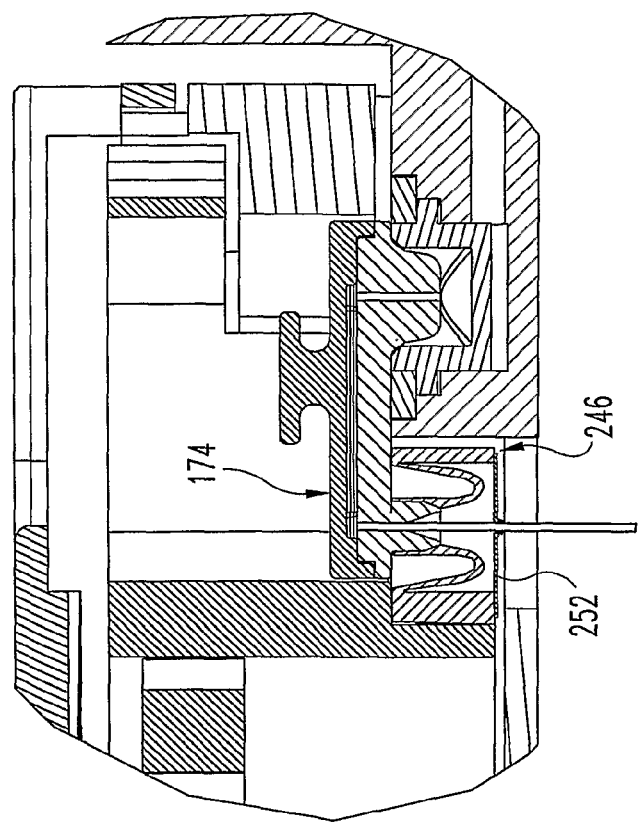
FIG. 14 is an enlarged portion of the drug cartridge 35 and needle cassette 32 of FIG. 13.
Figure 17:
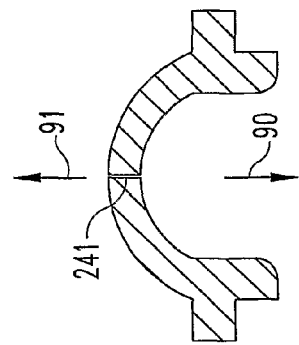
FIG. 17 is a side, cross-sectional view of the valve 87 of FIG. 16 taken along the line 17-17, and viewed in the direction of the arrows.
Figure 18:
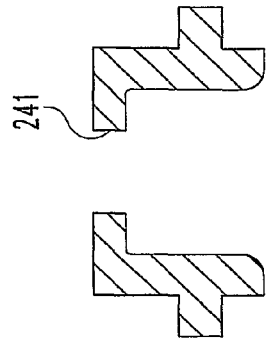
FIG. 18 is a side, cross-sectional view of the valve 87 of FIG. 16 taken along the line 18-18, and viewed in the direction of the arrows.
Figure 15:
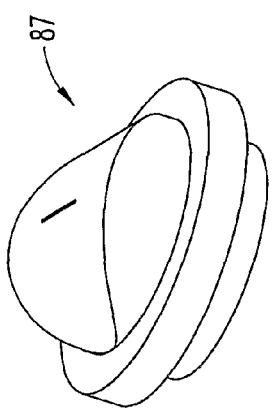
FIG. 15 is a perspective view of the valve 87 of FIG. 8.
Figure 16:
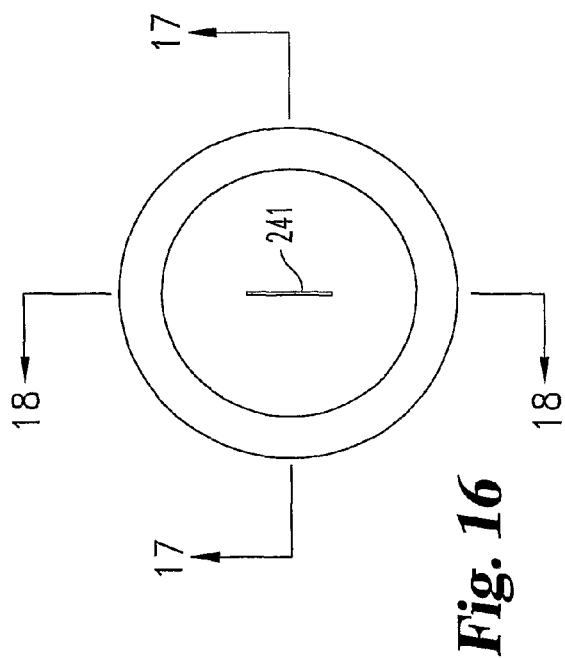
FIG. 16 is a plan view of the valve 87 of FIG. 15.

Referring to FIGS. 4-6, in addition to outer casing 11 (which is removed for discussion of the interior components), apparatus 10 generally includes a base plate 31, a needle cassette 32, a lifter assembly 33, direct drive assembly 34, drug cartridge 35 and circuit board 36. Circuit board 36 includes not only control panel 13, but also appropriate computer chips, memory, connections, etc. to: accept programming; receive, store and process data from the various sensors and control panel; output instructions to the motors; output information to control panel 13 (as desired for various configurations of control panel 13); and, provide outside interactive communication and control (i.e. from a programmer or user). All such circuitry, computer components and connections are contemplated to be mounted on the underside of circuit board 36. Alternative embodiments are contemplated wherein all such circuitry, computer components and connections are carried on any appropriate device, such as and without limitation, a printed circuit board or flex circuit, which would be mounted to the underside of panel 36 or anywhere space permits within outer casing 11. Various elements described herein that receive or produce information or instructions are contemplated to include appropriate connections, though such connections may not be expressly shown or discussed.

Base plate 31 includes a central opening 39 sized to enable insertion of drug cartridge 35 therethrough and into its compartment (which is defined by the other surrounding components that are snugly and precisely packed within outer casing 11). Opening 39 extends forwardly enough (at 40) to enable a needle cannula to pass therethrough, as will be described herein. Connected at its rearward end, base plate 31 includes a battery holder 41 with batteries 42 to power apparatus 10. Alternative embodiments contemplate any suitable power source including, but not limited to rechargeable batteries or power cells. Cartridge support structure 43 is also connected to base plate 31, as needed, to properly seat drug cartridge 35. A latch paddle 44 is pivotally mounted to base plate 31 by a latch pin 45 to enable pivoting latch paddle 44 between an open position (FIG. 5) and a closed position (not shown) pivoted 90 degrees therefrom to firmly engage the underside of a drug cartridge 35 to keep it tightly and securely seated in it its compartment within apparatus 10. A cartridge presence limit switch 46 is mounted to battery holder 41 in a position relative to opening 39 to signal to circuit board 36 when a drug cartridge 35 is being held by apparatus 10. A cassette door 48 is mounted by a door pin 49 to pivotally seat within cassette access opening 50, which is defined in the forward end of base plate 31. Door 48 pivots from its closed position (FIG. 5) to an open position (not shown), which enables a needle cassette 32 to be inserted through access opening 50 and into its compartment (which, like drug cartridge 35, is defined by the other adjacent components that are snugly and precisely packed within outer casing 11). Alternative embodiments are contemplated wherein casing 11 and the other components of apparatus 10 are structured to enable the arrangement of, and access to, batteries 42, needle cassette 32 and drug cartridge 35 to be changed in a variety of different ways. For example and without limitation, a door at the rearward end of casing 11 would permit axial insertion and withdrawal of batteries 42.

Referring to FIGS. 4 and 7-13, drug cartridge 35 generally includes a cartridge housing 53, a plunger 54, a head cap 55 and a base cap 56. Housing 53 is generally a cylindrical tube with a portion cut away through about 100° to define a slide window 57. Window 57 is thus defined by opposing straight edges 61 and 62 and connecting front edge 63. Plunger 54 is sized and configured to be received for telescopic movement within housing 53. A pair of seals 64 seat within grooves 65 to provide a fluid tight seal between plunger 54 and housing 53. At its back end, a guide flange 67 extends radially outwardly with flange 67 defining a pair of opposing nicks 68 and 69, which register with the opposing edges 61 and 62 of slide window 57 to guide plunger 54 in a straight, non-rotational path within housing 53. The forwardmost limit of travel of plunger 54 is defined when and if the forward face 71 of plunger 54 contacts the inside end face 72 of head cap 55. Plunger 54 further defines an arcuate guide recess 70 just forward of guide flange 67, as shown. Once plunger 54 is firmly received within housing 53, rear end cap 56 is tightly received at the rear end of housing 53, as shown.

Head cap 55 has a central opening 73 sized to tightly receive housing 53, as shown. Housing 53 is securely bonded to head cap 55. Alternatively, head cap 55 and housing 53 can be formed as a single, homogeneous unit. Housing 53, head cap 55 and plunger 54 together define drug chamber 74. Head cap 55 includes a pair of upstanding ridges 75 and 76 that together define an outer channel 77, which is configured to seat within a complementary-shaped arch 78 of direct drive assembly 34. The bottom surface 79 of head cap 55 is flat and seats against the bottom half 15 of outer casing 11, in assembly.

Figure 19:
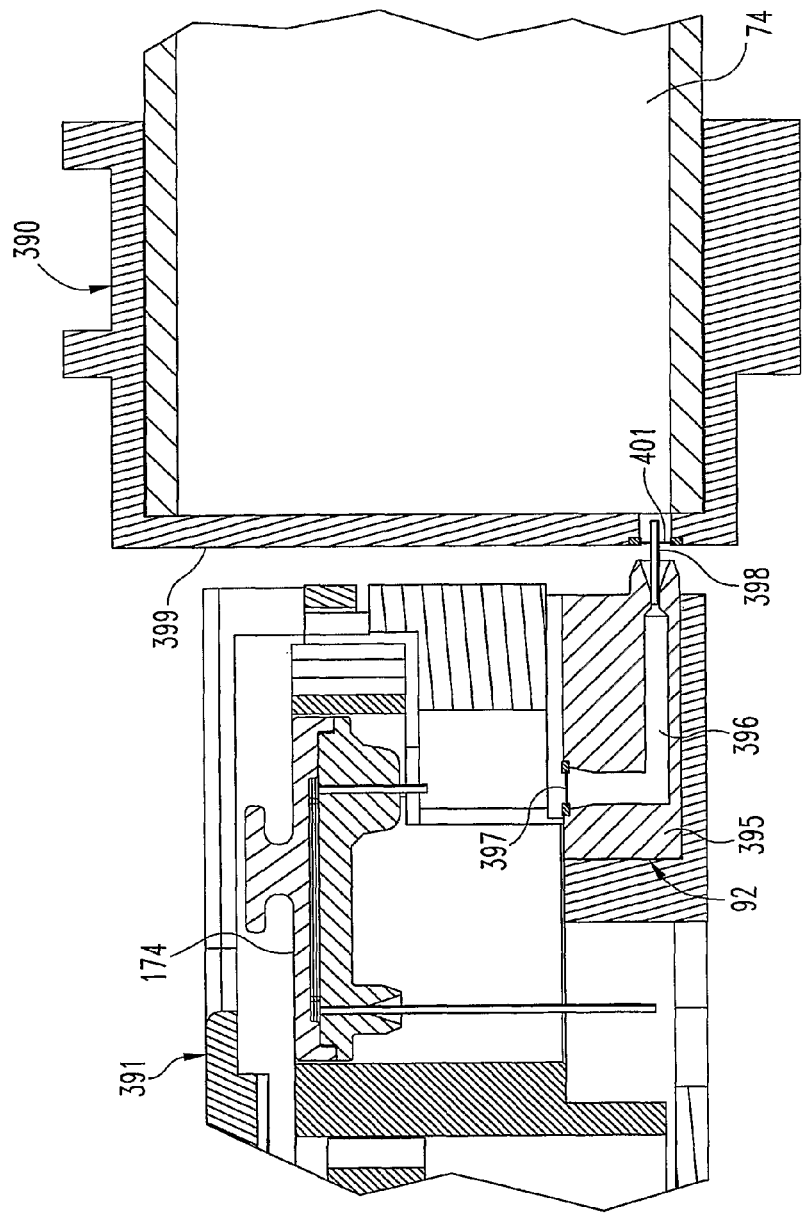
FIG. 19 is a side, cross-sectional view of drug cartridge 35 and needle cassette 32 of FIG. 4 showing a valve assembly 92 in accordance with another embodiment of the present invention.
Figure 25:
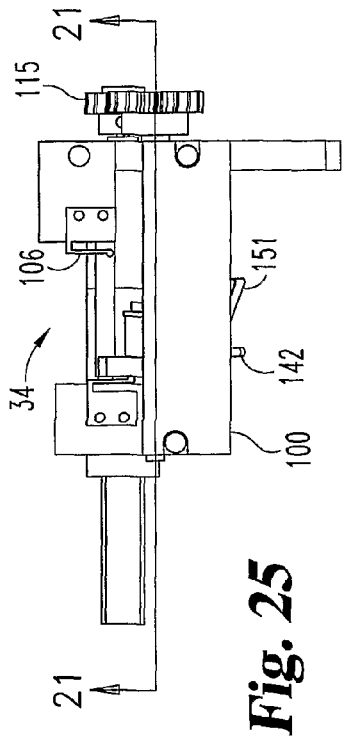
FIG. 25 is a top view of the direct drive assembly 34 of FIG. 20.
Figure 26:
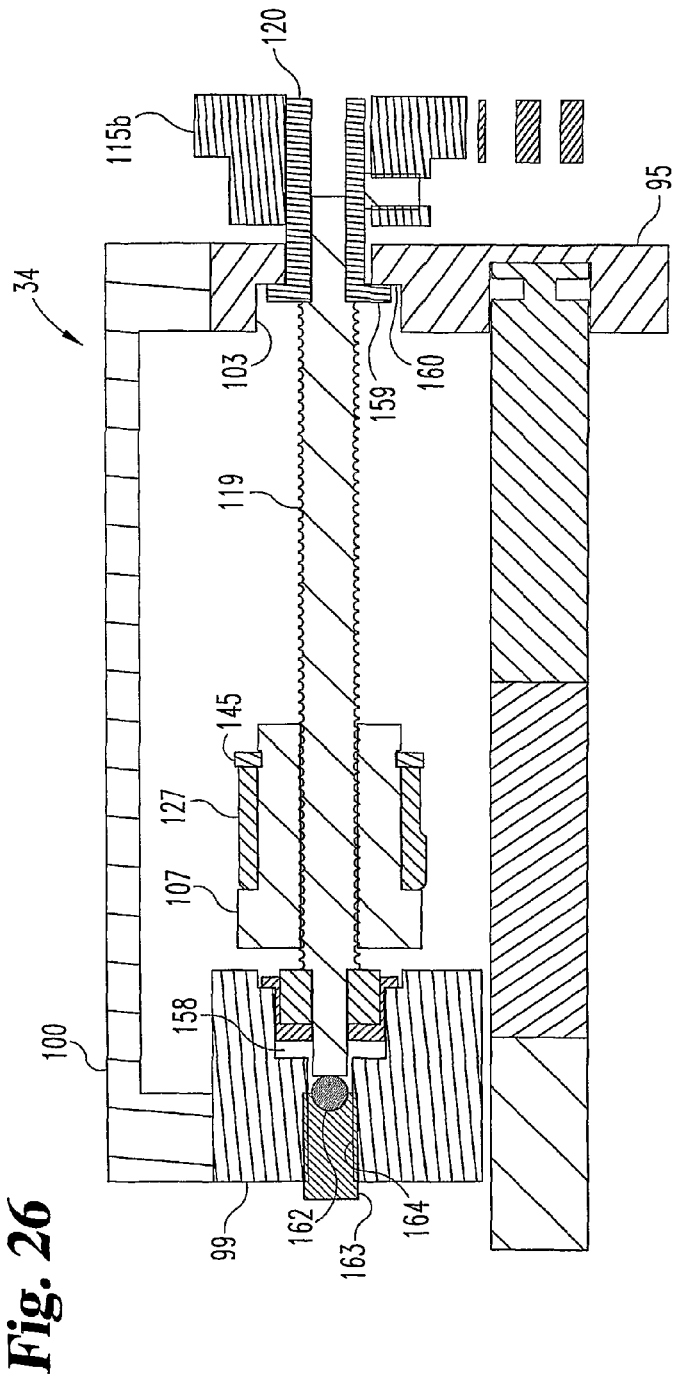
FIG. 26 is an enlarged side, cross-sectional view of the direct drive assembly 34 of FIG. 25 taken along the lines 26-26 and viewed in the direction of the arrows.
Figure 31:
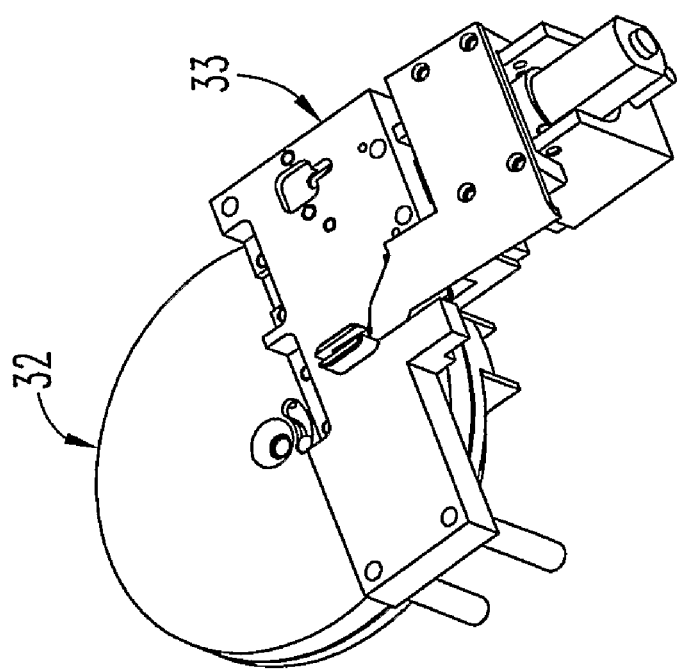
FIG. 31 is a perspective view of needle cassette 32 in engagement with lifter assembly 33 of FIG. 4.

Head cap 55 also includes a forwardly extending valve shelf 82. Shelf 82 includes a hole 83 with circumferential ledges 84 and 85. A bi-directional valve 87 seats within the inner ledge 84, and a retaining ring 88 seats within the upper and outer ledge 85 to securely hold valve 87 in its ledge 84. Shelf 82 further defines a passageway 89 extending between hole 83 and drug chamber 74. As shown in FIGS. 15-18, and discussed in greater detail herein, bi-directional valve 87 is designed to permit flow in one direction (the "fill" direction, 90 into drug chamber 74) under little pressure (e.g. 1 psi), to prevent flow in the opposite direction (the "outflow" direction 91, out of drug chamber 74) up to a transition pressure (e.g. 30 psi), and to permit flow in the outflow direction 91 so long as the transition pressure is exceeded in that direction. Thus, flow of drug from chamber 74 out through valve 87 only occurs when plunger 54 is advanced (to the left in FIG. 10) with sufficient force to cause the fluid pressure in chamber 74 to exceed the transition pressure. In one embodiment, the transition pressure is between about 25 psi and 30 psi, although this value may be adjusted as desired to optimize operation of apparatus 10. In one embodiment, engagement with and deformation of the top of valve 87 by a fill port decreases the transition pressure needed to permit outward flow. Thus, a transition pressure without deformation of the top of valve 87 may be 45 psi, but with contact pressure from a fill port, and possible deformation therefrom, such transition pressure may drop to 25 psi. Alternative embodiments of shelf 82 contemplate a septum or similar structure in place of valve 87, wherein access to the drug in chamber 74 is achieved by a needle piercing the septum. For example and without limitation, referring to FIG. 19, there is shown a valve assembly 92 for completing the fluid path between needle assembly 174 and drug chamber 74 in accordance with an alternative embodiment of the present invention. As described herein, valve assembly 92 includes a valve block 395 with septum and needle pairs to replace the bi-directional valve 87 arrangement of FIG. 10.

Referring to FIGS. 5 and 20-26, the direct drive assembly 34 for advancing plunger 54 within its housing 53 is shown. Direct drive assembly 34 generally includes a frame assembly 95, a motor assembly 96 and a screw drive assembly 97. Frame assembly 95 includes a front frame member 98, a rear frame member 99, a sensor plank 100 and a guide rod 101. Front frame member 98 defines the arch 78 into which is seated head cap 55 of drug cartridge 35. Front frame member 98 also defines holes 102 and 103 for receipt of the front ends of motor assembly 96 and screw drive assembly 97, respectively. The front end of motor assembly 96 is positioned within hole 102 and is secured thereat by appropriate means such as a set screw 94. Front frame member 98 also includes a limit bracket 104 secured thereto by screw 105, and limit bracket 104 includes a front limit sensor 106 that sends a signal upon being contacted by drive nut 107 of screw drive assembly 97, as described herein. The rear end of motor assembly 96 is seated in an arch 108 defined by rear frame member 99 and is clamped snugly therein between rear frame member 99 and base plate 31. Rear frame member 99 includes a back limit sensor 109 that sends a signal upon being contacted by drive nut 107, as described herein. Motor assembly 96 includes a motor 110, a gear head 111 and an encoder 112, all connected together as a single unit. Ribbon cable 114 extends from motor assembly 96 and connects with batteries 42 to provide power and connects with circuit board 36 to provide and receive information and operating instructions. Forwardly of front frame member 98, a gear 115a is connected to the output shaft 116 of motor assembly 96. Gear 115a meshes with a gear 115b that is connected to front bearing 120 to transmit power to screw drive assembly 97. Guide rod 101 extends through holes 117 and 118 in front and rear frame members respectively.

Screw drive assembly 97 includes a threaded shaft 119, a front bearing 120, a rear bearing 121, an adaptor 122 and a drive nut assembly 123. (In the present embodiment, adaptor 122 is used solely to properly mount bearing 121 with rear frame member 99. In alternative embodiments, bearing 121 is sized and shaped to properly mate with rear frame member 99 without use of an adaptor 122). Drive nut assembly 123 (FIGS. 21-23) generally includes drive nut 107, a nut flange 127 and a sensor lead 128. Drive nut 107 includes a central hub 129 and a backplate 130. Central hub 129 has a central, internally threaded bore 132, and drive nut 107 is thus threadedly received on threaded shaft 119 for axial movement thereon as shaft 119 is rotated. Backplate 130 extends laterally from the axis of hub 129 and defines at one end thereof an outwardly opening slot 133. On its forward side 135, back plate 130 defines an arcuate groove 136, and on the opposite side of hub 129 therefrom, a hole 137.

Nut flange 127 includes a sleeve 140 and an arm 141 extending radially therefrom. The outboard end of arm 141 defines a rounded fin 142 that is sized and configured to drop into and engage with guide recess 70 of plunger 54. Sleeve 140 defines a central hole 143 that is sized to coaxially receive central hub 129 and permit nut flange 127 to rotate freely about central hub 129. Rotation of nut flange 127 relative to drive nut 107 is limited to about 40°, however, by a pin 144 extending rearwardly from arm 141, the outboard end of which rides within groove 136 of drive nut 107. Nut flange 127 is held in position over central hub 129 by a retaining ring 145 that is received in a circumferential groove 146 defined at the forward end of hub 129. A coil spring (not shown) encircles sleeve 140 with the ends of such spring seated in holes 147 and 148 of nut flange 127 and drive nut 107, respectively, to bias nut flange 127 to its counterclockwise extreme (as viewed in FIG. 23) relative to drive nut 107. Nut flange 127 can thus be rotated about 40° (clockwise in FIG. 13, counterclockwise or up as viewed in FIG. 21), but it is biased to rotate to its down position, as shown in FIG. 21.

Sensor lead 128 is a metallic conductive element with a base 149 that is secured to the top of nut flange 127 by screws 150. A pair of contact arms 151 and 152 extend upwardly from base 149 and are spaced and dimensioned to engage and complete a circuit with contact strips 153 and 154, which are fixed to the underside of sensor plank 100 and are electronically connected (as by wires, not shown) to circuit board 36. Rotation of nut flange 127 upwardly, whereupon contact arms 151 and 152 engage contact strips 153 and 154, signals to circuit board 36 that nut flange 127 is in the up position and, as described below, that a new drug cartridge has just been inserted. Alternative embodiments are contemplated wherein the angular position of nut flange 127 is detected by any other appropriate structure such as, and without limitation, a rotary encoder, an optical sensor, or any variety of mechanically engaging sensing elements. In operation, upon sensing that a drug cartridge 35 has been inserted, whether such cartridge is full or less than full, apparatus 10 activates direct drive assembly 34 to engage with such cartridge 35, or rather the plunger 55 of the inserted cartridge 35, regardless of its position, to ready it for instant drug delivery injection. More specifically, if cartridge 35 is removed from apparatus 10, the signals (or lack of signals) from cartridge presence limit switch 46 (FIG. 6) and sensor lead 128 is interpreted by circuit board 36 as a no drug cartridge event, and circuit board 36 signals motor assembly 96 to turn threaded shaft 119 (through gears 115a and 115b), which advances nut assembly 123 forward until the backplate 130 of nut assembly 123 engages and triggers limit switch 106, whereupon motor assembly 96 is directed to stop, and apparatus 10 waits in this position until a drug cartridge 35 is inserted. When a drug cartridge 35 is inserted, positive signals from cartridge presence limit switch 46 and sensor lead 128 are received and interpreted by circuit board 36, which activates motor assembly 96 to move nut assembly 123 backwards, whereby nut flange fin 142 drags along drug cartridge 35 until fin 142 falls into guide recess 70, whereupon sensor lead 128 falls away from contact strips 153 and 154 just enough for circuit board 36 to sense this and to stop motor assembly 96. With a drug cartridge in place, the programming of apparatus 10 then directs performance of a compliance check (if so programmed) or simply updates its internal registers that apparatus 10 is ready to deliver its drug.

Should the user need more doses (for a trip, for example) than are then in his apparatus 10, the foregoing configuration and operation enables the user to easily and quickly remove a partially used drug cartridge 35 and to insert a full or fuller cartridge 35.

Referring to FIGS. 20, 21, 25 and 26, bronze bearings 120 and 121 are securely connected at opposing ends of threaded shaft 119, and bearings 120 and 121 are supported for rotation within hole 103 of front frame member 98 and hole 158 in rear frame member 99, respectively. A flange 159 at the rear of front bearing 120 bears against the ledge 160 created between large and small diameter portions of hole 103, which provides forward thrust support for shaft 119 when drive nut assembly 123 is moved rearwardly. In contrast to the little resistance to rearward movement of drive nut assembly 123, forward movement of drive nut assembly 123 is usually associated with the advancement of plunger 54 to expel medication from drug cartridge 35. Rearward thrust support for such increased force is provided by a ball bearing 162 and set screw 163 that are seated within a threaded hole 164, which is in communication with the hole 158 in which rear bearing 121 is seated. Ball bearing 162 bears against the rear end of threaded shaft 119, and set screw 163, which has a cupped forward end for receipt of ball bearing 162, may be adjusted to properly set the position of shaft 119. Although assembly 34 is referred to as a "direct" drive assembly, such assembly may be of any configuration, direct, indirect or otherwise so long as it causes drug in a drug cartridge or container to be expelled from such container and ultimately through a needle into the patient.

Referring now to FIGS. 10-14 and 27-30, needle cassette 32 generally includes a housing bottom 169, a shroud array 170, a cassette body 171, a lockring 172, a lid 173 and a plurality of needle assemblies (only one shown at 174). Housing bottom 169 is generally circular with a floor 177, a cylindrical wall 178 that transitions into an annular ledge 179 and then back to an upper cylindrical wall 180. Extending upwardly from the center of floor 177 is a central post 182 that includes a ledge 183. A small pair of fins 184 and 185 extend outwardly from wall 178, below ledge 179. The gap created between fins 184 and 185 is sized to receive the leading end of valve shelf 82 of drug cartridge 35. Fins 184 and 185 also engage with other similarly configured structure (not shown) in apparatus 10 to ensure proper insertion and positionment of needle cassette 32 within casing 11. A hole 186, defined in floor 177, is sized and positioned (in radial alignment with fins 184 and 185) to enable a needle to extend therethrough upon activation of apparatus 10. Likewise, cylindrical wall 178 defines a recess 187 sized and positioned to enable a needle assembly 174 to extend downwardly during activation of apparatus 10. As described herein, the needle assembly 174 is extended downwardly and subsequently retracted through hole 186 and slot 187 (after injection is complete) via spring mechanisms that are charged by a single motor. Upper cylindrical wall 180 also defines a recess 188 sized to enable a geneva wheel 191 to engage with the outer edge of cassette body 171, as described herein.

Cassette body 171 is a plastic geneva disc with a central indexing section 192 and an outer slot section 193. In slot section 193 there are defined a plurality of needle assembly slots 194. In the present embodiment, needle cassette 171 provides a one week needle supply in that cassette body 171 defines 21, angularly spaced needle assembly slots 194, which correspond to three injections per day of insulin, one corresponding to each of three meals, times seven days per week. Slots 194 are mutually identical, have an ovate shape and extend all the way through cassette body 171. Slots 194 (and the mating needle assemblies 174) may be of any desired shape, although non-round is preferred to prevent rotation of the needle assembly 174 within the slot 194. In addition, the ovate shape maximizes the area for each needle assembly 174. That is, the ovate shape corresponds to the roughly 17.14° pie wedge allotment for each of the 21 slots (360°/21 slots). At its center, cassette body 171 defines a hole 196 sized to receive the upper, smaller diameter section 197 of central post 182 therethrough, whereby cassette body 171 rests and can rotate atop ledge 183. Smaller diameter section 197 (FIG. 12) defines a flattened recess (at 198), which registers with a complementary shaped, central hole 199 defined in a circular post 200 that extends downwardly from the center of lid 173. Lid 173 is thus received on post 182 and housing bottom 169 in only one orientation, as shown. In that orientation, a radial plunger slot 202 defined in lid 173 aligns directly over hole 186 and recess 187 of housing bottom 169. Lid 173 defines a central hole 203, and post 182 defines a threaded hole 204. An appropriate fastener such as a screw (not shown) extends through holes 203 and 204 to securely connect lid 173 to post 182. For maximum safety and security, it is desired that lid 173 be connected to housing bottom 169 with any appropriate means that discourages or prevents the user from accessing the cassette body 171 or needle assemblies 174 housed therein. Examples of such means would include, without limitation, proprietary headed screws, glue, a snap fit and ultrasonic welding. Lid 173 also defines an arcuate slot 205 located proximal to central hole 203. On the underside of lid 173 and surrounding central post 200 are defined a series of lightly sloped ramps 209 that extend radially outwardly.

Central indexing section 192 of cassette body 171 includes a pair of opposing, cantilevered arms 210, each with a barb 211 extending upwardly from the outboard end thereof. With needle cassette 32 fully assembled and lid 173 secured to housing bottom 169, barbs 211 engage with ramps 209 on the underside of lid 173 to limit cassette body 171 for rotation in only one direction—counterclockwise, as viewed in FIG. 29, relative to lid 173.

Located between cantilevered arms 210 and central hole 196, central indexing section 192 defines a lockring follower groove 213. Groove 213 extends through approximately 320° of a circle. Lockring 172 is an annular disc, also with a pair of opposing, cantilevered arms 214, each with a barb 215 extending upwardly from the outboard end thereof. Lockring 172 also has a central hole 216 and a post 217 that extends both above and below lockring 172, as shown. In assembly, lockring 172 sits between cassette body 171 and lid 173, with post 200 of lid 173 extending coaxially through hole 216, and with lockring post 217 extending down into groove 213 of cassette body 171 and up into arcuate slot 205 of lid 173. With lid 173 thus secured to housing bottom 169, barbs 215 engage with ramps 209 on the underside of lid 173 to bias lockring 172 against rotation as cassette body 171 rotates beneath it, and as post 217 follows in groove 213. Through this phase, the upper portion of post 217 remains at one end (the clockwisemost end) of arcuate slot 205, as seen in FIG. 27. But when cassette body 171 has rotated through most of its needle assemblies 174 (e.g. through the first 18 of 21), post 217 will have reached the clockwise-most end 220 of groove 213. Any further rotation of cassette body 171 will force lockring 172 to rotate counterclockwise, with cassette body 171 and against the resistance existing between barbs 215 and ramps 209 208. (It is noted that the configuration of cantilevered arms 214 and barbs 215 prevents lockring 172 from rotating clockwise relative to lid 173.) It is important that the user know when his needle supply is close to running out. Thus, as cassette body 171 is rotated through its last needle assemblies 174 (e.g. $19^{th}$, $20^{th}$ and $21^{st}$ needles), post 217 moves in arcuate slot 205 from the clockwise-most home position 221, three successive places counterclockwise until it reaches the opposite, counterclockwise-most end position 222. At this point, cassette body 171 is physically prevented from further rotation as post 217 is at the counterclockwise extreme end position 222 of arcuate slot 205 and at the clockwise extreme end 220 of groove 213.

Figure 33:
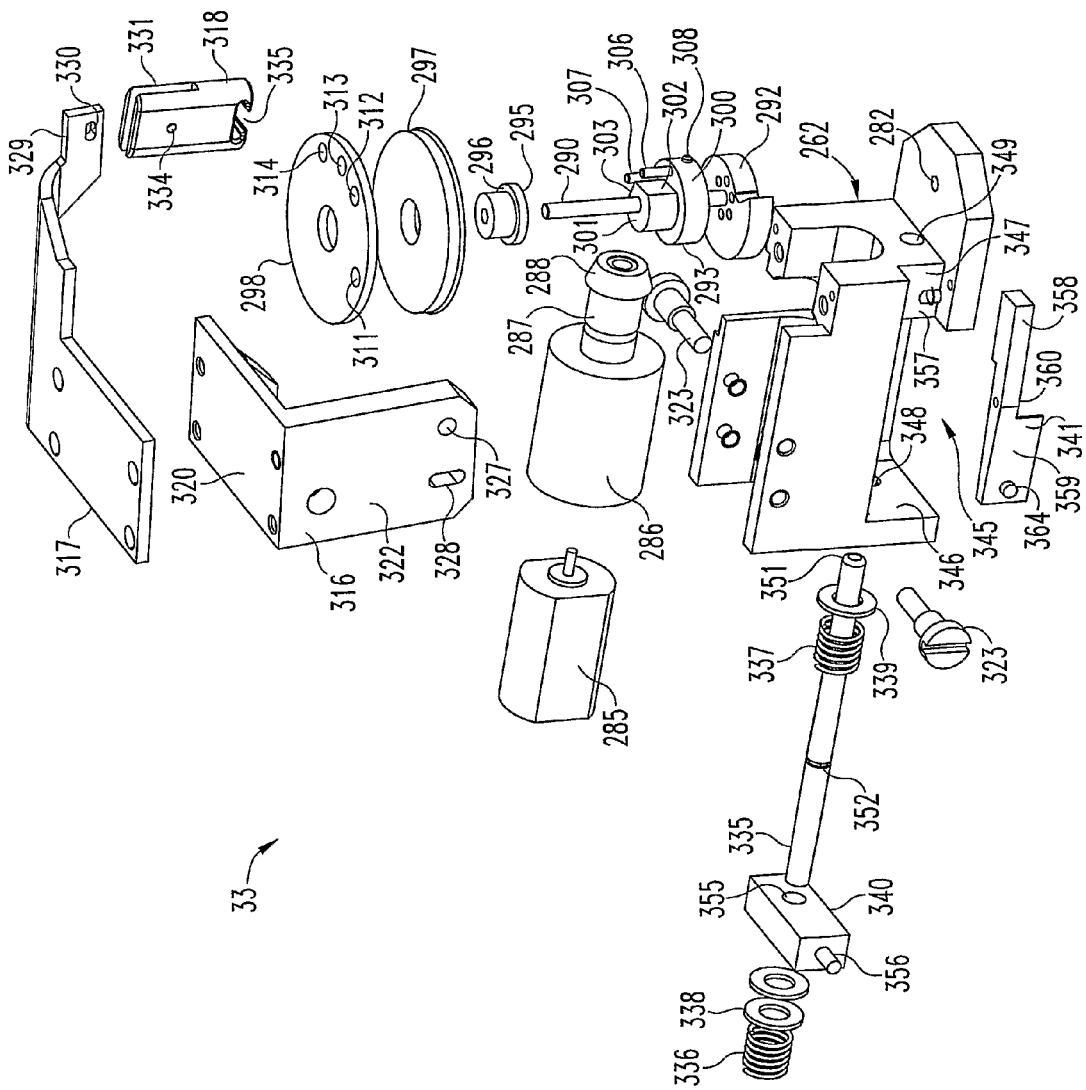
FIG. 33 is an exploded, perspective view of the lifter assembly 33 of FIG. 31.

As described herein, cassette body 171 is a double geneva disc defining 42 (as opposed to 21) vertical indexing grooves 225 evenly spaced along the circumferential edge 226, which enables indexing in half increments. That is, there are 21 needle assembly slots 194, which provides for about 17.14° per slot 194 (360°/21). Each full index of cassette body 171 is thus about 17.14°. As described herein, the double geneva assembly used herein permits a half index by engaging just one pin on geneva 293 (FIG. 33). When apparatus 10 is at rest between injections, and after the last needle assembly has been used, the cassette body 171 is automatically indexed to the needle cassette "safe position", which is one half index farther past a needle assembly ready position. In the needle index safe position the portion of cassette body 171 that is exposed, through radial plunger slot 202, is the region or "land" 228 between two adjacent needle assembly slots 194, rather than directly over a slot 194. The sizing and positionment of groove 213 and slot 205 are specifically sized and configured to create the safe position. With each needle assembly 174 thus being one half advancement away from alignment with the upper and lower openings 202 and 186, needle cassette 32 can be removed from apparatus 10 without concern that a needle will engage and damage flow valve 87 or the user. A user going on a four day trip, for example, (needing 4×3, or 12 injections) may find that she has only five remaining unused needles). With needle cassette 32 always being in the safe position during the rest position of apparatus 10, such user can safely replace the nearly empty needle cassette 32 with one that is full or has at least 12 remaining unused needles. Another consequence of such automatic positionment in the safe position is that needle cassettes 32 are self-contained disposal units and need no additional container to safely enclose the used needles—they are already enclosed in a securely closed housing and ready for disposal.

Referring to FIGS. 10, 11, 14 and 30, needle assembly 174 includes a needle hub 230, a needle cap 231 and a needle cannula 232. From opposite ends of its main body, hub 230 has a downwardly extending post 233 and a downwardly extending valve probe 234. A vertical passageway 237 extends all the way through post 233 and a vertical passageway 238 extends all the way through valve probe 234. Needle cannula 232 is fixed in passageway 237 to extend downwardly therefrom, as shown. A glue reservoir 239 is provided for the adhesive to fix cannula 232 to hub 230. When in the "ready" position, needle assembly 174 is still fully seated in its up position within cassette body 171, and cannula 232 extends downwardly to just above hole 186. Hole 186 is preferably large enough to permit easy passage of cannula 232 therethrough, but not large enough for a person to stick a finger therethrough.

Valve probe 234 is shaped generally as shown with a smooth, flattened face 240, and is configured so that its passageway 238 is aligned with slit 241 of valve 87. When needle assembly 174 is forced down from its up, ready position (FIGS. 10 and 11) to its down, seated position (FIGS. 13 and 14), valve probe 234 engages valve 87 under sufficient pressure (e.g. about 25 psi) to deform valve 87 sufficiently to cause a separation at its central slit 241 and to form a seal therewith. Fluid from drug chamber 74 is permitted to flow freely in the outflow direction 91 through slit 241 and into passageway 238. Valve 87 may be made in a variety of shapes to accomplish this action, with the valve 87 of FIGS. 15-18 being one preferred construction. Valve 87 is made of any suitable material for a self sealing valve as described herein.

The bottom of needle cap 231 has a complementary shape to that of the top of needle hub 230 so that hub 230 and cap 231 can be fixedly bonded together in the configuration shown in FIG. 11, except that the bottom of cap 231 has a small lateral channel 242 defined therein. When hub 230 and cap 231 are mated together as shown, hub 230 and cap 231 turn channel 242 into a fluid tight passageway that extends between vertical passageways 237 and 238, which thereby completes the fluid path from valve 87, through passageway 238, channel 242, and passageway 237 and into cannula 232. At its top, needle cap 231 includes an upstanding T-bar 243, shaped for engagement with lifter assembly 33.

Referring to FIGS. 11, 14, 28 and 29, shroud array 170 is a homogeneously formed, silicone ring with 21 upstanding, inverted-funnel-like shrouds 246. Each shroud 246 is tapered and has a top that is tightly fitted over needle post 233 to move as a unit therewith. The bottom end of each shroud transitions through a thinner, more flexible membrane section 247 into the ring-like base 248. Shroud array 170 protects each needle cannula 232 prior to use and thereafter. In addition, a paper or similarly composed, annular-shaped seal disc 252 is adhesively affixed to the bottom of shroud array 170 to further protect against contaminants from entering an individual shroud 246 and, more importantly, its cannula 232. In use, when needle assembly 170 is forced down, cannula 232 easily pierces seal disc 252 (FIG. 14) and passes through hole 186 in cassette floor 177.

Figure 43:
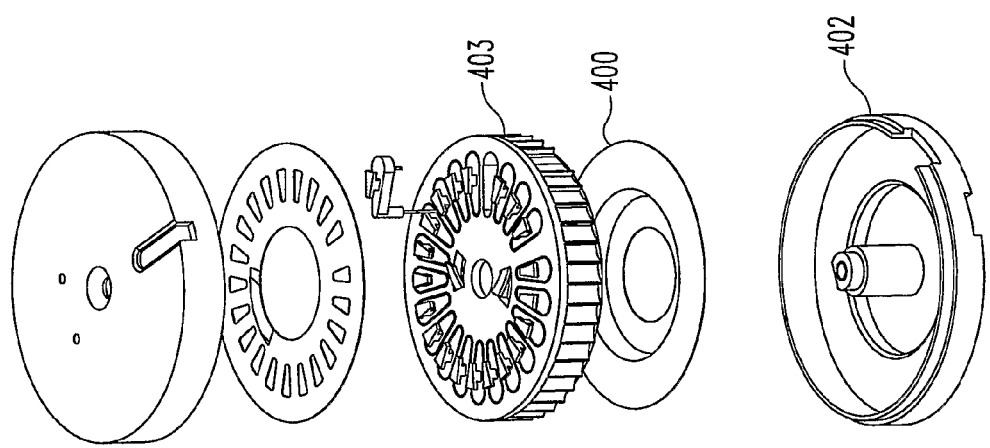
FIG. 43 is an exploded perspective view of a needle cassette in accordance with another embodiment of the present invention showing a sterile protective membrane 400 for protecting cassette body 171.
Figure 44:
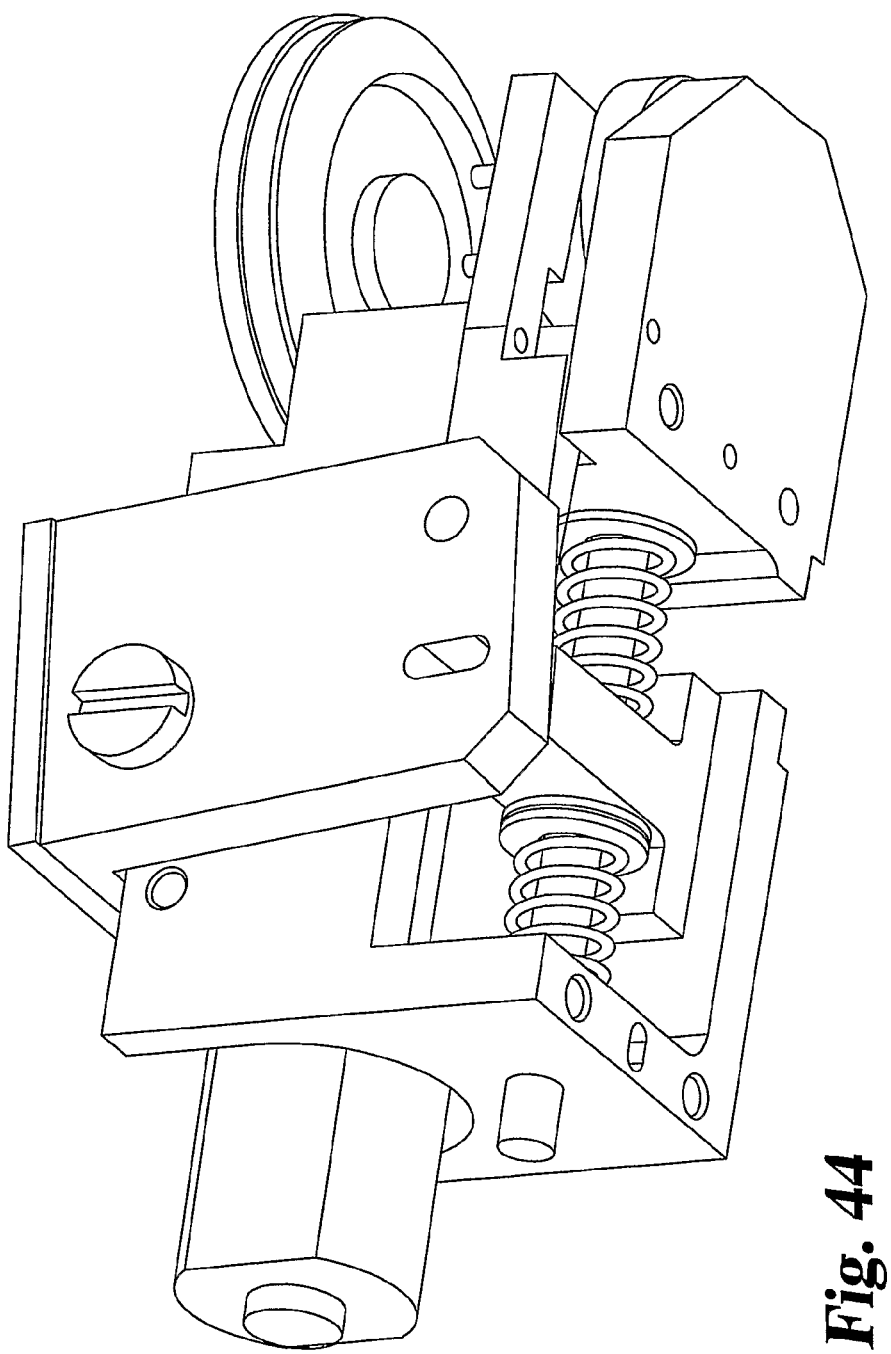
FIGS. 44, 45 and 46 are bottom perspective views of the lifter mechanisms 33 of FIGS. 34, 37 and 40, respectively.
Figure 45:
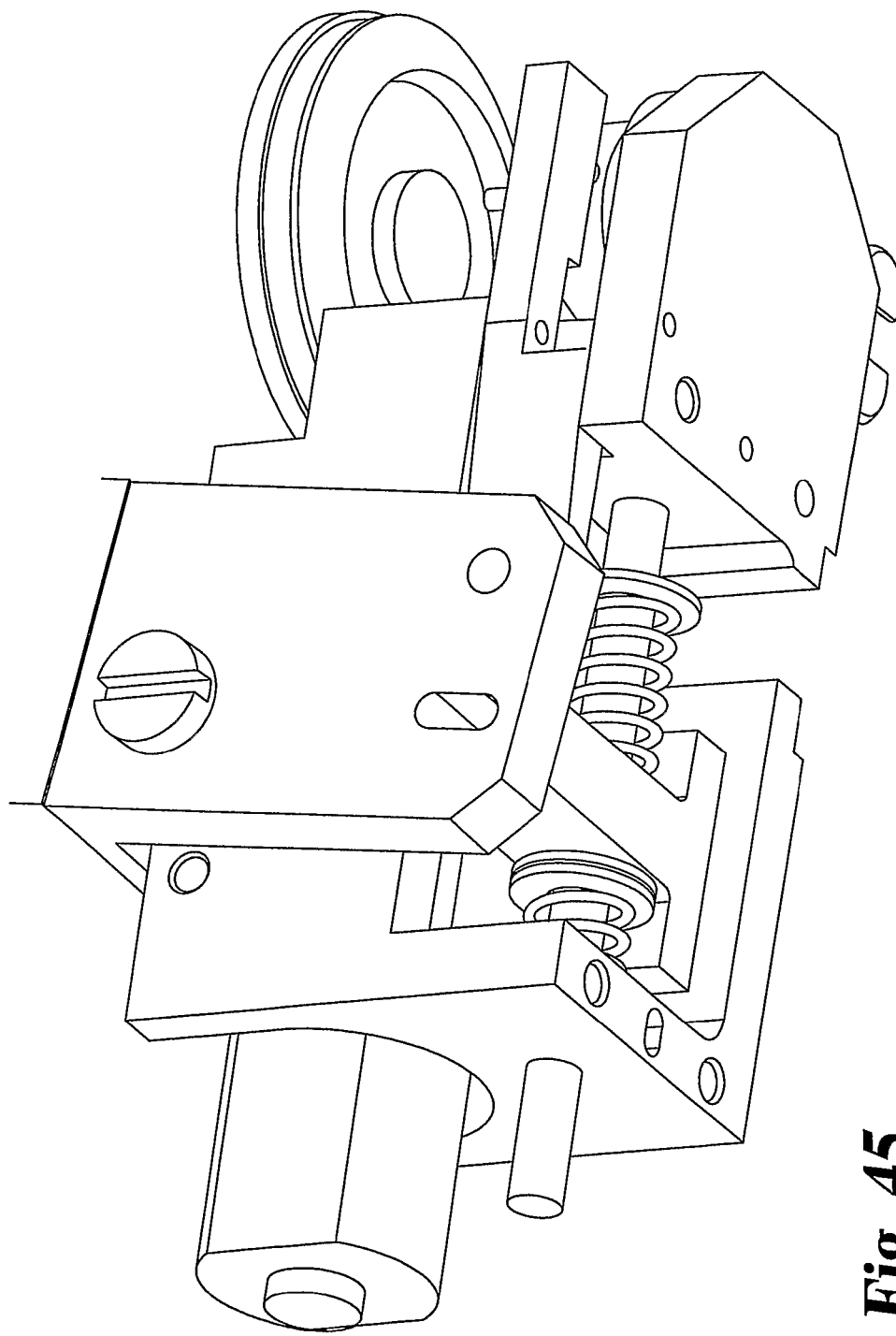
Figure 46:
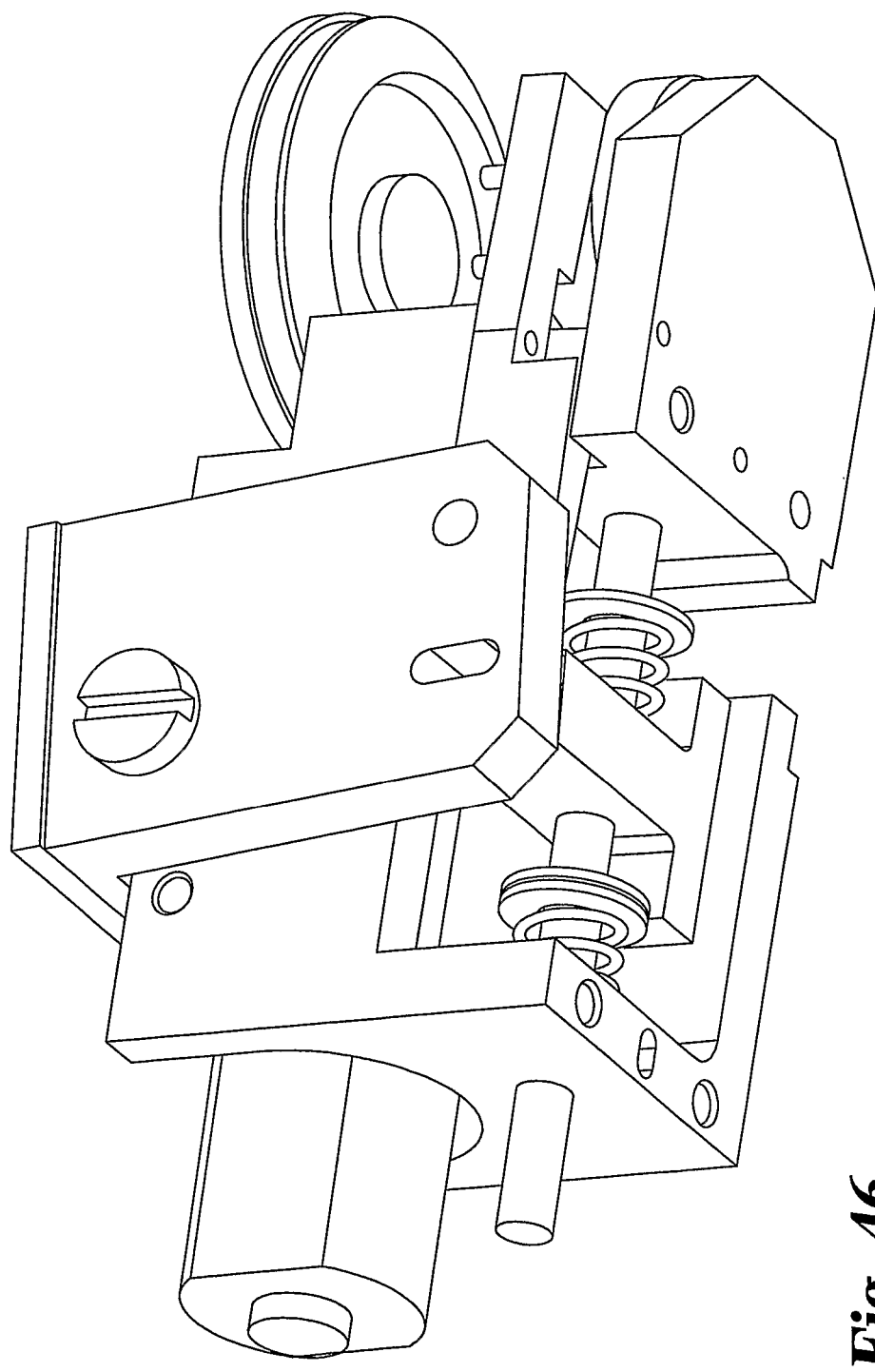

Alternative embodiments are contemplated wherein, instead of shroud array 170, a sterile sealing membrane, much like shaped seal disc 252, is configured to envelop the open, underside of cassette body 171. An example of such membrane is shown in FIG. 43. Membrane 400 basically has the shape of housing bottom 402 and is adhered to the open, underside of cassette body 171 by known means. Membrane 400 would be made of any appropriate material such as Tyvek, polymer film or sterile foil.

Referring to FIGS. 5, 31-33 and 36, the lifter mechanism assembly 33 is shown in relation to needle cassette 32. In operation, lifter assembly 33 operates to rotate the needle-filled cassette body 171 of needle cassette 32, to push down a needle assembly 174 to perform the desired injection and to withdraw such needle assembly 174 from the user to complete the injection cycle. Generally speaking, lifter assembly 33 comprises a frame assembly 261, a lifter body 262, a power assembly 263, a hub assembly 264, a rocker assembly 265, a trigger assembly 266, and a sensor assembly 267. Frame assembly 261 includes a topplate 269 and a plurality of legs 270. Appropriate fasteners such as screws (not shown) extend through holes 271 to connect topplate 269 to legs 270, and legs 270 are similarly connected to base plate 31. Topplate 269 is thereby supported a certain distance above base plate 31. Topplate 269 defines a shaped recess 274, which leads to and is in communication with a plunger hole 275 that extends all the way through topplate 269. Recess 274 and plunger hole 275 are sized and shaped to receive the lifter arm 329 of lifter 317. Topplate 269 further includes a sensor hole 276 and sensor mounting recesses 277 and 278.

Lifter body 262 is mounted to base plate 31 slightly behind topplate 269. Lifter body 262 defines a central channel 280 to receive and support power assembly 263 and includes a forwardly extending shelf 281, which defines a spindle hole 282.

Power assembly 263 includes a motor 285, a gear head 286, and a miter pinion 287 with beveled gear teeth 288. Motor 285 and gear head 286 are retained in lifter body 262 by appropriate means such as set screws (not shown).

Hub assembly 264 is preferably a single, homogeneously molded unit substantially coaxial about a central spindle 290. Just above the bottom end 291 of spindle 290, there is mounted a spiral cam 292 (see FIG. 36), and just above cam 292 is a geneva wheel or geneva 293. Press fit onto and just below the top of spindle 290 is a gear hub 295. Gear hub 295 defines a ledge 296 on which is coaxially received a bevel gear 297, and coaxially affixed atop bevel gear 297 is cam shaft disc 298. The radius of spiral cam 292 about its center (as mounted with spindle 290) increases from a minimum radius to a maximum radius, the difference between the minimum and maximum radii corresponding to the push distance or throw of lifter rod 335 of trigger assembly 266, as described herein.

Geneva 293 sits atop of cam 292 and includes a lower cam disc 300. Just atop cam disc 300, geneva 293 includes a geneva hub 301, which has a substantially constant radius from the axis of spindle 290 except for a pair of flat faces 302 and 303. A pair of pegs 306 and 307 extend up from cam disc 300, directly in front of each corresponding flat face 302 and 303. Cam disc 300 includes a radially extending knob 308 that makes cam disc 300 have a greater radius thereat than anywhere else on cam disc 300. Alternative embodiments are contemplated wherein the radius of cam disc is increased at such specific location by other means such as merely forming cam disc 300 with a larger radius thereat or by having a series of holes into which may be positioned a knob or similar structure to artificially increase the diameter at a certain point. Just below the top end of spindle 290, the gear hub 295 is pressure fit to remain fixed relative to spindle 290, as shown in FIG. 36.

Bevel gear 297 defines a ring of beveled teeth 309 which meshes with and is driven by miter pinion 287. Cam shaft disc 298, affixed to the top of bevel gear 297, defines a plurality of holes 311-313. The entire hub assembly 264 is mounted relative to lifter body 262 by receipt of the bottom end 291 of spindle 290 in hole 282, wherein hub assembly 264 is otherwise free to rotate.

Rocker assembly 265 includes a rocker 316, a lifter 317 and a plunger 318. Rocker 316 has a topplate 320 and a pair of opposing, downwardly extending arms 321 and 322. Rocker 316 is mounted to lifter body 262 by a pair of shoulder screws 323 that extend through holes in each of arms 321 and 322, which enables rocker 316 to pivot freely about the axis of shoulder screws 323. The outside arm 322 of arms 321 and 322 extends down farther than inside arm 321 and defines at its lower end a hole 327 and a slot 328, both of which extend all the way through arm 322. Lifter 317 is securely mounted to topplate 320 of rocker 316 by appropriate means such as screws (not shown) extending through aligned holes in rocker 316 and lifter 317. From its mounting to rocker 316, lifter 317 has a forwardly extending lifter arm 329 with a slot 330 defined therein. Plunger 318 has a non round cross section that closely mates with plunger hole 275 in topplate 269. Plunger 318 is thus limited to vertical reciprocation within plunger hole 275. A slot 331 defined in the upper portion of plunger 318 is sized and shaped to receive lifter arm 329 therein. A pin (not shown) extends through a hole 334 of plunger 318 and through slot 330 of lifter arm 329, thereby connecting plunger 318 for pivotal and limited lateral movement relative to lifter arm 329. At its bottom, plunger 318 defines an oval passageway extending through the width of plunger 318 and shaped to receive the T-bar 243 of any one of the needle assemblies 174. Specifically, as a needle assembly moves 174 in cassette body 171 laterally relative to plunger 318, a T-bar 243 of a needle assembly 174 will slide into a close fit within mating oval passageway 335, thereby engaging plunger 318 with the needle assembly 174 for vertical movement therewith.

Figure 32:
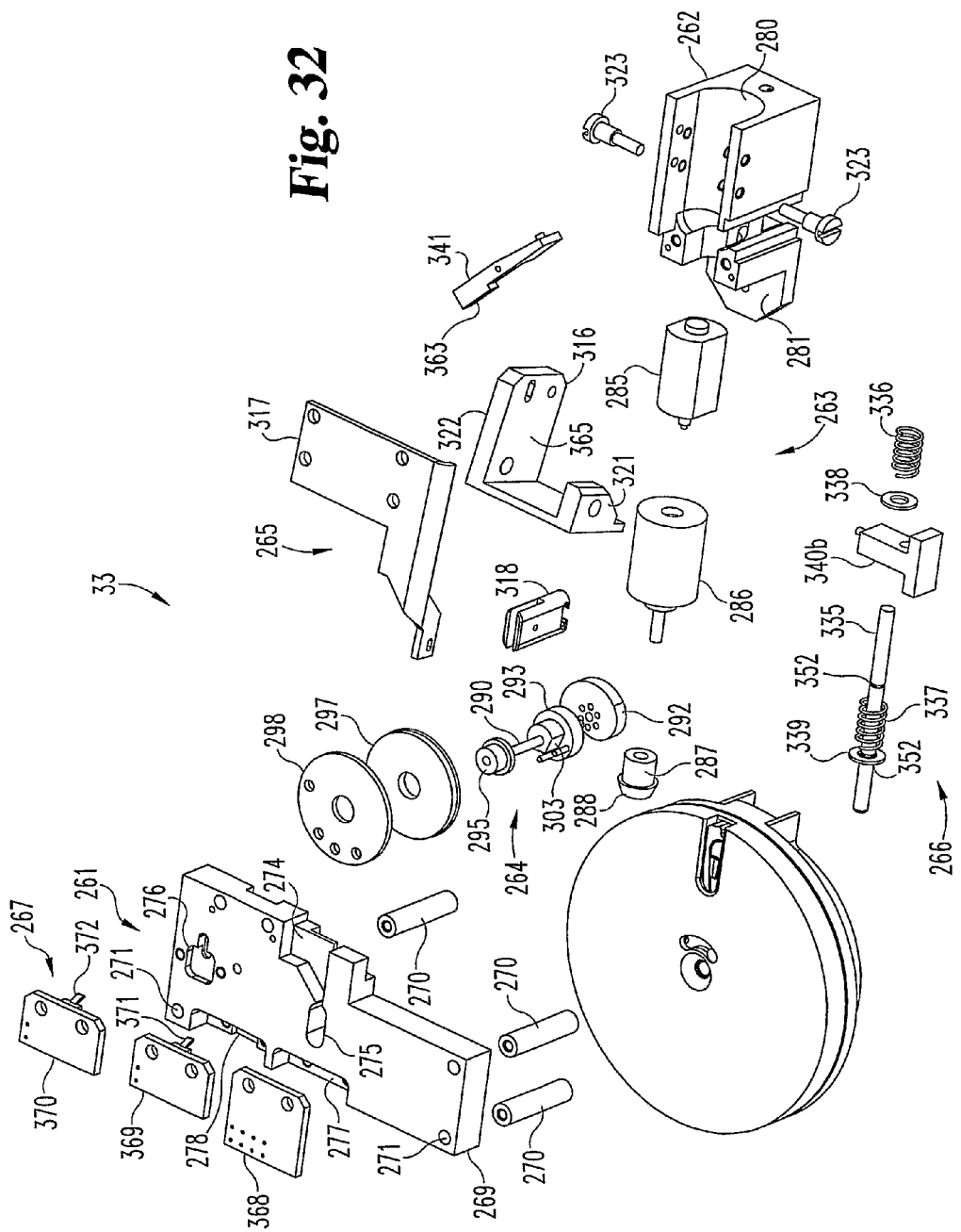
FIG. 32 is an exploded, perspective view of lifter assembly 33 of FIG. 31.

Trigger assembly 266 includes a lifter rod 335, first and second springs 336 and 337, first and second lockrings 338 and 339, slider 340 and latch 341. (FIG. 32 shows a modified slider 340b with wings at its back side to provide additional stability as it slides along lifter rod 335, as described herein). On its underside, lifter body 262 defines a spring cavity 345. Defined in the back and front walls 346 and 347 respectfully, that bound cavity 345, lifter body 262 defines a pair of aligned holes 348 and 349. As shown in FIG. 36, lifter rod 335 extends through aligned holes 348 and 349, its forward end 351 positioned for engagement with spiral cam 292. Springs 336 and 337, lockrings 338 and 339 and slider 340 are all received on lifter rod 335, in the order shown in FIG. 36 and between front and rear walls 346 and 347. First and second lockrings 338 and 339 are fixedly seated in circumferential grooves 352 in a specific position to provide energy storage and release force, as described herein. Properly seated in their grooves, lockrings 338 and 339 are incapable of axial movement along lifter rod 335. Thus, with these components assembled as described, pushing lifter rod 335 rearwardly compresses first spring 336 between back wall 396 and first lockring 338, as shown in FIG. 36. Holding lifter rod 335 in this position stores potential energy for later use.

Slider 340 is a block with a hole 355, through which extends lifter rod 335. Laterally from lifter rod 335, slider 340 has an outwardly extending trip rod 356 that is sized to extend through and move a limited distance in slot 328 of rocker 316.

Figure 34:
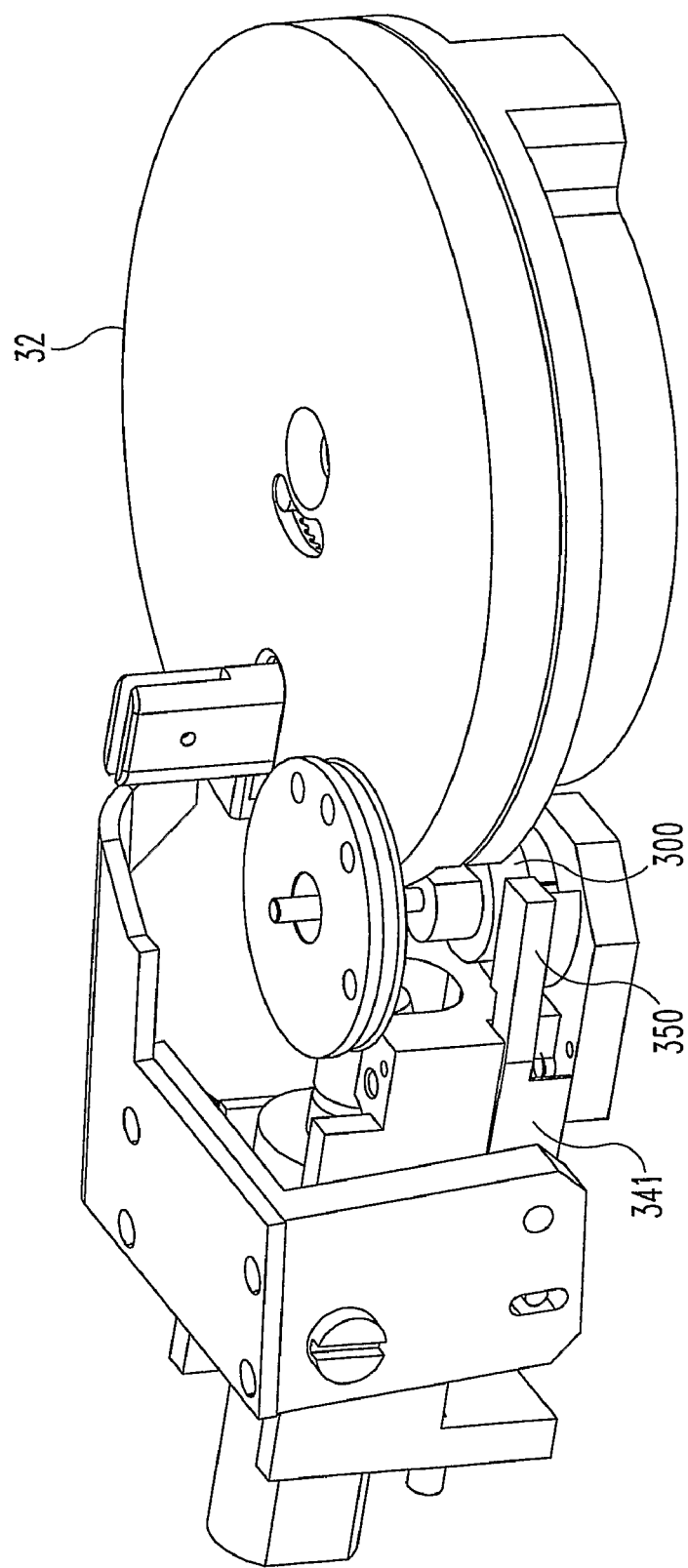
FIG. 34 is a perspective view of the working components of lifter assembly 33 in engagement with needle cassette 32 in the up and ready position.
Figure 37:
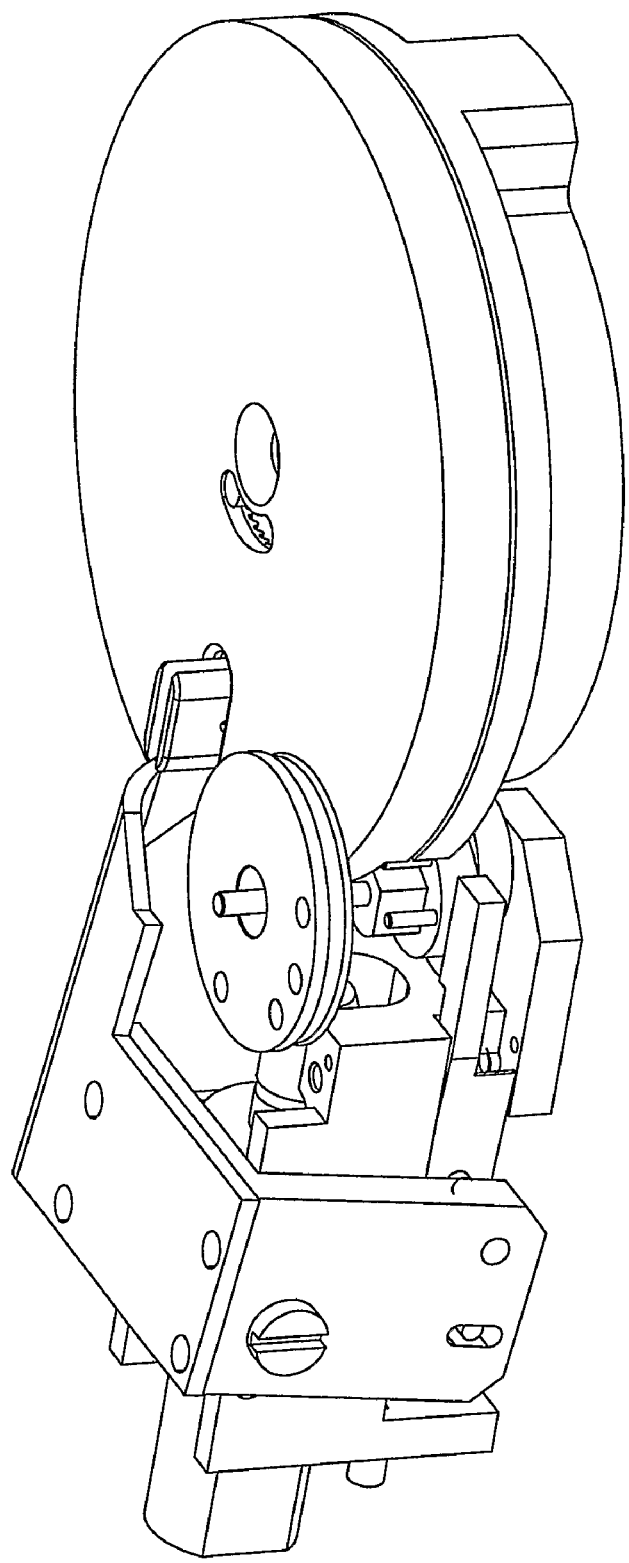
FIG. 37 is a perspective view of the needle cassette and lifter assembly of FIG. 34 and shown in the down, injecting position.
Figure 38:
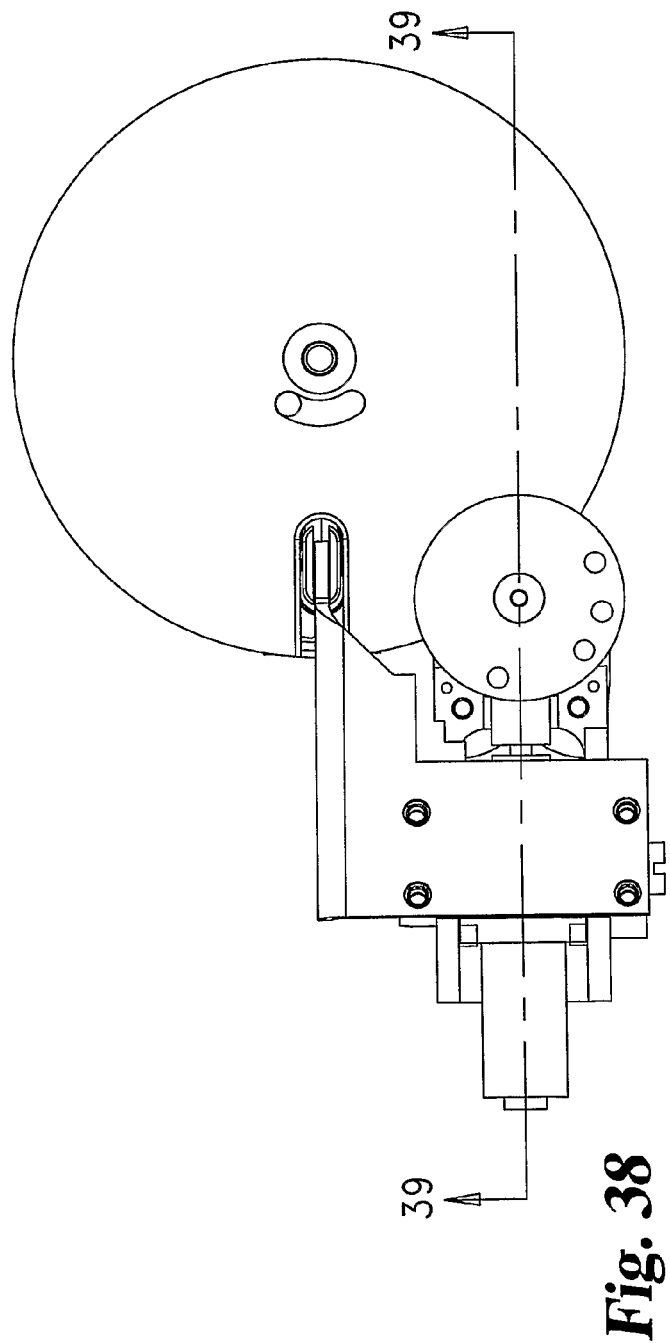
FIG. 38 is a plan view of the needle cassette and lifter assembly of FIG. 37.
Figure 39:
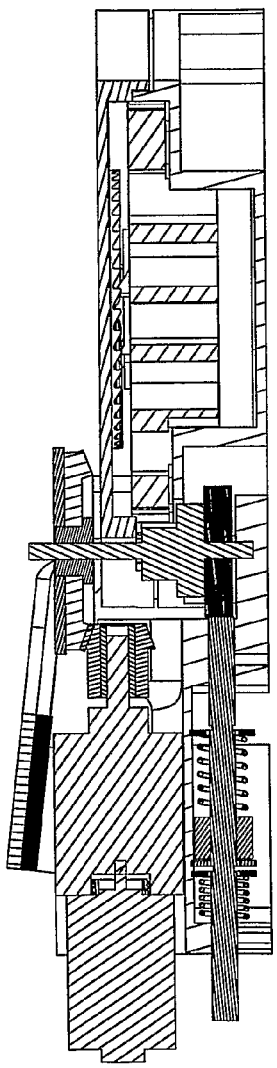
FIG. 39 is a side, cross-sectional view of the needle cassette and lifter assembly of FIG. 38 taken along the lines 39-39 and viewed in the direction of the arrows.
Figure 40:
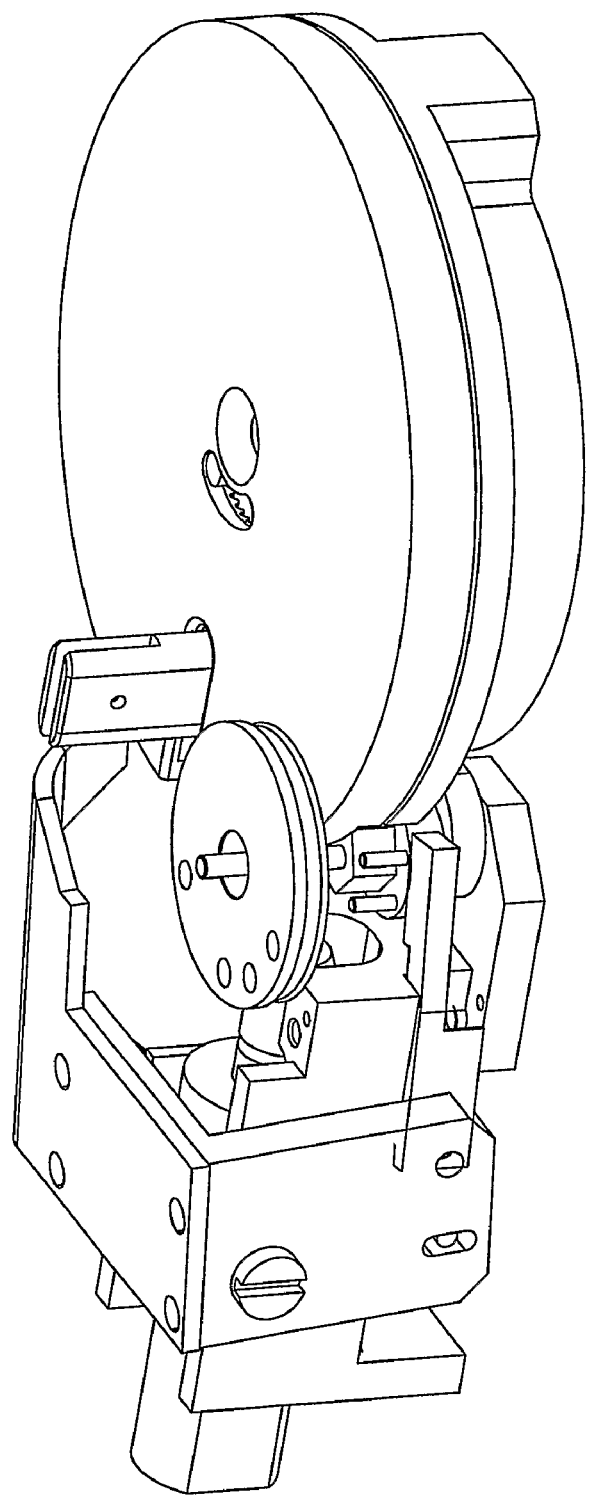
FIG. 40 is a perspective of the needle cassette and lifter assembly of FIG. 34 and shown in the injection retraction position.
Figure 41:
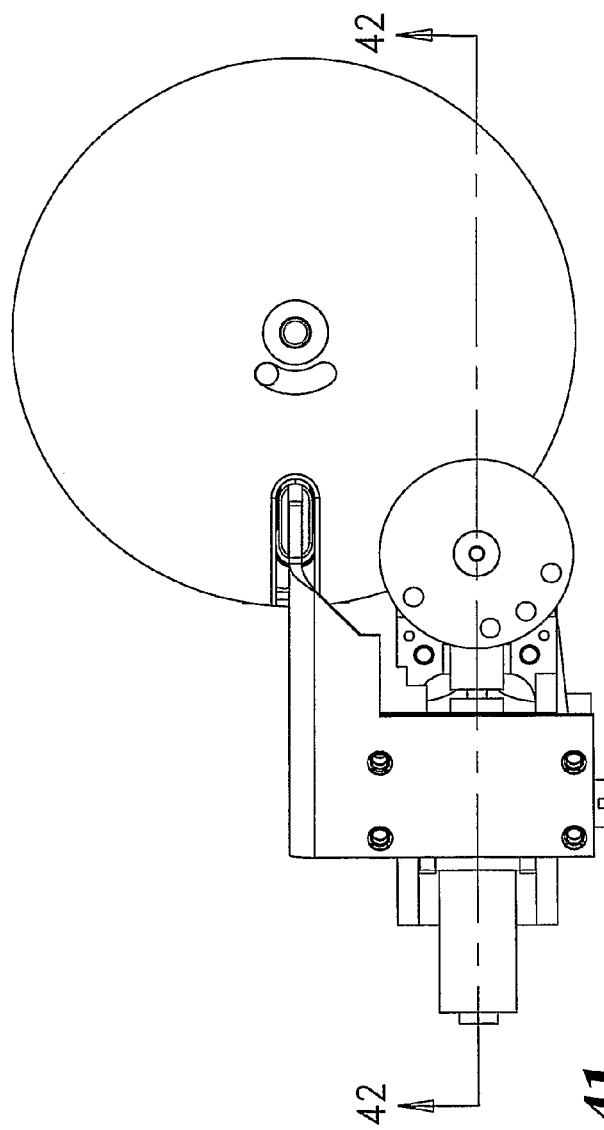
FIG. 41 is a plan view of the needle cassette and lifter assembly of FIG. 40.
Figure 42:
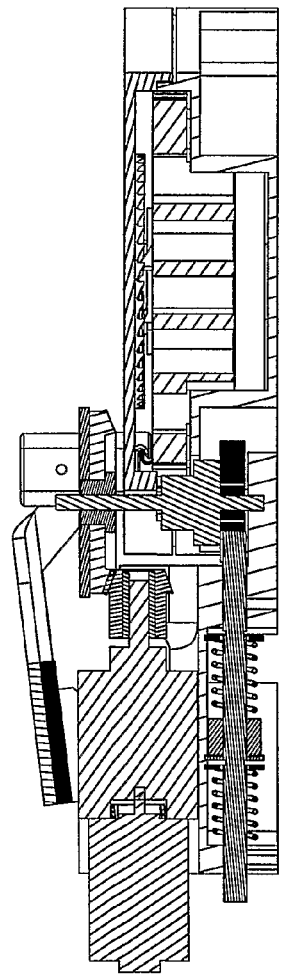
FIG. 42 is a side, cross-sectional view of the needle cassette and lifter assembly of FIG. 41 taken along the lines 42-42 and viewed in the direction of the arrows.

On the same side as spring cavity 345, and adjacent forward wall 347, lifter body 262 defines a small recess 357 in which latch 341 is pivotally mounted by appropriate means such as a pin (not shown). Mounted as shown in FIG. 34, latch 341 is biased by appropriate means such as a coil spring or leaf spring (not shown), to rotate generally counterclockwise, as will be described with the operation of lifter assembly 33 herein. Latch 341 essentially has a forward arm 358 and rearward arm 359 and pivots about its approximate center at 360. On the inside (or counterclockwise side as shown in FIG. 33), forward arm 358 defines a cam face 363 (FIG. 32), which is positioned to bear against the lower cam disc 300 of geneva 293. From its rearward arm 359, latch 341 has a trigger pin 364 that extends outwardly and also in a counterclockwise direction, as viewed in FIG. 33. With lifter assembly 33 assembled as described and shown in FIGS. 31-36, latch 341 is pivotally mounted within recess 357 and spring biased so that cam face 363 bears against lower cam disc 300 of geneva 293, and rearward arm 359, and specifically trigger pin 364, bears against the inside surface 365 of arm 322 of rocker 316. The path of forward through-hole 327 is sized and positioned to align with trigger pin 364 when rocker 316 is pivoted about shoulder screws 323, and upon the proper angular position of geneva 293, trigger pin 364 will directly align with hole 327. Then, latch 341 will pivot, and trigger pin 364 will enter through-hole 327. As a result, of the continual bias of latch 341 against arm 322, trigger pin 364 will hold rocker 316 from further movement (with lifter arm 329 in the up position) until latch 341 is again pivoted away from rocker arm 322.

Sensor assembly 267 includes three circuit boards 368, 369 and 370 which are secured to topplate 269 with appropriate means such as screws (not shown). Circuit board 368 is mounted in recess 278, and includes two reflective/optical sensors that are positioned over post 217 (which rides within groove 205) of cassette 32, thereby detecting a low- or no-needle condition in needle cassette 32. Circuit board 369 includes an encoder switch 371 that is biased down and is physically tripped when and for as long as a needle cassette 32 is inserted into apparatus 10. Conversely, when needle cassette 32 is pulled out of apparatus 10, switch 371 returns to its down position, which is interpreted by the main circuit board 36 as a no-needle cassette condition. Circuit board 370 is mounted atop topplate 269, includes an encoder switch 372 that extends through sensor hole 276 in top plate 269 and engages with the four holes 311-314 on cam shaft disc 298. Thus as hub assembly 264 rotates, encoder switch 372 (being biased to the down position, but held up by camshaft disc 298) drops into the holes 311-314 and thus registers the angular position of cam shaft disc 298. Alternative embodiments contemplate other suitable sensor means such as and without limitation, optical sensors and magnetic sensors. The information from circuit boards 368-370 and any other sensors desired to be included in apparatus 10 is relayed to circuit board 36 for processing.

In operation, with apparatus 10 in the up, ready position, the user presses button 18. The hub assembly 264 rotates with cam disc 298 rotating so that the second hole 312 engages with the encoder switch 372 at which point the circuit board is alerted that the cassette 32 has been rotated to a read position with a needle assembly 174 in position for injection. When the needle assembly is put in the ready position, the maximum radius portion (308) of the lower cam disc 300 has pushed forward arm 358 of latch 341 out—that is, pivoted latch 341 so that the trigger pin 364 has disengaged from rocker arm 322, and rocker arm 322 is there biased to rock forwardly counter clock-wise as viewed in FIG. 33 by virtue of the slider 340, which is biased by spring 337 and because the pin for slider 340 is engaged in the slot 328 of rocker arm 322. Upon its release, rocker arm 322 it is pivoted forward, quickly pushing needle assembly 174 down to perform the insertion. The hub continues to rotate, but when the encoder switch drops into the next hole 313, the motor is instructed by circuit board 36 to stop. At that point the needle has been inserted and then the other motor assembly 96 kicks in to move the direct drive assembly and to expel the drug from the drug cartridge to perform the injection.

The control circuit calculates the time necessary to deliver the injection. After the desired dosage has been administered (as determined by predetermined calculations based upon number of rotations of the motor and volume and surface area of the drug cartridge, and so on), the direct drive system stops advancing the plunger and the other motor power assembly 263 is activated, which rotates hub assembly 264. The spiral cam 292 rotates, which begins again preloading the lifter rod 335. When it releases rocker 316, rocker 316 is then free to be pushed by the slider 340 and to drive needle assembly 174 to an injection state. The injection occurs and the hub assembly begins rotating again, but the rear spring 336 is still fully loaded. With the hub assembly beginning to rotate again, the lower spiral cam 292 rotates until the peak radius portion passes lifter rod 335 and the lifter rod is then free to shoot forward toward the small radius section of the spiral cam. The energy released from rear spring 336 pushes slider 340 forward. When lifter rod 335 is allowed to shoot forward, rear lockring 338 engages the backside of slider 340 and pushes it along with the rocker, which is engaged with the slider, which pulls the needle assembly 174 back up (out). When the fourth hole 311 arrives at encoder switch 372, the control circuit is thus notified that the spiral cam 292 has rotated to the point where it has released the lifter rod. Once the fourth hole 311 gets to the encoder switch on board 370, and the control circuit is notified that the needle has been withdrawn, then the hub assembly continues to rotate and the spiral cam 292 slowly pushes lifter rod 335 back against the bias of the springs, which preloads both springs again. Rotation of this hub assembly 264 also continues rotating the geneva 293 which rotates needle cassette assembly 34. The peg (306 or 307) comes around one-half turn until the land between two needle assemblies is what is exposed through plunger slot 202. Thus, when the encoder switch of board 370 reaches first hole 311, the control circuit knows that apparatus 10 has reached its home position (next needle assembly 174 is up and ready). The control circuit has a timer with it and the time elapsing between signals from the encoder as it engages from hole to hole is being monitored so that if the amount of time between any two holes on disc 298 deviates significantly from historical time as it is known to occur, then an error message is issued alerting the user that there may be a problem with the device.

Alternative embodiments contemplate more or fewer needle assembly slots 193 to correspond with any desired dosage configuration or schedule. All other aspects of apparatus 10 could remain the same except those necessary to operate with a cassette body 171 having a different number of needle assembly slots 193. For example and without limitation, a disc 171 with only 14 slots 193 would need to be rotated approximately 25.7° after each injection to index to the next needle assembly. Thus, the slots on the outer edge of the disc 171 would be spaced farther apart, and the geneva cam configuration would be slightly different.

Alternative embodiments contemplate the base plate being formed as part of the outer casing, rather than being a separate component therefrom.

Referring again to FIG. 19, apparatus is shown for providing a fluid path between a drug cartridge 390 and a needle cassette 391 in accordance with an alternative embodiment of the present invention. Such system is intended to be the same as the system shown in FIG. 10 except as shown and described herein. Such system includes a needle cassette 391 and a drug cartridge 390 that engages with needle cassette 391 to permit a needle assembly 392 to be forced downwardly to complete a fluid path with drug chamber 74. Instead of bi-directional valve 87, drug cartridge 391 is provided with a valve block 395 that includes a passageway 396 with a septum 397 at one end and an outwardly extending needle cannula 398 at the opposite end. Needle cannula 398 is sized and configured to engage and pierce a complementary septum 401 provided in drug cartridge 390. Alternative embodiments are also contemplated wherein the needle septum is located at both ends of passageway 396, and needle cannula to pierce such septums are located in needle assembly 392 and the drug cartridge 390. Any such additional configurations are contemplated and acceptable depending on other concerns such as cost, safety, reliability, etc. Configuration of this access port 401 on front face 399 in this manner facilitates filling drug cartridge 390 through the same access port 401 instead of through the rear of the cartridge or through the plunger itself.

Alternative embodiments are contemplated wherein drug cartridge 35, in the same or modified shape than shown herein, is inserted axially through a portal somewhere at the bottom of apparatus 10.

Alternative embodiments are contemplated for advancing plunger 54 or any plunger or piston in a piston-cylinder type drug container, including without limitation a pin or arm connected to the back of the piston and extending radially therefrom for engagement with a driving mechanism.

Figure 49:
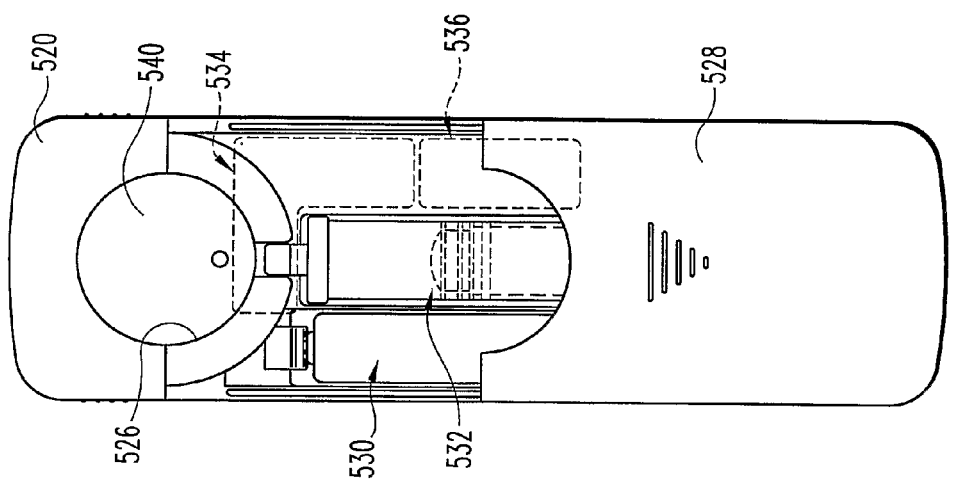
FIG. 49 is a plan view of the bottom side of the apparatus of FIG. 47, wherein the access door of the housing has been slid open to expose the battery and the drug cartridge.
Figure 47:
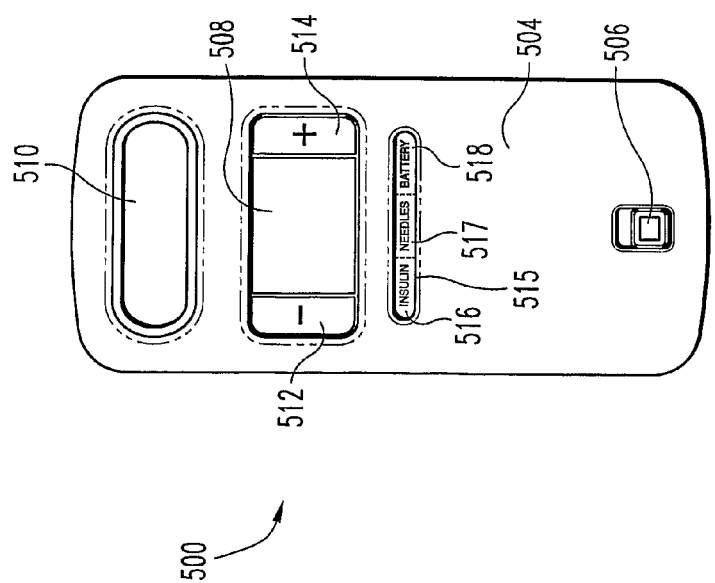
FIG. 47 is a plan view of the top side of an apparatus for delivering a pharmaceutical liquid to a patient in accordance with another embodiment of the present invention.
Figure 50:
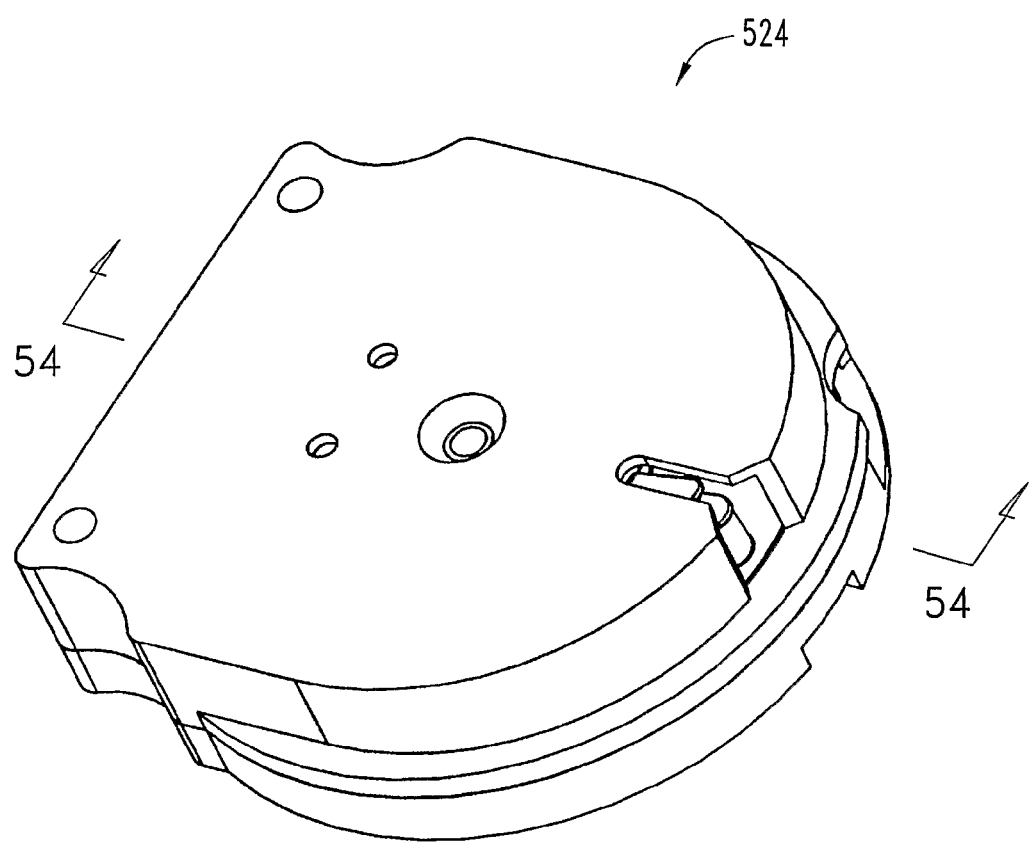
FIG. 50 is a top perspective view of a needle cassette of the apparatus of FIG. 47 removed from the remainder of that apparatus.

Referring now to FIGS. 47-49, there is shown an apparatus 500 for delivering a pharmaceutical liquid, such as insulin, in accordance with another embodiment of the present invention. Apparatus 500 includes an exterior housing 502 having a top surface 504 formed of a metal skin or plate to provide an aesthetically pleasing appearance. The remainder of the exterior housing, including its drawer 520 and access panel 528, is formed of a suitably durable and lightweight material, such as an injection molded plastic, which material can be formed to provide an interior adapted to mount and accommodate the internal components of the apparatus.

The top of apparatus 500 serves as a control panel providing various user interaction elements, including a sliding on/off switch 506, a visible display 508, an activation or injection button 510, and dose-adjusting buttons 512 and 514 that flank the display 508. Moving switch 506 to turn on apparatus 500 causes display 508 to show a proposed dose for delivery that is a default dose programmed into the control system of the apparatus. Buttons 512 and 514 can be operated by a user to decrease or increase, respectively, from the default dose the dose to be actually administered upon the user pressing button 510. Display 508 may be a lighted LCD screen on which the control system displays information, such as dose size, or use instructions or feedback. For example, lights around the display may flash when the apparatus determines a dose has been delivered and the injection needle withdrawn, which lights may be accompanied by a vibration of the apparatus produced by a not shown vibratory element therein.

The interaction elements also include a translucent window 515 that covers a row of lights. The control system of apparatus 500 controls these lights to selectively illuminate the appropriate segment of the window to provide various types of notice to a user. For example, window region 516 is illuminated when the medicine cartridge is absent or empty, window region 517 is illuminated when the needle supply is low or exhausted, and window region 518 is illuminated when the battery level is low.

Removable cassette drawer 520 is provided with connecting elements allowing for a sliding mounting to the rest of the housing 502, which drawer when so mounted forms a forward end portion of apparatus 500. Cassette drawer 520 defines an internal hollow 522 complimentarily configured to the periphery of a disposable needle cassette 524. When a user inserts cassette 524 into hollow 522, the floor of the cassette housing bottom 540 fits into an opening 526 through the underside of cassette drawer 520 so as to essentially form the bottom surface of the apparatus housing. Although in the embodiment shown in FIG. 48 the needle cassette is a disposable unit while the cassette drawer is a reusable portion of the apparatus housing, in an alternate embodiment the cassette drawer may be integrally formed and disposable with the needle cassette.

Apparatus housing 502 includes on its bottom side an access door 528 that is shown in FIG. 49 in a retracted or slid out arrangement, at which arrangement both the power source 530 and the separate drug cartridge 532 are accessible to the user for replacement. Battery 530 and drug cartridge 532 are seated within compartments molded into the apparatus housing, and not shown sensors, such as mechanical switches operatively connected to the circuit board of apparatus 500, are provided in the apparatus to allow the presence or absence of either or both of the battery and cartridge to be automatically recognized. When door 528 is closed, the operative elements of apparatus 500 are protectively enclosed within the housing. In FIG. 49, a lifter assembly 534 and direct drive assembly 536 of apparatus 500 are abstractly shown in dashed lines, and for the most part such assemblies are encased within the housing to prevent ready access thereto by a user via access panel 528. The control system of apparatus 500, which may be a circuit board that naturally is operatively connected to the user interaction elements and the motors of the lifter assembly and direct drive assembly, and including its sensors and the various appropriate connections, etc., are not shown to facilitate illustration, and may be mounted within the housing in a suitable fashion as is known in the art.

Figure 51:
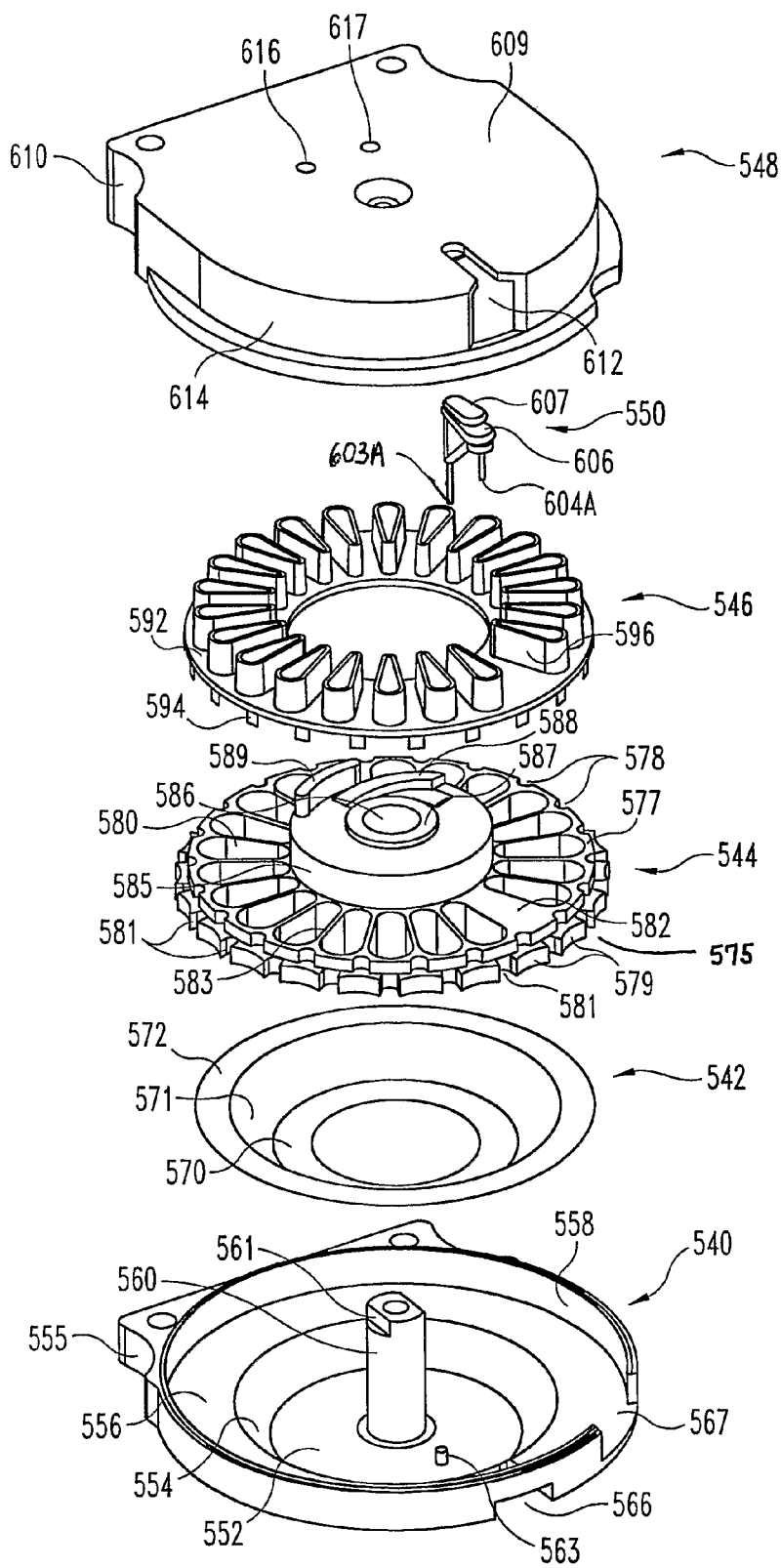
FIG. 51 is a top perspective, exploded view of the needle cassette of FIG. 50, wherein only a single needle assembly of the normal complement of needle assemblies is shown.
Figure 52:
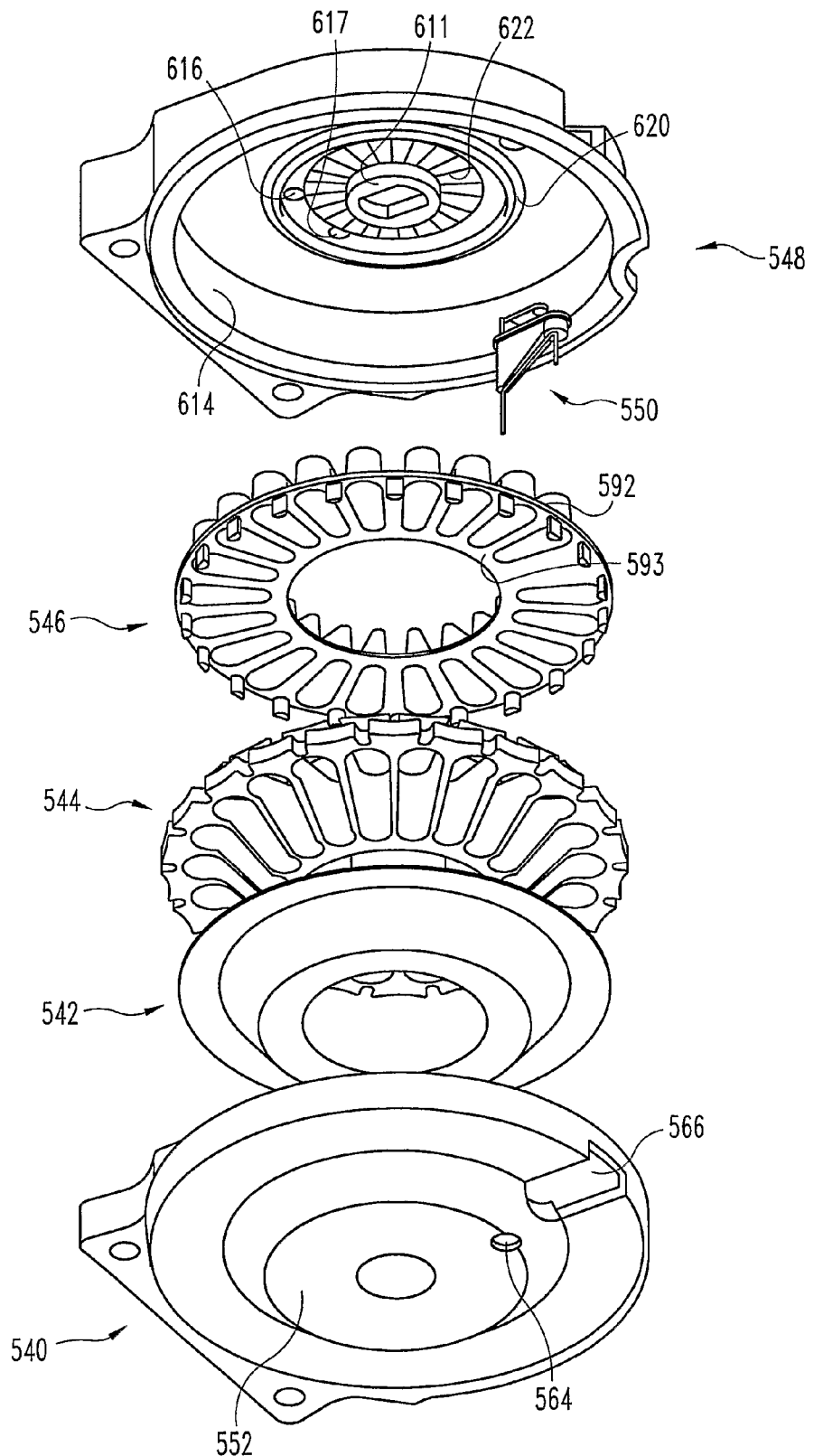
FIG. 52 is a bottom perspective view of the cassette components shown in FIG. 51.
Figure 53:
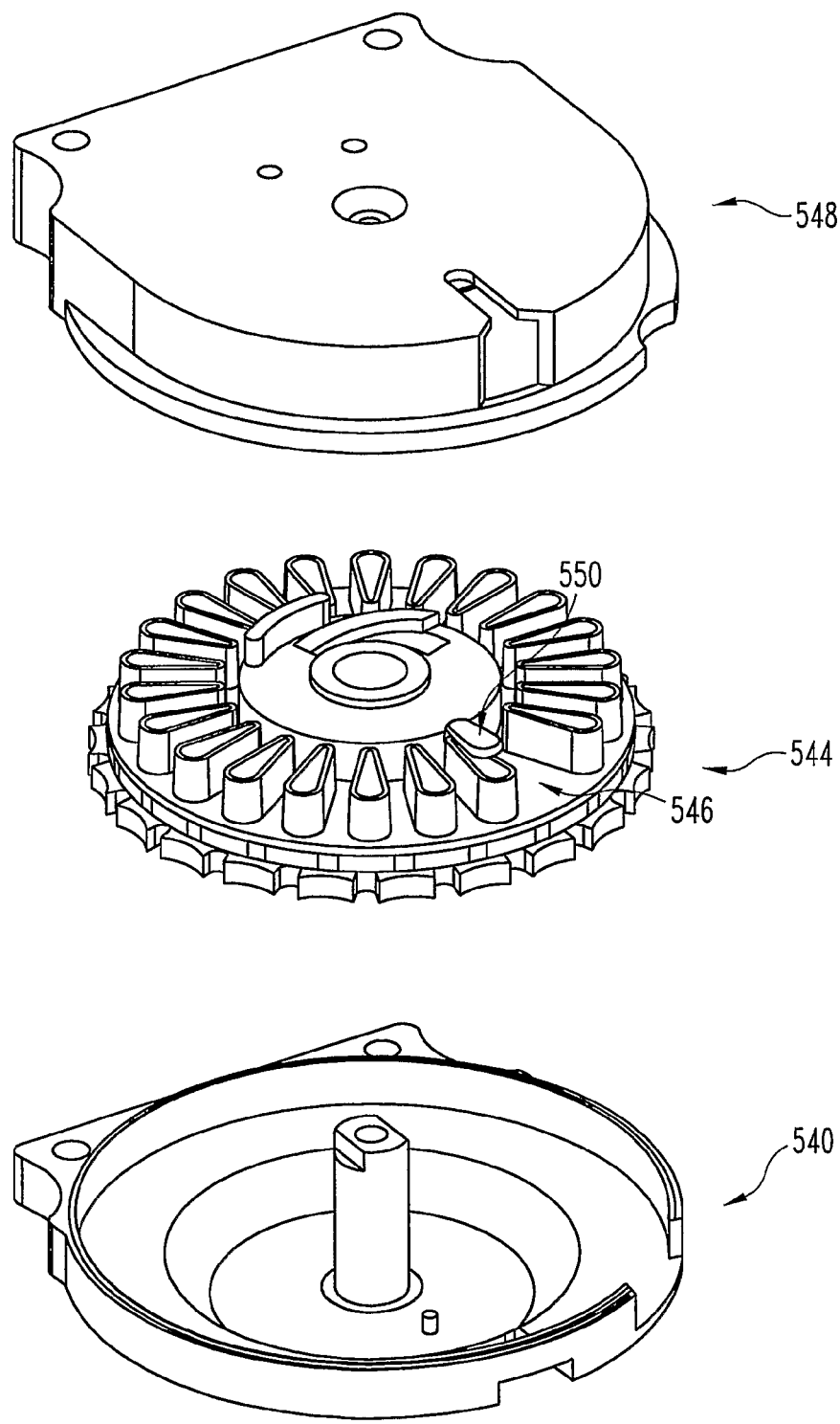
FIG. 53 is a view of the components of FIG. 51 at an intermediate stage of their assembly to form the needle cassette.

Referring now to FIGS. 50-54, needle cassette 524 generally includes a housing bottom 540, a bottom sealing membrane 542, a base or carousel 544, a needle-supporting sealing membrane 546, a housing top 548, and a plurality of needle assemblies, only one of which is shown in FIGS. 51-53 at 550. Housing bottom 540 is molded from plastic and includes a circular floor 552, an angled annular or frustoconical flange 554 that transitions to an annular ledge 556, and a cylindrical wall 558. Projecting upwardly from the center of floor 552 is an assembly post 560 about which carousel 544 is rotatable. The upper end of post 560 is keyed at 561 to provide a supporting surface for the housing top 548, and serves as a point for connection therewith, such as with a screw or other suitable fastening system, such as a snap connection. A shorter post 563 also upwardly projects from floor 552 in a radially spaced relationship with post 560. Post 563 serves as an abutment for a correspondingly designed shoulder 569 of carousel 544 to halt further rotation of the carousel at the end of the useful life of the needle cassette. A hole 565 in floor 552 and flange 554 (see FIG. 54) allows a skin piercing needle to extend downward through that hole upon activation of apparatus 500 to deliver medication. Another opening 566 (see FIG. 54) radially aligned with hole 565 and extending within flange 554, ledge 556 and wall 558 accommodates the septum covered dispensing port of the drug cartridge 532, as well as allows a septum piercing needle to extend downward through that opening during activation. An opening 567 through wall 558 is angularly spaced from opening 566 and is sized to enable a geneva wheel 646 to engage the outer edge of carousel 544 for indexing.

Sealing membrane 542 is made of a multi-layer, needle pierceable film and provides a sterility barrier for the needle assemblies along the underside of carousel 544. Membrane 542 includes an annular flange 570 and a larger diameter annular flange 572 interconnected by a frustoconical region 571. The underside of flange 570 may be provided with a ring of indicia, visible through housing floor hole 565, to indicate which needle of the needle cassette is ready for the next insertion, or to indicate the number of unused needles remaining in the cassette.

Carousel 544 is a one-piece plastic molding with a central, indexing disc-section 575 that is below a smaller diameter disc-section 577. Equally angularly spaced indents 578 around the periphery of disc-section 577 are designed to accept alignment tabs 594 of needle-supporting sealing membrane 546. Around its periphery, carousel section 575 includes twenty-two equally angularly spaced orientation tabs 579 with flanking notches 581 that allow for the engagement with the carousel advancing mechanism of the lifter assembly 534 to provide the indexing feature. A central radial region of carousel 544 includes a ring of radially oriented, ovate slots 580 that extend through the height of the carousel. Each slot 580 is adapted to accommodate a single one of the plurality of needle assemblies 550. In the shown embodiment, twenty-one identical slots 580 are formed, and a single solid, or slotless, space 582 is provided. In this manner, twenty-two angular positions are provided, with the slotless space 582 being aligned with housing opening 566 at the end of needle cassette life to facilitate safe disposal of the cassette. An upstanding disk portion 585 of carousel 544 includes a central bearing ring 587 around a post-receiving, axial throughbore 586, an arcuate ratchet arm 588, and an upstanding flag element 589.

Flag element 589 is utilized by the apparatus control system to determine needle cassette status. In particular, the upper surface of flag element 589 is adapted to cooperate with a not shown sensing mechanism within the apparatus housing in order to allow determination of an adequate needle supply. For example, if an optical detector is the sensing mechanism, the upper surface of flag element 589 may be coated with a light reflective film. When flag element 589 is recognizable by such sensing mechanism as being below housing port 616 but not below housing port 617, the apparatus control system understands that a new needle cassette is loaded within apparatus 500. When flag element 589 is recognizable by such sensing mechanism as being below housing port 617 but not below housing port 616, which arrangement occurs after the needle cassette has been rotated during its subsequent use, the apparatus control system understands that the needle supply is reaching a low level, such as three or less needles remaining, and indicates such to the user by illuminating window region 517. When after further apparatus use the flag element 589 is recognizable by such sensing mechanism as being below both housing ports 617 and 616, the control system understands that the needle cassette has reached the end of its useful life, and may indicate such to the user as well as prevent use of the apparatus prior to insertion of a new needle cassette.

Figure 54:
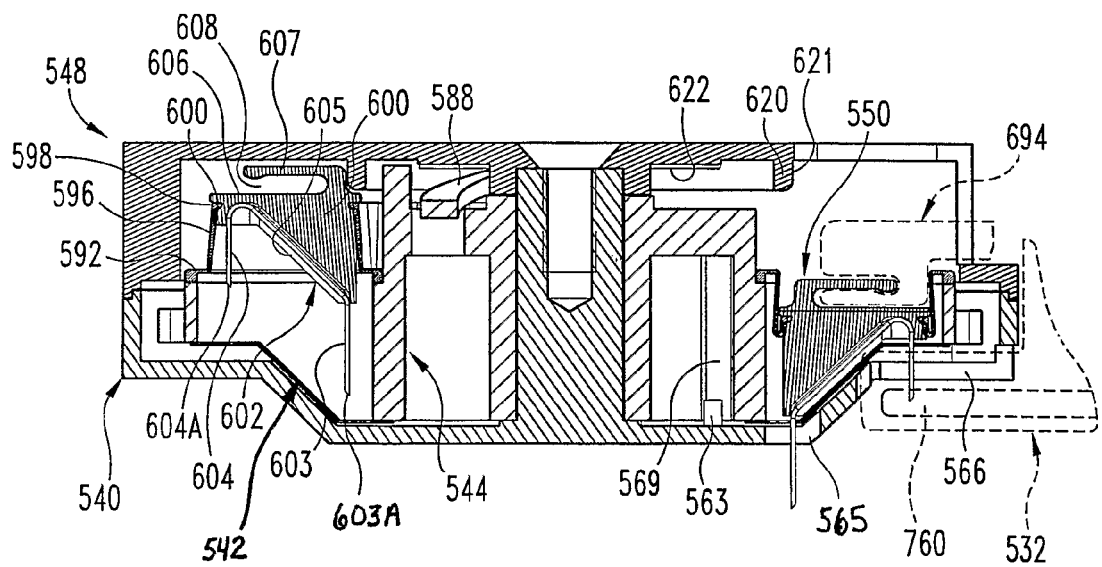
FIG. 54 is a cross-sectional view, conceptually taken along line 54-54 of FIG. 50, of the needle cassette, wherein one of the needle assemblies is shown in a plunged state and engaged with an abstractly shown drug cartridge and lifter assembly.
Figure 55:
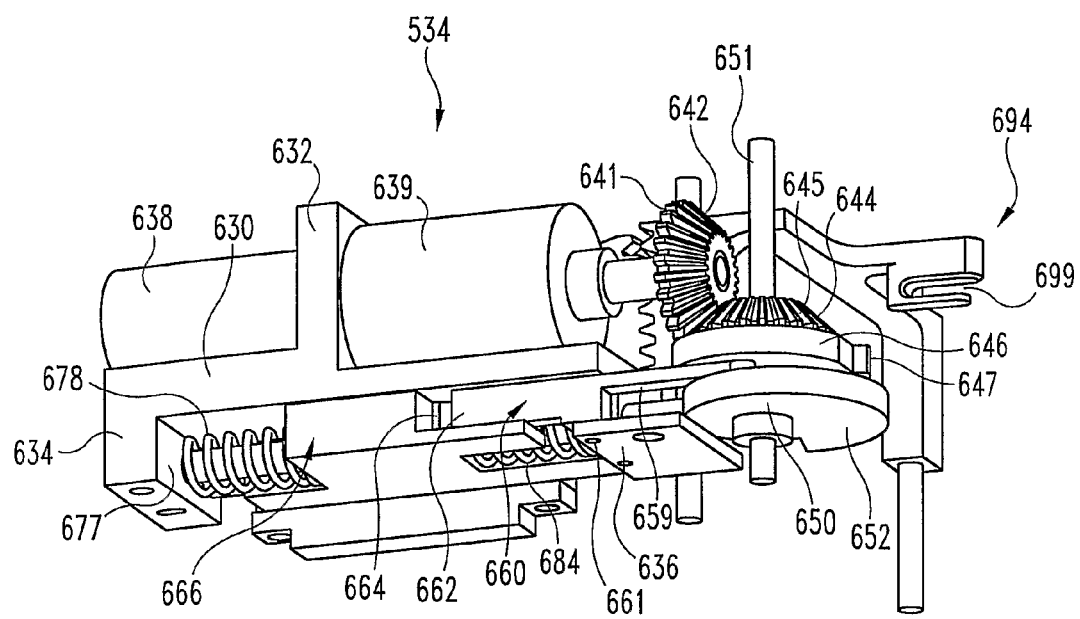
FIG. 55 is a bottom perspective view of a lifter assembly of the apparatus of FIG. 47 shown removed from the remainder of that apparatus.
Figure 56:
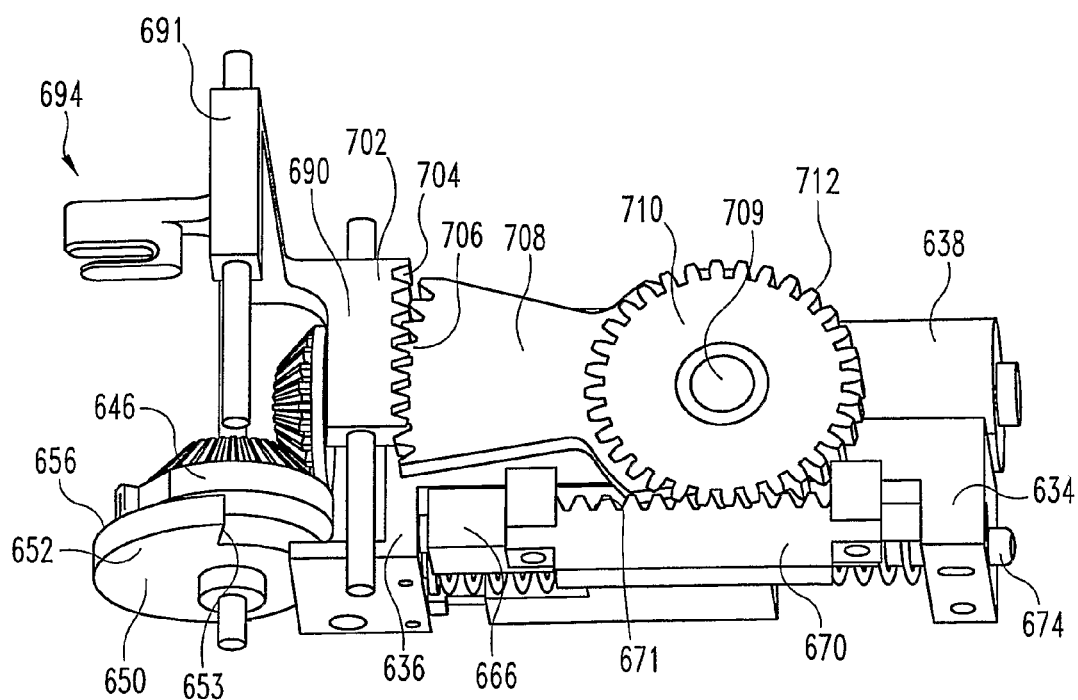
FIG. 56 is another bottom perspective view, taken from a different angle, of the lifter assembly of FIG. 55.
Figure 57:
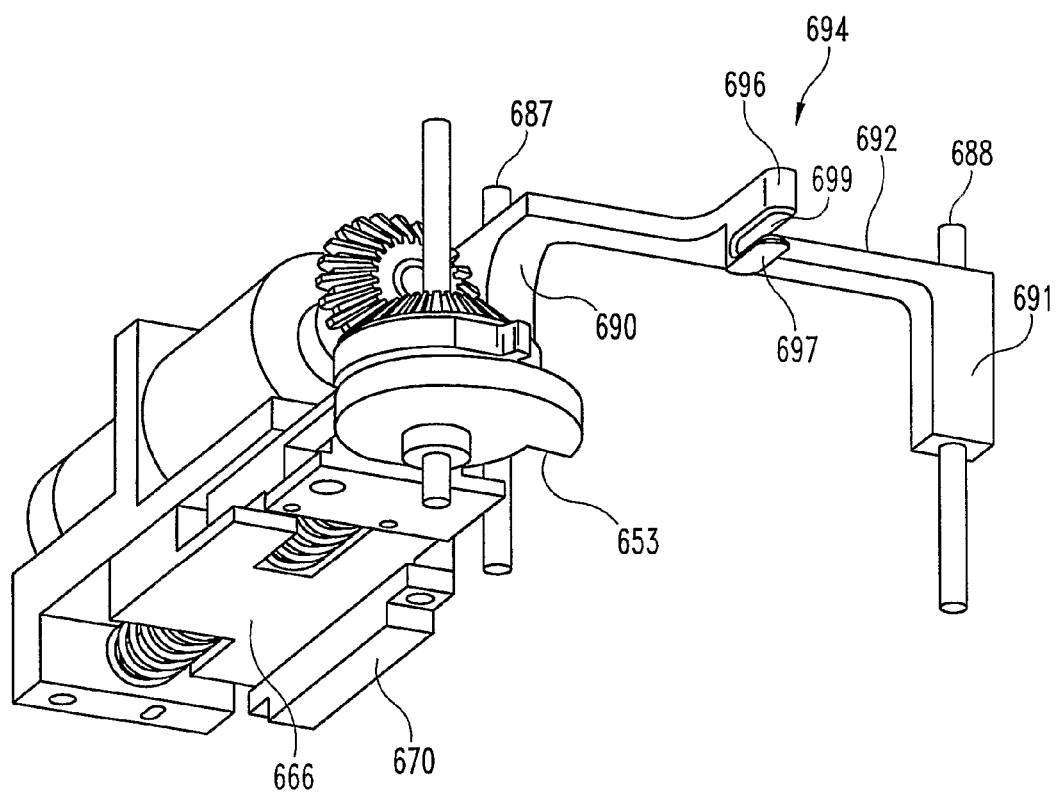
FIG. 57 is a bottom perspective view, taken from still another different angle, of the lifter assembly of FIG. 55.
Figure 58:
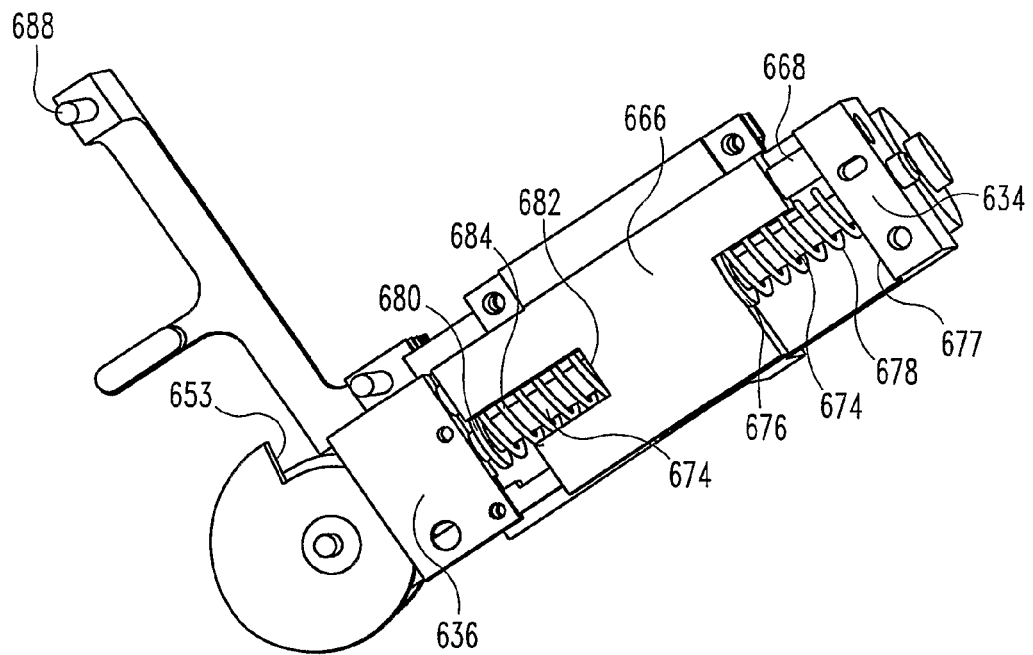
FIG. 58 is a nearly plan view of the bottom of the lifter assembly of FIG. 55.
Figure 59:
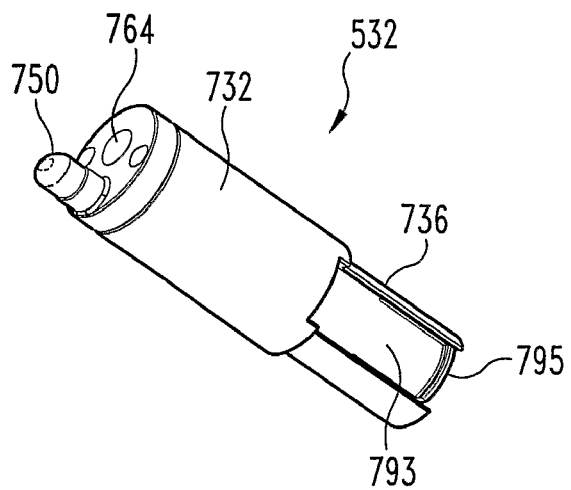
FIG. 59 is a front perspective view of a drug cartridge of the apparatus of FIG. 47 removed from the remainder of that apparatus.
Figure 60:
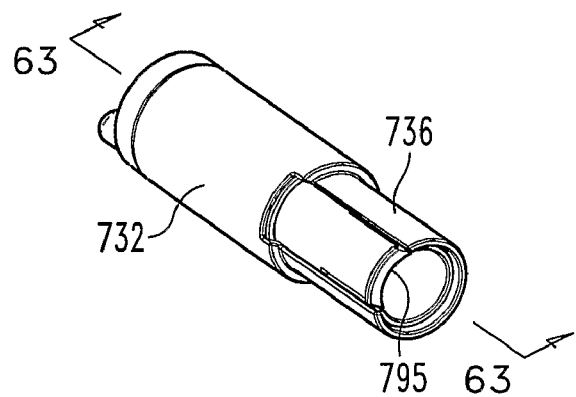
FIG. 60 is a rear perspective view of the drug cartridge of FIG. 59.
Figure 61:
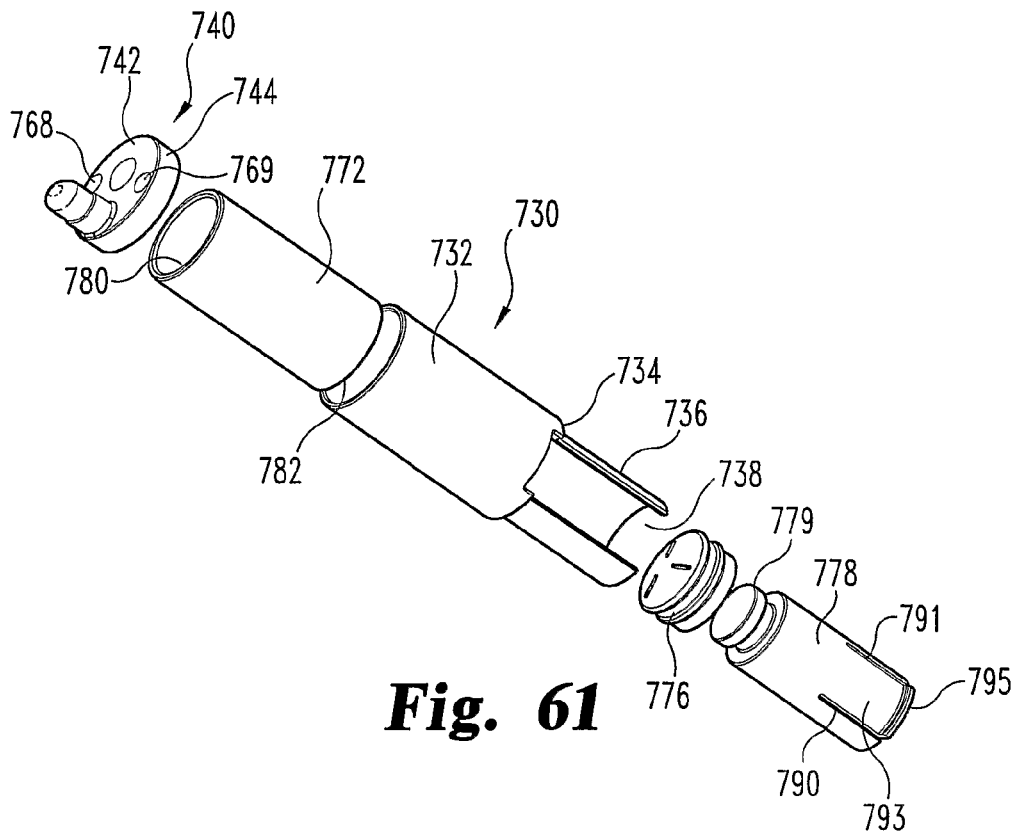
FIG. 61 is a front perspective, exploded view of the drug cartridge of FIG. 59.
Figure 62:
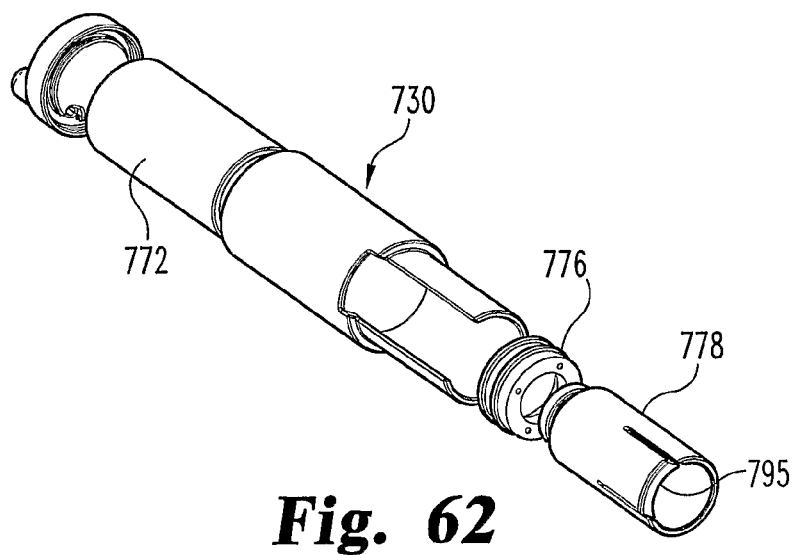
FIG. 62 is a rear perspective, exploded view of the drug cartridge of FIG. 59.
Figure 63:
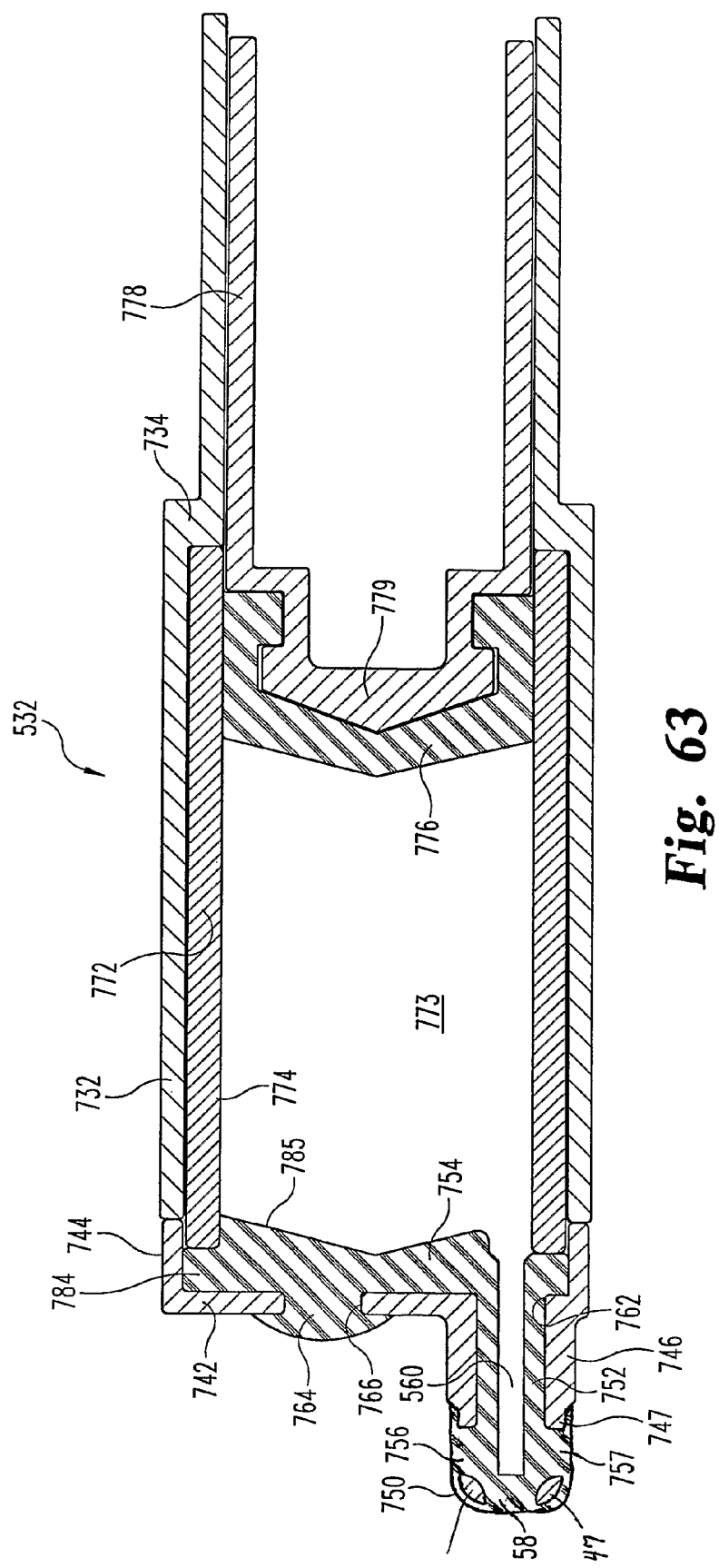
FIG. 63 is a cross-sectional view, taken along line 63-63 of FIG. 60, of the drug cartridge.

The needle-supporting sealing membrane 546 is formed in one-piece of an elastomeric material, such as silicone, and includes a ring-shaped flange 592 having depending tabs 594 that seat within indents 578. A plurality of ovate openings, one corresponding to each of the twenty-one needles, are provided through flange 592, and each opening is ringed by an upstanding shroud or rolling seal 596. A circumferential bead or lip 598 on the inward facing surface of each rolling seal 596 at its upper region is adapted to seat within a groove around the periphery of the needle hub as further shown in FIG. 54. Each seal 596 tapers inwardly in opening size as it proceeds upward from flange 592, and has a thinner region adjacent flange 592, which design allows the shroud to fold or roll into itself when the particular needle assembly 550 to which it remains attached at 598 is plunged during its injecting use, such as shown in FIG. 54.

The undersurface 593 of flange 592 is secured to the upper surface 583 of carousel 544 continuously around each of the slots 580 such that sealing membrane 546 forms individual, sterile upper chambers above the carousel for each of the needle assemblies. The upper surface of sealing membrane 542 similarly is secured to the underside of the carousel around each of the slots 580 to form individual, sterile lower chambers below the carousel for the needles, thereby maintaining needle sterility prior to use.

Figure 66:
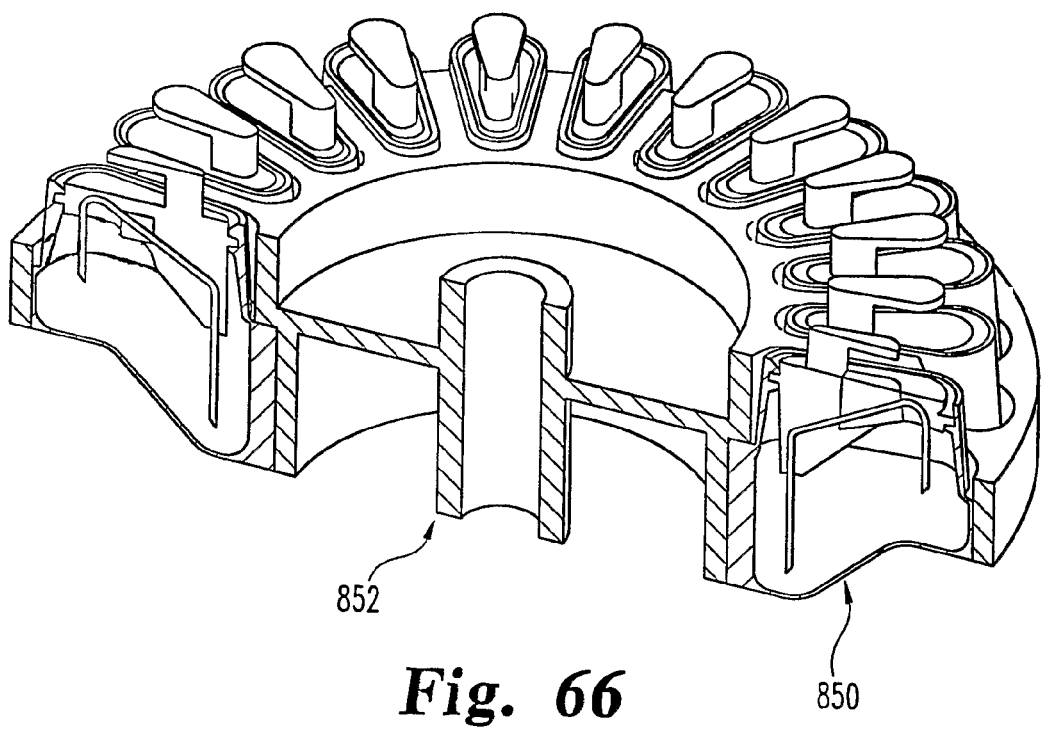
FIG. 66 is a perspective view in cross-section of an alternate carousel with needle-sterility maintaining shroud for the needle cassette.

In an alternate embodiment, the housing of the needle cassette can be equipped with a carousel with a sealing membrane as shown in FIG. 66. In such embodiment, the needle assemblies are held within a shroud 850 formed as a single unit that provides individual compartments for each of the needles. During needle cassette assembly, the needle-equipped shroud 850 is then inserted as a unit from below into the modified carousel 852 as abstractly shown, which is then assembled into a protective housing.

Referring again to FIGS. 50-54, each needle assembly 550 includes a plastic needle hub 600 with a circumferential groove 601 that accommodates lip 598 to provide a sterility maintaining seal. A multi-angled, generally J-shaped lumen or needle 602 includes an end length 603 with a skin-piercing tip 603A, and a parallel, opposite end length 604 with a septum-piercing tip 604A in vertical spaced relationship with each other. End lengths 602 and 604 are spanned by an angled connecting region 605. Needle 602 is 31 gauge needle that is bent to the configuration shown and secured to the hub 600 within a complementary recess, such as via a press fit or with an adhesive. The upper portion of hub 600 includes an L-shaped finger 607 with its longer leg extending radially outward, and which finger 607 together with the upper surface of hub body 606 define a radially-outwardly opening hollow 608. Hollow 608 receives a radially oriented lifting element of lifter assembly 534 as described below. This radial orientation of hollow 608 allows needle cassette 524 to be removed readily from engagement with the lifter assembly at any stage of needle cassette life, allowing a cassette with only a few unused needles remaining to be taken out and replaced with a new, fully loaded cassette if desired.

The exterior or housing top 548 includes a grip portion 610 that complements a grip portion 555 provided on housing bottom 540, which grip portions permit ready handling by the user of the assembled needle cassette 524. The underside of housing top 548 is molded with an apertured protrusion 611 sized and configured to receive keyed post 560, and the protrusion aperture extends through top wall 609 to allow insertion of a fastener. An access port 612 for the lifter assembly extends through both top wall 609 and an arcuate, upstanding wall portion 614 of the top housing. A pair of windows or ports 616 and 617 are formed through the housing top wall 609 to allow sensing of flag element 589 by a not shown sensing mechanism. The underside of top wall 609 also includes a depending ring 620 having an outer radial periphery 621 that serves as a stop to prevent a needle assembly from being inadvertently forced too far radially inward by the lifter assembly during use. Radially inward of ring 620, and ringing protrusion 611, is a series of ratchet teeth 622 that are engaged from below by the carousel ratchet arm 588 to positively locate the carousel and prevent the carousel from rotating in the wrong direction within the housing during use.

Although only one needle assembly 550 is shown in FIGS. 51-53, each of the twenty-one slots 580 is initially equipped with a needle. Needle cassettes with any number of slots with needles may be provided as a function of the intended use of that cassette. For example, if apparatus 500 is intended to deliver a two times daily dosed medicine, and intended to be used for a single week before the needle cassette is to be removed and disposed of, fourteen needles may be provided in such cassette.

Referring now to FIGS. 55-58, there shown a lifter assembly, generally designated 534, of apparatus 500. Lifter assembly 534 is designed to quickly plunge, during an injection, the tips of a single needle assembly into the user and medicine supply in the same downward motion and effectively simultaneously, then to quickly withdraw the inserted needle tips fully back into the needle cassette after the medicine injecting is completed, and then to index the needle cassette to prepare the next available needle assembly in the cassette for use in the next injection.

Lifter assembly 534 includes a rigid frame with a main body 630 from which upwardly projects a support flange 632. A rearward pedestal flange 634 and an L-shaped pedestal flange 636 depend from frame body 630 and receive fasteners to fixedly secure the frame to, for example, the apparatus outer housing. Support flange 632 holds a motor 638 and a gear head 639 operatively connected to the motor. A miter pinion 641 with gear teeth 642 is fixed to the output shaft of gear head 639 to be rotated thereby when the motor is controllably operated by the control system of apparatus 500.

Pinion 641 drives the rotation of bevel gear 644 via the meshing of gear teeth 642 with gear teeth 645. Bevel gear 644 is co-rotatable with a geneva disc 646 and a cam disc 650. In the shown embodiment, such co-rotation may be achieved with the bevel gear being secured to an axially protruding, central hub of the geneva disc, with the geneva disc in turn being secured to an axially protruding, central hub of the cam disc 650, and with the cam disc press fit and bonded to a rod 651 that axially extends through and supports gear 644 and discs 646 and 650. Rod 651 is mounted to the apparatus housing so as to be rotatable. Other manners of providing for this corotation may be readily substituted within the scope of the invention.

Geneva disc 646 with its radially protruding pin 647 is positioned to fit within the opening 567 of an installed needle cassette 524 so as to engage the tabs 579 and notches 581 of carousel 544. Cam disc 650 is vertically or axially spaced from geneva disk 646 to provide a space in which extends a forward arm 659 of a latching member 660. Cam disc 650 includes an arcuate, radial protrusion or camming portion 652 having a radially aligned end face 653. The upper surface 656 of cam disc 650 has machined into it a cam track that interacts with a follower on the forward arm 659. Latching member 660 is pivotally connected to the frame at 661. A rearward arm 662 of latching member 660 includes an inwardly facing latch element (not shown) adapted to latchably engage a complementary element of a recessed latch surface 664 of a slider 666 that extends beneath frame body 630. A throughhole in slider 666 receives a guide rod 668 that is fixedly connected at opposite ends to pedestal flanges 634, 636. Slider 666 slides back and forth along guide rod 668 during operation as described further below.

Slider 666 is equipped with a metal rack 670 fixedly secured thereto and which projects laterally of frame body 630. The row of teeth 671 of rack 670 face upwardly. Slider 666 includes another throughbore that slidably receives a lifter rod 674 that slides within bores through frame flanges 634, 636. The forward end of lifter rod 674 abuts the cam disc 650 along its exterior periphery having the camming portion 652. A lock ring 676 is axially fixed on lifter rod 674, and a helical compression spring 678 is captured between lock ring 676 and the forward face 677 of frame flange 634. Spring 678 is coaxial with the lifter rod 674 and serves to bias upward the lifter after an medicine injecting is completed. A second lock ring 680 is axially fixed on lifter rod 674 and captures with a forward face 682 of slider 666 a second helical compression spring 684 that is coaxial with the lifter rod 674 and which serves to bias downward the lifter at the start of an injection.

Lifter assembly 534 also includes a pair of parallel guide rods 687 and 688 that are fixed within the apparatus housing and which slidably support metal glide blocks 690 and 691. A transversely extending arm 692 is formed with and rigidly spans glide blocks 690, 691. Arm 692 includes a forwardly projecting lifter 694 including an upper ear 696 and a vertically spaced lower ear 697 that together define a recess 699 configured to receive needle assembly finger 607. A not shown mechanical switch or other suitable sensing element circuited with the apparatus control system and mounted to sense transverse arm 692 when in the upward, or non-plunged, position shown in FIGS. 55-58 is used by the control system to determine the arrangement of the lifter assembly in order to control apparatus 500.

Glide block 690 includes a rearward facing rack 702 having teeth 704 in meshed engagement with gear teeth 706 of a pinion portion 708 pivotally mounted to the lifter assembly frame at 709. A smaller diameter pinion 710 corotatable with pinion portion 708 is also pivotally mounted to the frame at 709. Pinion portion 708 and pinion 710 may be integrally formed, or separately formed and secured together, so as to rotate together about pivot 709. The gear teeth 712 along the outer radial periphery of pinion 710 are in meshed engagement with teeth 671 of slider rack 670.

The lifter assembly 534 is controlled by the apparatus control system in preparation for an injection by having motor 638 operated to drive, via the intervening transmission components, the turning of cam disc 650 until camming portion 652 drives lifter rod 674 rearward. As lifter rod 674 shifts rearward, spring 678 is compressed against flange face 677, and spring 684 is compressed against slider face 682 due to slider 666 still being held relative to the frame as it is latched by latching member 660. When injection button is 510 is subsequently pressed by a user to begin an injection, the control system causes motor 638 to initially turn cam disc 650 slightly further so as to cause the latching member 660, due to the configuration of the camming track it follows, to pivot about 661 and disengage from slider 666, allowing slider 666 to shift quickly rearward as biased by compressed spring 684. As slider 666 shifts rearward, rack 670 shifts rearward, which rotates pinion 710 and pinion portion 708 so as to drive the rack 702, and therefore the needle assembly being engaged by lifter 694 as shown in FIG. 54, downward. When the direct drive assembly has forced the appropriate dose of medicine from the drug cartridge such that the medicine injecting is completed, the control system causes motor 638 to turn cam disc 650 still further such that camming portion end face 653 rotates past the forward end of the lifter rod 674, thereby allowing the lifter rod to shift forward quickly relative to the frame under the influence of compressed spring 678. As lifter rod 674 shifts forward, slider 666 is abutted by lock ring 676 and driven forward, which shifts rack 670 forward and rotates pinion 710 and pinion portion 708 so as to shift rack 702 and lifter 694 upward, thereby automatically withdrawing the needle tips 603A and 604A from the user and the drug cartridge, respectively. The cam disc 650 continues to be turned to prepare for the next injection, during which time the latching member 660, due to the shape of the camming track it follows, pivot back about 661 to reengage or relatch slider 666.

Referring now to FIGS. 59-63, there is shown drug cartridge 532 that is particularly adapted for use in apparatus 500. Drug cartridge 532, which provides a suitable shape without necessitating unconventional materials be in contact with the medicine that may have implications with respect to long term storage of such medication, includes a tubular outer housing or sheath 730 made of plastic. Housing 730 includes a larger diameter portion 732 that steps down at wall 734 to a smaller diameter portion 736 including a slide window 738. The forward end of housing 730 is capped by a co-molded cap 740 having a rigid plastic base piece including a disc-shaped body 742 with a mounting collar 744 and a radially offset, hollow protuberance 746. The offsetting of protuberance 746 results in a cartridge shape that in use serves as a keying to facilitate proper insertion of the drug cartridge into the correspondingly configured compartment within the apparatus housing. Mounting collar 744 is fixedly secured to the forward end of sheath portion 732 during manufacture.

The sealing material of cap 740, which during manufacture is comolded to the rigid base piece, forms a cup-shaped element 750, a protuberance liner 752, and a sealing disc 754. The sealing material may be one or more materials, such as polyisoprene or butyl rubber, that provide appropriate sealing properties while being compatible with the contained medication. Cup-shaped element 750 overlays a smaller dimensioned end region 747 of protuberance portion 746 and fills protuberance openings 756, 757 and 758 to provide fluid tight seals, and serves as pierceable septums for openings 756 and 757. Opening 756 serves as a dispensing port of cartridge 532. Opening 757 is disposed directly across the protuberance hollow 760 from opening 756 and may serve as a filling port for a version of the invention described below. Opening 758 facilitates the comolding process. Liner 752 lines hollow 760 and extends through an off-center opening 762 in disc-shaped body 742 where it terminates in the sealing disc 754 that lines the interior surface of disc-shaped body 742. A plug portion 764 sealingly fills a central opening 766 in disc-shaped body 742 which may serve as an auxiliary filling port. Additional plug portions 768 and 769 sealingly fit within openings in body 742 and ensure a secure connection between the comolded parts.

A cylindrical sleeve 772 made of glass is protectively captured within sheath 730 and includes an interior surface 774 along which sealably slides a resilient seal 776. Seal 776 is made of a conventional material and is mounted on a resilient plastic plunger 778. Sleeve 772 provides a reservoir 773 for medicine to be dispensed by apparatus 500. Reservoir may be provided prefilled to a user, or may be fillable by a user prior to its use, such as manually with a syringe type device prior to the drug cartridge being loaded into the apparatus, or by use of the apparatus such as described below with respect to FIGS. 67 and 68. The connection of seal 776 to plunger 778, which is shown at 779 as a plug that snap fits into a hollow of the seal, allows seal 776 to be moved by plunger 778 either forward or rearward within sleeve 772. Other forms of seal/plunger connections may alternatively be employed if such forward and rearward plunger driven motions are required, such as when filling occurs in the manner described below with respect to FIGS. 67 and 68. Sleeve 772 is captured with its rearward end 782 against the interior surface of housing wall 734 and with its forward annular end 780 in sealing engagement with an annular lip 784 of sealing disc 754. A central region 785 of sealing disc 754 axially protrudes inward of lip 784 to further seal with glass sleeve 772.

Plunger 778 includes parallel slots 790 and 791 longitudinally extending from its rearward end to define a cammable finger 793. A lip 795 at the rear end of finger 793 projects radially outward within slide window 738.

Figure 64:
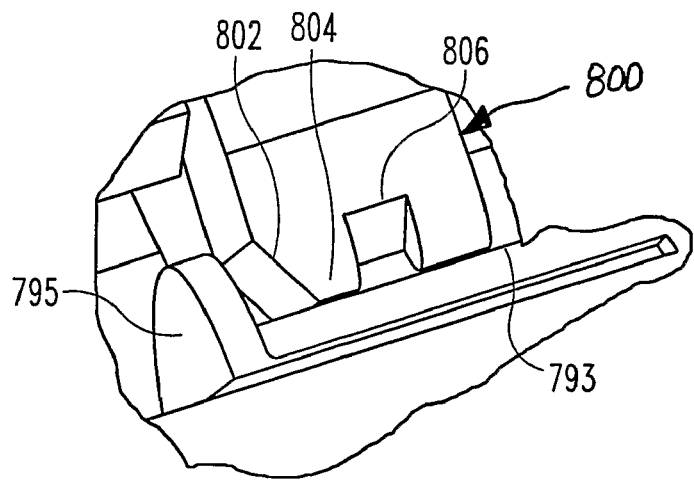
FIG. 64 is a diagrammatic, partial perspective view of a drug cartridge plunger and a drive assembly carriage prior to their engagement.
Figure 65:
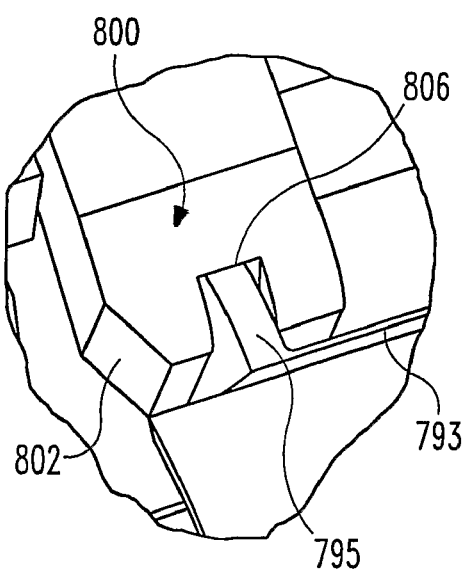
FIG. 65 is a diagrammatic, partial perspective view of the drug cartridge plunger and drive assembly carriage of FIG. 64 after their engagement.

Plunger finger 793 and lip 795 are cooperatively designed with an engagement member provided on direct drive assembly 536. As abstractly shown in the partial views of FIGS. 64 and 65, the direct drive assembly includes a carriage 800 that is rotatably fixed and which is shiftable forward or rearward along a motor-rotated threaded shaft of that assembly Only carriage 800 of the direct drive assembly of apparatus 500 is shown, as such direct drive assembly is essentially the same as the direct drive assembly of apparatus 10 shown in, for example, FIGS. 20 and 21, but with the carriage 800 and its control described below replacing the pivoting arm and associated sensor plank of apparatus 10.

Carriage 800 includes an angled rearward face 802 for camming purposes. Camming face 802 leads to a shoulder 804 having an indent 806 therein. When a drug cartridge is initially loaded, carriage 800 is controlled to be in a forward position, and is then caused to move rearward. As carriage 800 is so moved, the motor of the direct drive assembly 536 experiences minimal resistance until camming face 802 initially contacts plunger lip 795. The direct drive assembly motor continues to move carriage 800 rearwardly, and in so doing cams radially inward the plunger finger 793, which camming requires additional motor power that is sensed by the apparatus control system. The motor power may continue at an increased level until the motor has shifted the carriage sufficiently rearward such that plunger lip 795, due to the resiliency of the construction of plunger finger 793, snap inserts into indent 806. The decrease in motor power resulting from the camming of the plunger finger having ended is recognized by the control system of apparatus 500, which then controls the assembly motor to halt the rearward motion of the carriage 800 and subsequently move the carriage forward in the normal course of apparatus use.

Figure 67:
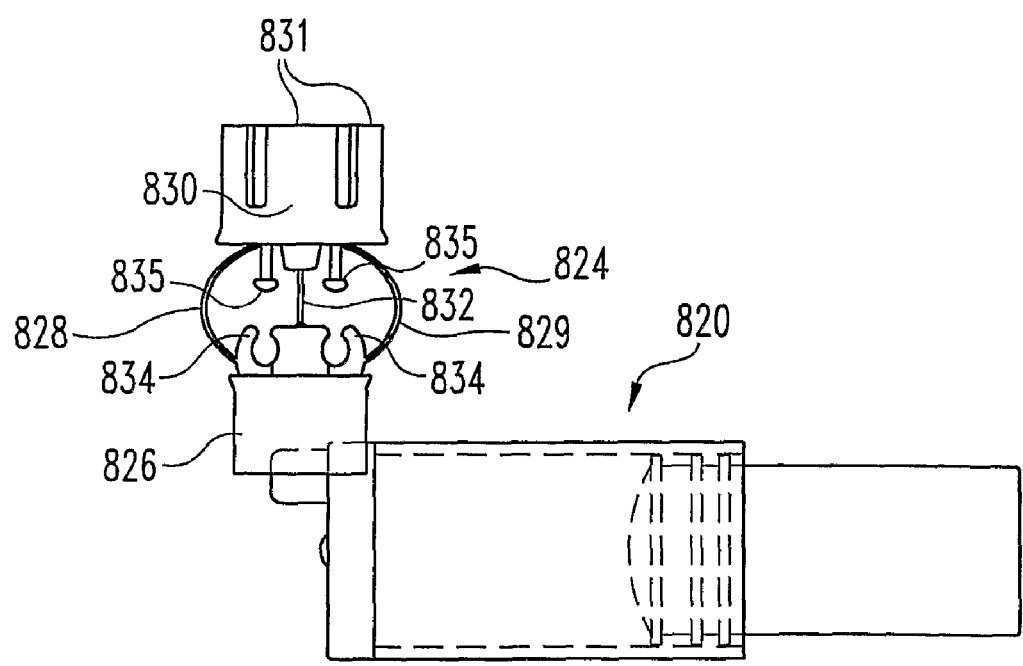
FIG. 67 is a front view of a drug cartridge equipped with a filling adaptor.
Figure 68:
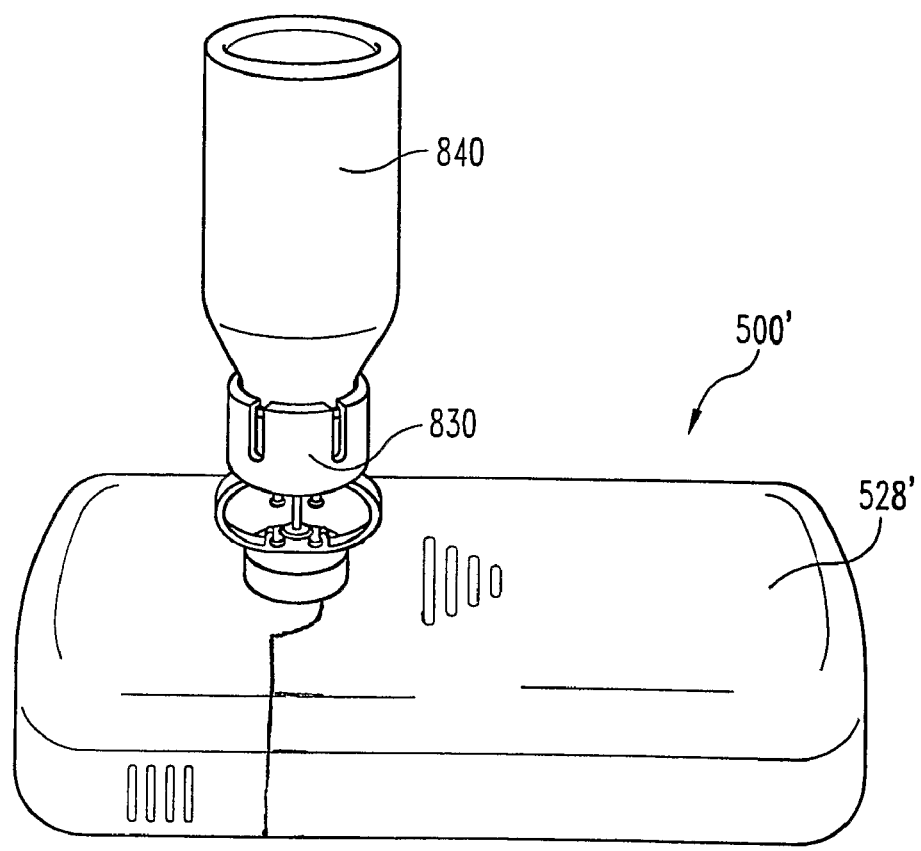
FIG. 68 is a perspective view of an apparatus of the present invention loaded with the adaptor-equipped drug cartridge of FIG. 67.

With reference now to FIGS. 67 and 68, a method of using an apparatus of the present invention to allow ready filling with medication supplied within a standard vial is described. A plurality of drug cartridges all fillable with the contents of a single vial may be provided in a pack. For a ten milliliter vial, four identical drug cartridges may form such pack. One of the drug cartridges of the pack is shown at 820 in FIG. 67, and is similar to the drug cartridges described above with respect to FIGS. 59-63. Cartridge 820 is supplied in the pack with its plunger in a retracted position, whereby its medicine fillable reservoir is initially filled with air. Cartridge 820 is supplied pre-coupled with a needled adaptor, generally referenced at 824. Adaptor 824 includes a mounting collar 826 removably connected to the drug cartridge. Mounting collar 826 is attached via flexible webs 828 and 829 to a vial mounting collar 830 having flexible fingers 831 adapted to releasably hold a vial 840. Collar 830 carries a double-ended needle 832 having a first end that extends within collar 830 and which is positioned to pierce the septum of vial 840 when the vial is mounted to collar 830. The opposite needle end is spaced from the septum of cartridge 820 when the adaptor 824 is arranged in its supplied condition as shown in FIG. 67. Complimentary latching members 834 and 835 are provided on collars 826 and 830, respectively.

To fill drug cartridge 820, a user inserts cartridge 820 into the apparatus 500' shown in FIG. 68 and closes the access panel 528', which panel, or the interior of the housing, is designed to releasably engage adaptor collar 826. With apparatus 500' placed on a support surface so that the underside of the apparatus faces upward as shown in FIG. 68, vial 840 is manually inserted by a user into vial mounting collar 830, causing needle 832 to pierce the vial septum, and then forced downward to drive collar 830 toward collar 826 so as to engage latching members 834, 835, during which motion the needle 832 pierces the septum of the filling port of the cartridge.

A fill button on apparatus 500' is then pressed by the user to begin the filling cycle. The direct drive assembly first will advance the cartridge plunger all the way forward so that the air initially present within the cartridge reservoir is forced into vial 840 to pressurize it. The direct drive assembly then retracts the cartridge plunger to backfill the cartridge with medicine from the vial. In order to avoid air bubbles in a filled cartridge, the orientation of the apparatus is preferably monitored with a sensor integrated into the device, which sensor allows the fill cycle to occur only if apparatus 500' is in a proper orientation shown in FIG. 68. Once the fill cycle is complete, a user may detach the needle adaptor with vial from cartridge 820, close the access panel if necessary and thereafter use apparatus 500' in the normal course. Needle adaptor 824 is be snapped off of vial 840 and disposed of in a proper container, leaving the partially emptied vial 840 to be reused at a later date with other drug cartridges in the pack, each of which other empty cartridges is supplied with its own disposable needled adaptor.

In order to maximize the battery life of apparatus 500', a modified plunger advancing/retracting profile that minimizes the power consumed by the apparatus may be employed. For example, it may be advisable to advance the cartridge plunger only halfway during the filling of the vial with air, after which the plunger can be retracted fully to partially fill the reservoir, and then advanced fully and retracted fully within the drug cartridge to fill the reservoir.

The control system of apparatus 500 may be programmed with an automated calibration procedure so as to reduce the need for a priming step to purge air bubbles from a drug cartridge. When a drug cartridge is first inserted into such a programmed apparatus 500, and without a needle piercing the dispensing port of the cartridge, the direct drive assembly is operated to advance the cartridge plunger to compress the medication in the cartridge reservoir. During this compression, the control system monitors the time and current being drawn by the drive assembly motor, which time and current relationship is then compared to a lookup table preprogrammed in the apparatus electronics and populated with empirically determined data as to time/current relationships associated with particular air bubble sizes. The control system uses the determined air bubble size in order to make appropriate changes to the dosing profile to ensure an accurate dose, such as by increasing the hold time of the inserted needle before the needle assembly is retracted, or by providing a warning notifying the user if too much air is present in the cartridge.

Materials recited herein for certain parts are for example only in the current embodiments. Alternative embodiments are contemplated wherein alternate materials may be used, particularly where similar and/or improved results may occur.

While the invention has been illustrated and described in detail in the drawings and foregoing description, the same is to be considered as illustrated and not restrictive in character, it being understood that only the preferred embodiment and a few alternative embodiments have been shown and described and that all changes and modifications that come within the spirit of the invention are desired to be protected.

What is claimed is:

1. An apparatus for delivering a pharmaceutical liquid to a patient, comprising:
    an outer casing;
    a needle cassette housed in said casing including a rotatable body and containing a plurality of mutually parallel drug injection needles, each injection needle has an associated septum piercing needle arranged parallel thereto and pointing in the same direction, each said septum piercing needle and its associated injection needle in mutual fluid communication;
    a single drug cartridge housed in said casing, and including a sealing plunger shiftable within a cartridge body in a direction generally perpendicular to the injection needles, said cartridge containing the liquid and including a pierceable septum for accessing the liquid;
    a direct drive assembly housed in said casing and engageable with said drug cartridge sealing plunger to expel a measured dose of the liquid through a septum piercing needle and its associated injection needle when the septum is pierced by that septum piercing needle;
    a lifter assembly engageable with said needle cassette to drive one of said plurality of injection needles and its associated septum piercing needle such that said driven injection needle extends partially out of said casing and into a patient and said driven associated septum piercing needle pierces the septum to access the liquid in said drug cartridge, and thereafter to withdraw the driven injection needle from the patient while withdrawing the driven associated septum piercing needle from the septum to halt accessing of the liquid through the septum after the measured dose of the liquid has been administered through the septum piercing needle and the injection needle, and thereafter to rotate the rotatable body to index the next one of said plurality of injection needles and its associated septum piercing needle for use with the single drug cartridge and its pierceable septum;
    motor means for driving said direct drive assembly and said lifter assembly;
    computer means for activating said direct drive assembly and said lifter assembly; and
    a control panel for enabling a user to activate said apparatus.

2. The apparatus of claim 1 wherein an axis of rotation of said needle cassette body is parallel to said drug injection needles, said body including a plurality of needle openings each sized and configured for receipt of one injection needle.

3. The apparatus of claim 2 wherein said needle cassette includes a cassette housing rotatably fixed relative to said outer casing when removably installed therein, said body mounted in the cassette housing for rotation therein about said axis of rotation.

4. The apparatus of claim 2 wherein the needle openings each have an interior shape, wherein a plurality of needle assemblies comprise said plurality of injection needles, wherein said needle assemblies each have an exterior shape complementary to the interior shape, and wherein said needle assemblies are received in said needle openings for reciprocation therein.

5. The apparatus of claim 2 wherein the body defines a plurality of indexing notches configured for engagement with a geneva wheel of said lifter assembly.

6. The apparatus of claim 5 wherein said needle cassette further comprises means for permitting rotation of the body in only one direction.

7. The apparatus of claim 2 wherein said needle cassette includes means cooperating with said computer means to allow detection of at least certain angular positions of the body about said axis of rotation.

8. The apparatus of claim 3 wherein said needle cassette housing defines an opening sized and configured to permit vertical reciprocation of an element of said lifter assembly therethrough to drivingly engage an injection needle.

9. The apparatus of claim 2 wherein each injection needle is held by a rolling seal adapted to elastically deform during movement of said injection needle by said lifting assembly.

10. The apparatus of claim 1 wherein said direct drive assembly includes a motor driven carriage engageable with a plunger of said drug cartridge, said carriage including a camming surface adapted to bias a resilient member of said plunger during an operative attachment of said carriage to said plunger.

11. The apparatus of claim 1 wherein said lifter assembly includes a slider mounted on a lifter rod, and first and second biasing springs, said first biasing spring adapted to move an unlatched slider along said lifter rod in a first direction, said second biasing spring adapted to move said lifter rod and said slider in a second direction opposite said first direction.

12. The apparatus of claim 11 wherein said lifter assembly comprises a rotatable disc adapted to cam said lifter rod in the first direction while compressing said second biasing spring.

13. The apparatus of claim 1 wherein said lifter assembly comprises a slider including a first rack, an injection needle shifting lifter including a second rack, and first and second pinion portions engaging said first and said second racks, respectively, to translate motion of said slider into a motion of said lifter.

14. The apparatus of claim 1 wherein said outer casing includes an openable drawer sized to insertably receive said needle cassette.

15. The apparatus of claim 1 wherein said needle cassette is integrated into an openable drawer of the outer casing so as to be disposable as a unit.

* * * * *

UNITED STATES PATENT AND TRADEMARK OFFICE
CERTIFICATE OF CORRECTION

PATENT NO. : 8,057,434 B2  Page 1 of 1
APPLICATION NO. : 10/598990
DATED : November 15, 2011
INVENTOR(S) : Andrew Christopher Burroughs et al.

It is certified that error appears in the above-identified patent and that said Letters Patent is hereby corrected as shown below:

On the Title page:
Insert Item -- [60] Related U.S. Application Data
Provisional application no. 60/558,412, filed on March 31, 2004 --

Col. 1, lines 4-5, insert the following cross-reference after the title:
-- This is the national phase application, under 35 USC 371, for PCT/US2005/010580, filed 30 March 2005, which, claims the benefit, under 35 USC 119(e), of US provisional application 60/558,412, filed 31 March 2004. --

Signed and Sealed this
Fourth Day of December, 2012

David J. Kappos
*Director of the United States Patent and Trademark Office*